(12) United States Patent
Nakai et al.

(10) Patent No.: US 12,084,654 B2
(45) Date of Patent: Sep. 10, 2024

(54) METHODS FOR USING TRANSCRIPTION-DEPENDENT DIRECTED EVOLUTION OF AAV CAPSIDS

(71) Applicant: Oregon Health & Science University, Portland, OR (US)

(72) Inventors: Hiroyuki Nakai, Portland, OR (US); Samuel Huang, Portland, OR (US); Kei Adachi, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 18/160,804

(22) Filed: Jan. 27, 2023

(65) Prior Publication Data

US 2023/0287405 A1 Sep. 14, 2023

Related U.S. Application Data

(63) Continuation of application No. 17/822,111, filed on Aug. 24, 2022, which is a continuation of application No. 17/337,341, filed on Jun. 2, 2021, now Pat. No. 11,459,558, which is a continuation of application No. PCT/US2020/016273, filed on Jan. 31, 2020.

(60) Provisional application No. 62/799,603, filed on Jan. 31, 2019.

(51) Int. Cl.
```
C12N 15/11      (2006.01)
C12N 7/00       (2006.01)
C12N 15/10      (2006.01)
C12N 15/86      (2006.01)
```

(52) U.S. Cl.
CPC ............... *C12N 15/11* (2013.01); *C12N 7/00* (2013.01); *C12N 15/1082* (2013.01); *C12N 15/86* (2013.01); *C12N 2310/11* (2013.01); *C12N 2320/33* (2013.01); *C12N 2750/14122* (2013.01); *C12N 2750/14123* (2013.01); *C12N 2750/14142* (2013.01); *C12N 2750/14145* (2013.01); *C12N 2830/008* (2013.01)

(58) Field of Classification Search
CPC ... C12N 15/11; C12N 15/86; C12N 2830/008
USPC ..... 435/6.1, 91.1, 91.31, 455, 458; 530/300, 530/350; 536/23.1, 24.5
See application file for complete search history.

(56) References Cited

U.S. PATENT DOCUMENTS

| | | | |
|---|---|---|---|
| 5,866,552 A | 2/1999 | Wilson et al. | |
| 5,871,982 A | 2/1999 | Wilson et al. | |
| 6,174,527 B1 | 1/2001 | Wilson et al. | |
| 6,251,677 B1 | 6/2001 | Wilson et al. | |
| 6,258,595 B1 | 7/2001 | Gao et al. | |
| 6,274,354 B1 | 8/2001 | Wilson et al. | |
| 6,387,368 B1 | 5/2002 | Wilson et al. | |
| 6,475,769 B1 | 11/2002 | Wilson et al. | |
| 6,482,634 B1 | 11/2002 | Wilson et al. | |
| 6,485,966 B2 | 11/2002 | Gao et al. | |
| 6,759,237 B1 | 7/2004 | Wilson et al. | |
| 6,943,019 B2 | 9/2005 | Wilson et al. | |
| 6,953,690 B1 | 10/2005 | Gao et al. | |
| 7,022,519 B2 | 4/2006 | Gao et al. | |
| 7,105,345 B2 | 9/2006 | Wilson et al. | |
| 7,186,552 B2 | 3/2007 | Wilson et al. | |
| 7,198,951 B2 | 4/2007 | Gao et al. | |
| 7,235,393 B2 | 6/2007 | Gao et al. | |
| 7,238,526 B2 | 7/2007 | Wilson et al. | |
| 7,282,199 B2 | 10/2007 | Gao et al. | |
| 7,319,002 B2 | 1/2008 | Wilson et al. | |
| 7,344,872 B2 | 3/2008 | Gao et al. | |
| 7,491,508 B2 | 2/2009 | Roy et al. | |
| 7,588,772 B2 | 9/2009 | Kay et al. | |
| 7,790,449 B2 | 9/2010 | Gao et al. | |
| 7,906,111 B2 | 3/2011 | Wilson et al. | |
| 8,067,014 B2 | 11/2011 | Kay et al. | |
| 8,129,510 B2 | 3/2012 | Kay et al. | |
| 8,231,880 B2 | 7/2012 | Roy et al. | |
| 8,318,480 B2 | 11/2012 | Gao et al. | |
| 8,394,386 B2 | 3/2013 | Wilson | |
| 8,445,454 B2 | 5/2013 | Wu et al. | |
| 8,470,310 B2 | 6/2013 | Roy et al. | |
| 8,524,219 B2 | 9/2013 | Roy et al. | |
| 8,524,446 B2 | 9/2013 | Gao et al. | |
| 8,574,583 B2 | 11/2013 | Kay et al. | |
| 8,603,459 B2 | 12/2013 | Wilson et al. | |
| 8,628,966 B2 * | 1/2014 | Chatterjee | A61K 48/00 530/350 |
| 8,637,255 B2 | 1/2014 | Wilson et al. | |
| 8,685,387 B2 | 4/2014 | Roy et al. | |
| 8,834,863 B2 | 9/2014 | Roy et al. | |
| 8,846,031 B2 | 9/2014 | Roy et al. | |
| 8,906,387 B2 | 12/2014 | Kay et al. | |
| 8,906,675 B2 | 12/2014 | Gao et al. | |

(Continued)

FOREIGN PATENT DOCUMENTS

| JP | H1051126 A | 2/1998 |
|---|---|---|
| WO | WO-0177350 A2 | 10/2001 |

(Continued)

OTHER PUBLICATIONS

U.S. Appl. No. 17/337,341 (Year: 2021).*

(Continued)

*Primary Examiner* — Jane J Zara

(74) *Attorney, Agent, or Firm* — Wilson Sonsini Goodrich & Rosati

(57) ABSTRACT

Disclosed are methods for performing transcription-dependent directed evolution (TRADE) and novel AAV capsids selected using such methods.

12 Claims, 43 Drawing Sheets

Specification includes a Sequence Listing.

(56) References Cited

U.S. PATENT DOCUMENTS

| | | |
|---|---|---|
| 8,940,290 B2 | 1/2015 | Roy et al. |
| 8,962,330 B2 | 2/2015 | Gao et al. |
| 8,962,332 B2 | 2/2015 | Gao et al. |
| 8,999,678 B2 | 4/2015 | Vandenberghe et al. |
| 9,150,882 B2 | 10/2015 | Kay et al. |
| 9,163,260 B2 | 10/2015 | Wilson et al. |
| 9,169,299 B2 | 10/2015 | Lisowski et al. |
| 9,198,984 B2 | 12/2015 | Lock et al. |
| 9,315,825 B2 | 4/2016 | Wilson et al. |
| 9,359,618 B2 | 6/2016 | Roy et al. |
| 9,382,551 B2 | 7/2016 | Roy et al. |
| 9,493,788 B2 | 11/2016 | Gao et al. |
| 9,567,607 B2 | 2/2017 | Wilson et al. |
| 9,587,250 B2 | 3/2017 | Gao et al. |
| 9,593,346 B2 | 3/2017 | Roy et al. |
| 9,597,363 B2 | 3/2017 | Roy et al. |
| 9,617,561 B2 | 4/2017 | Roy et al. |
| 9,677,089 B2 | 6/2017 | Gao et al. |
| 9,719,106 B2 | 8/2017 | Wilson et al. |
| 9,737,618 B2 | 8/2017 | Wilson et al. |
| 9,770,011 B2 | 9/2017 | Wilson et al. |
| 9,783,824 B2 | 10/2017 | Kay et al. |
| 9,790,472 B2 | 10/2017 | Gao et al. |
| 9,856,469 B2 | 1/2018 | Lisowski et al. |
| 9,884,071 B2 | 2/2018 | Wilson et al. |
| 9,890,365 B2 | 2/2018 | Wang et al. |
| 10,041,090 B2 | 8/2018 | Gao et al. |
| 10,113,182 B2 | 10/2018 | Roy et al. |
| 10,137,176 B2 | 11/2018 | Wilson et al. |
| 10,138,295 B2 | 11/2018 | Wilson et al. |
| 10,149,873 B2 | 12/2018 | Roy et al. |
| 10,155,931 B2 | 12/2018 | Lock et al. |
| 10,167,454 B2 | 1/2019 | Wang et al. |
| 10,179,176 B2 | 1/2019 | Kay et al. |
| 10,265,417 B2 | 4/2019 | Wilson et al. |
| 10,266,846 B2 | 4/2019 | Gao et al. |
| 10,301,648 B2 | 5/2019 | Vandenberghe et al. |
| 10,301,650 B2 | 5/2019 | Gao et al. |
| 10,308,958 B2 | 6/2019 | Gao et al. |
| 10,335,466 B2 | 7/2019 | Kotin et al. |
| 10,385,119 B2 | 8/2019 | Wilson et al. |
| 10,385,320 B2 | 8/2019 | Kay et al. |
| 10,406,173 B2 | 9/2019 | Wilson et al. |
| 10,406,244 B2 | 9/2019 | Kay et al. |
| 10,485,883 B2 | 11/2019 | Wilson et al. |
| 10,501,757 B2 | 12/2019 | Roy et al. |
| 10,508,286 B2 | 12/2019 | Gao et al. |
| 10,526,617 B2 | 1/2020 | Gao et al. |
| 10,532,111 B2 | 1/2020 | Kay et al. |
| 10,544,432 B2 | 1/2020 | Gao et al. |
| 10,570,395 B2 | 2/2020 | Hou et al. |
| 10,577,627 B2 | 3/2020 | Kotin et al. |
| 10,584,337 B2 | 3/2020 | Sah et al. |
| 10,590,435 B2 | 3/2020 | Gao et al. |
| 10,597,660 B2 | 3/2020 | Sah et al. |
| 10,612,041 B2 | 4/2020 | Barzel et al. |
| 10,626,382 B2 | 4/2020 | Wang et al. |
| 10,626,415 B2 | 4/2020 | Vandenberghe et al. |
| 10,647,758 B2 | 5/2020 | Wilson et al. |
| 10,647,998 B2 | 5/2020 | Wilson et al. |
| 10,695,441 B2 | 6/2020 | Wilson et al. |
| 10,722,598 B2 | 7/2020 | Wilson et al. |
| 11,459,558 B2 * | 10/2022 | Nakai ................ C12N 7/00 |
| 2004/0132042 A1 | 7/2004 | Frankard et al. |
| 2005/0148076 A1 | 7/2005 | Allen |
| 2010/0260800 A1 | 10/2010 | Bartlett et al. |
| 2013/0035472 A1 | 2/2013 | Horlick et al. |
| 2013/0224836 A1 | 8/2013 | Muramatsu |
| 2013/0296409 A1 | 11/2013 | Miller et al. |
| 2013/0323226 A1 | 12/2013 | Wilson et al. |
| 2016/0333375 A1 | 11/2016 | Chen |
| 2017/0067908 A1 | 3/2017 | Nakai et al. |
| 2023/0119163 A1 | 4/2023 | Nakai et al. |
| 2023/0193315 A1 | 6/2023 | Nakai et al. |
| 2023/0287404 A1 | 9/2023 | Nakai et al. |

FOREIGN PATENT DOCUMENTS

| | | | |
|---|---|---|---|
| WO | WO-2012112832 A1 * | 8/2012 | ........... A61K 31/685 |
| WO | WO-2017197355 A2 | 11/2017 | |
| WO | WO-2018119330 A2 | 6/2018 | |
| WO | WO-2019079496 A2 | 4/2019 | |
| WO | WO-2020072683 A1 | 4/2020 | |
| WO | WO-2020160508 A1 | 8/2020 | |

OTHER PUBLICATIONS

U.S. Appl. No. 17/822,111 (Year: 2022).*

Pendse: Improving Gene Therapy Viral Vectors via Capsid Engineering | ASGCT—American Society of Gene & Cell Therapy. pp 1-6 XP5959770 (2022).

Adachi et al.: A New Recombinant Adeno-Associated Virus (AAV)-Based Random Peptide Display Library System: Infection-Defective AAV1.9-3 as a Novel Detargeted Platform for Vector Evolution. Gene Therapy and Regulation. 5(1):31-55 (2010) doi: 10.1142/S1568558610000197.

Adachi et al.: Adeno-associated virus-binding antibodies detected in cats living in the Northeastern United States lack neutralizing activity. Sci Rep. 10(1):10073 (2020) doi: 10.1038/s41598-020-66596-4.

Adachi et al.: Drawing a high-resolution functional map of adeno-associated virus capsid by massively parallel sequencing. Nat Commun. 5:3075 (2014) doi: 10.1038/ncomms4075.

Cabanes-Creus et al.: Codon-Optimization of Wild-Type Adeno-Associated Virus Capsid Sequences Enhances DNA Family Shuffling while Conserving Functionality. Mol Ther Methods Clin Dev. 12:71-84 (2018) doi: 10.1016/j.omtm.2018.10.016.

Deverman, et al. Cre-dependent selection yields AAV variants for widespread gene transfer to the adult brain. Nature biotechnology34.2 (Feb. 2016): 204.

Dong et al.: Characterization of genome integrity for oversized recombinant AAV vector. Mol Ther. 18(1):87-92 (2010) doi: 10.1038/mt.2009.258.

Earley et al.: Adeno-associated Virus (AAV) Assembly-Activating Protein Is Not an Essential Requirement for Capsid Assembly of AAV Serotypes 4, 5, and 11. J Virol. 91(3):e01980-16 (2017) doi: 10.1128/JVI.01980-16.

Earley et al.: Identification and characterization of nuclear and nucleolar localization signals in the adeno-associated virus serotype 2 assembly-activating protein. J Virol. 89(6):3038-48 (2015) doi: 10.1128/JVI.03125-14 Epub Dec. 31, 2014.

Fischer et al.: Direct injection into the dorsal root ganglion: technical, behavioral, and histological observations. J Neurosci Methods. 199(1):43-55 (2011) doi: 10.1016/j.jneumeth.2011.04.021.

Grimm et al.: Liver transduction with recombinant adeno-associated virus is primarily restricted by capsid serotype not vector genotype. J Virol. 80(1):426-439 (2006) doi: 10.1128/JVI.80.1.426-439.2006.

Grimm et al.: Preclinical in vivo evaluation of pseudotyped adeno-associated virus vectors for liver gene therapy. Blood. 102(7):2412-2419 (2003).

Huang et al.: Cell Type-Specific TRAnscription-Dependent Directed Evolution (TRADE) Identifies Novel AAV Capsids Capable of Enhanced Neuronal Transduction in Mice and Non-Human Primates. Molecular Therapy. 27(4S1):24-25 (2019).

Inagaki et al.: The role of DNA-PKcs and artemis in opening viral DNA hairpin termini in various tissues in mice. J Virol. 81(20):11304-21 (2007) doi: 10.1128/JVI.01225-07.

Kawano et al.: An experimental and computational evolution-based method to study a mode of co-evolution of overlapping open reading frames in the AAV2 viral genome. PLoS One. 8(6):e66211 (2013) doi: 10.1371/journal.pone.0066211.

Kay et al.: Looking into the safety of AAV vectors. Nature. 424(6946):251 (2003) doi: 10.1038/424251b.

Kotchey et al.: A potential role of distinctively delayed blood clearance of recombinant adeno-associated virus serotype 9 in robust cardiac transduction. Mol Ther. 19(6):1079-89 (2011) doi: 10.1038/mt.2011.3.

Kotterman et al. Engineering adeno-associated viruses for clinical gene therapy. Nature reviews Genetics 15:445-451 (2014).

(56) References Cited

OTHER PUBLICATIONS

Manno et al.: Successful transduction of liver in hemophilia by AAV-Factor IX and limitations imposed by the host immune response. Nature Medicine. 12(3):342-347 (2006).
McCaffrey et al.: The host response to adenovirus, helper-dependent adenovirus, and adeno-associated virus in mouse liver. Mol Ther. 16(5):931-41 (2008) doi: 10.1038/mt.2008.37.
Nakai et al.: A limited number of transducible hepatocytes restricts a wide-range linear vector dose response in recombinant adeno-associated virus-mediated liver transduction. J Virol. 76(22):11343-9 (2002) doi: 10.1128/jvi.76.22.11343-11349.2002.
Nakai et al.: AAV serotype 2 vectors preferentially integrate into active genes in mice. Nat Genet. 34(3):297-302 (2003) doi: 10.1038/ng1179.
Nakai et al.: Helper-independent and AAV-ITR-independent chromosomal integration of double-stranded linear DNA vectors in mice. Mol Ther. 7(1):101-11 (2003) doi: 10.1016/s1525-0016(02)00023-0.
Ohashi et al.: Modified infusion procedures affect recombinant adeno-associated virus vector type 2 transduction in the liver. Hum Gene Ther. 16(3):299-306 (2005) doi: 10.1089/hum.2005.16.299.
Parvoviridae an overview. ScienceDirect. (20003).
PCT/US2020/016273 International Preliminary Report on Patentability dated Aug. 12, 2021.
PCT/US2020/016273 International Search Report and Written Opinion dated Jun. 23, 2020.
Powers et al.: A Quantitative Dot Blot Assay for AAV Titration and Its Use for Functional Assessment of the Adeno-associated Virus Assembly-activating Proteins. J Vis Exp. (136):56766 (2018). doi: 10.3791/56766.
U.S. Appl. No. 17/337,341 Office Action dated Feb. 1, 2022.
Wang et al.: AAV vectors containing rDNA homology display increased chromosomal integration and transgene persistence. Mol Ther. 20(10):1902-11 (2012) doi: 10.1038/mt.2012.157.
Yu et al.: Intraganglionic AAV6 results in efficient and long-term gene transfer to peripheral sensory nervous system in adult rats. PLoS One. 8(4):e61266 (2013) doi: 10.1371/journal.pone.0061266.
U.S. Appl. No. 18/160,796 Office Action dated Aug. 2, 2023.
U.S. Appl. No. 18/160,796 Office Action dated Nov. 13, 2023.

* cited by examiner

Anti-GFP

GFP      Anti-HuC/D

6. Recover and sequence hSynI-driven transcripts

ATGGCTGCCGATGGTTATCTTCCAGATTGGCTCGAGGACAACCTTAGTGAAGG
AATTCGCGAGTGGTGGGCTTTGAAACCTGGAGCCCCTCAACCCAAGGCAAATC
AACAACATCAAGACAACGCTCGAGGTCTTGTGCTTCCGGGTTACAAATACCTTG
GACCCGGCAACGGACTCGACAAGGGGGAGCCGGTCAACGCAGCAGACGCGG
CGGCCCTCGAGCACGACAAGGCCTACGACCAGCAGCTCAAGGCCGGAGACAA
CCCGTACCTCAAGTACAACCACGCCGACGCCGAGTTCCAGGAGCGGCTCAAAG
AAGATACGTCTTTTGGGGGCAACCTCGGGCGAGCAGTCTTCCAGGCCAAAAAG
AGGCTTCTTGAACCTCTTGGTCTGGTTGAGGAAGCGGCTAAGACGGCTCCTGG
AAAGAAGAGGCCTGTAGAGCAGTCTCCTCAGGAACCGGACTCCTCCGCGGGTA
TTGGCAAATCGGGTGCACAGCCCGctaaaaagagactcaatttcggtcagactggcgacacagag
tcagtcccagaccctcaaccaatcggagaacctcccgcagcccctcaggtgtgggatctcttacaatggcttcaggt
ggtggcgcaccagtggcagacaataacgaaggtgccgatggagtgggtagttcctcgggaaattggcattgcgattc
ccaatggctggggacagagtcatcaccaccagcacccgaacctgggccctgcccacctacaacaatcacctcta
caagcaaatctccaacagcacatctggaggatcttcaaatgacaacgcctacttcggctacagcacccctgggggt
attttgacttcaacagattccactgccacttctcaccacgtgactggcagcgactcatcaacaacaactggggattccg
gcctaagcgactcaacttcaagctcttcaacattcaggtcaaagaggttacggacaacaatggagtcaagaccatcg
ccaataaccttaccagcacggtccaggtcttcacggactcagactatcagctcccgtacgtgctcgggtcggctcacg
agggctgcctcccgccgttcccagcggacgttttcatgattcctcagtacgggtatctgacgcttaatgatggaagcca
ggccgtgggtcgttcgtccttttactgcctggaatatttccgtcgcaaatgctaagaacgggtaacaacttccagttcag
ctacgagtttgagaacgtacctttccatagcagctacgctcacagccaaagcctggaccgactaatgaatccactcat
cgaccaatacttgtactatctctcaaagactattaacggttctggacagaatcaacaaacgctaaaattcagtgtggcc
ggacccagcaacatggctgtccagggaagaaactacatacctggacccagctaccgacaacaacgtgtctcaacc
actgtgactcaaaacaacaacagcgaatttgcttggcctggagcttcttcttgggctctcaatggacgtaatagcttgat
gaatcctggacctgctatggccagccacaaagaaggagaggaccgttctttcctttgtctggatctttaattttttggcaa
acaaggaactggaagagacaacgtggatgcggacaaagtcatgataaccaacgaagaagaaattaaaactact
aacccggtagcaacggagtcctatggacaagtggccacaaaccaccagagtgcccaagcacaggcgcagaccg
gctgggttcaaaaccaaggaatacttccgggtatggtttggcaggacagagatgtgtacctgcaaggacccatttggg
ccaaaattcctcacacggacggcaacttcaccctctccgctgatgggagggtttggaatgaagcacccgcctcctc
agatcctcatcaaaaacacacctgtacctgcggatcctccaacggccttcaacaaggacaagctgaactctttcatca
cccagtattctactggccaagtcagcgtggagatcgagtgggagctgcagaaggaaaacagcaagcgctggaac
ccggagatccagtacacttccaactattacaagtctaataatgttgaatttgctgttaatactgaaggtgtatatagtgaac
cccgccccattggcaccagatacCTGACTCGTAATCTGTAA

FIG. 5

Splice acceptor

Splice acceptor

Splice acceptor

T (A in antisense)-rich region

Exon CT――intron――AC Exon anti-sense mRNA of AAV cap genes

Splice donor

T (A in antisense)-rich region
anti-sense mRNA of AAV cap genes

Splice donor anti-sense mRNA of AAV cap genes

FIG. 6F

ATGGCTGCTGACGGTTATCTTCCAGATTGGCTCGAGGACAACCTTTCTGAAGGC
ATTCGTGAGTGGTGGGCTCTGAAACCTGGAGTCCCTCAACCCAAAGCGAACCA
ACAACACCAGGACAACCGTCGGGGTCTTGTGCTTCCGGGTTACAAATACCTCG
GACCCGGTAACGGACTCGACAAAGGAGAGCCGGTCAACGAGGCGGACGCGGC
AGCCCTCGAACACGACAAAGCTTACGACCAGCAGCTCAAGGCCGGTGACAACC
CGTACCTCAAGTACAACCACGCCGACGCCGAGTTTCAGGAGCGTCTTCAAGAA
GATACGTCTTTTGGGGGCAACCTTGGCAGAGCAGTCTTCCAGGCCAAAAAGAG
GATCCTTGAGCCTCTTGGTCTGGTTGAGGAAGCAGCTAAAACGGCTctggaaaga
agaggcctgtagatcagtctcctcaggaaccggactcatcatctggtgttggcaaatcgggcaaacagcctgccaga
aaaagactaaatttcggtcagactggcgactcagagtcagtccagaccctcaacctctcggagaaccaccagcag
cccccacaagtttgggatctaatacaatggcttcaggcggtggcgcaccaatggcagacaataacgagggtgccga
tggagtgggtaattcctcaggaaattggcattgcgattcccaatggctgggcgacagagtcatcaccaccagcacca
gaacctgggccctgcccacttacaacaaccatctctacaagcaaatctccagccaatcaggagcttcaaacgacaa
ccactactttggctacagcacccttgggggtattttgactttaacagattccactgccacttctcaccacgtgactggca
gcgactcattaacaacaactggggattccggcccaagaaactcagcttcaagctcttcaacatccaagttaaagagg
tcacgcagaacgatggcacgacgactattgccaataaccttaccagcacggttcaagtgtttacggactcggagtatc
agctcccgtacgtgctcgggtcggcgcaccaaggctgtctccgccgtttccagcggacgtcttcatggtccctcagtat
ggatacctcaccctgaacaacggaagtcaagcggtgggacgctcatcctttactgcctggagtacttcccttcgcaga
tgctaaggactggaaataacttccaattcagctataccttcgaggatgtacctttcacagcagctacgctcacagcca
gagtttggatcgcttgatgaatcctcttattgatcagtatctgtactacctgaacagaacgcaaggaacaacctctggaa
caaccaaccaatcacggctgcttttagccaggctgggcctcagtctatgtctttgcaggccagaaattggctacctgg
gccctgctaccggcaacagagactttcaaagactgctaacgacaacaacaacagtaactttccttggacagcggcc
agcaaatatcatctcaatggccgcgactcgctggtgaatccaggaccagctatggccagtcacaaggacgatgaag
aaaaattttccctatgcacggcaatctaatatttggcaaagaagggacaacggcaagtaacgcagaattagataat
gtaatgattacggatgaagaagagattcgtaccaccaatcctgtggcaacagagcagtatggaactgtggcaaata
acttgcagagctcaaatacagctcccacgactagaactgtcaatgatcaggggcccttacctggcatggtgtggcaa
gatcgtgacgtgtaccttcaaggacctatctgggcaaagattcctcacacggatggacactttcatccttctcctctgatg
ggaggctttggactgaaacatccgcctcctcaaatcatgatcaaaaatactccggtacCGGCAAATCCTCC
GACGACTTTCAGCCCGGCCAAGTTTGCTTCATTTATCACTCAGTACTCCACTGG
ACAGGTCAGCGTGGAAATTGAGTGGGAGctacagaaagaaaacagcaaacgttggaatccag
agattcagtacacttccaactacaacaagtctgttaatgtggactttactgtagacactaatggtgtttatagtgaacctcg
ccctattggaacccggtatctcacACGAAACTTGTAA ATGGCTGCTGACGGTTATCTTCCAGATTGGCTCGAGGACAACCTTTCTGAAGGC
ATTCGTGAGTGGTGGGCTCTGAAACCTGGAGTCCCTCAACCCAAAGCGAACCA
ACAACACCAGGACAACCGTCGGGGTCTTGTGCTTCCGGGTTACAAATACCTCG
GACCCGGTAACGGACTCGACAAAGGAGAGCCGGTCAACGAGGCGGACGCGGC
AGCCCTCGAACACGACAAAGCTTACGACCAGCAGCTCAAGGCCGGTGACAACC
CGTACCTCAAGTACAACCACGCCGACGCCGAGTTTCAGGAGCGTCTTCAAGAA
GATACGTCTTTTGGGGGCAACCTTGGCAGAGCAGTCTTCCAGGCCAAAAAGAG
GATCCTTGAGCCTCTTGGTCTGGTTGAGGAAGCAGCTAAAACGGCTCctggaaaga
agaggcctgtagatcagtctcctcaggaaccggactcatcatctggtgttggcaaatcgggcaaacagcctgccaga
aaaagactaaatttcggtcagactggcgactcagagtcagtcccagaccctcaacctctcggagaaccaccagcag
ccccacaagtttgggatctaatacaatggcttcaggcggtggcgcaccaatggcagacaataacgagggtgccga
tggagtgggtaattcctcaggaaattggcattgcgattcccaatggctgggcgacagagtcatcaccaccagcacca
gaacctgggccctgcccacttacaacaaccatctctacaagcaaatctccagccaatcaggagcttcaaacgacaa
ccactactttggctacagcaccccttggggtatttgactttaacagattccactgccacttctcaccacgtgactggca
gcgactcattaacaacaactggggattccggcccaagaaactcagcttcaagctcttcaacatccaagttaaagagg
tcacgcagaacgatggcacgacgactattgccaataaccttaccagcacggttcaagtgtttacggactcggagtatc
agctcccgtacgtgctcgggtcggcgcaccaaggctgtctccgccgtttccagcggacgtcttcatggtccctcagtat
ggatacctcaccctgaacaacggaagtcaagcggtgggacgctcatccttttactgcctggagtacttcccttcgcaga
tgctaaggactggaaataacttccaattcagctataccttcgaggatgtaccttttcacagcagctacgctcacagcca
gagtttggatcgcttgatgaatcctcttattgatcagtatctgtactacctgaacagaacgcaaggaacaacctctggaa
caaccaaccaatcacggctgcttttagccaggctgggcctcagtctatgtctttgcaggccagaaattggctacctgg
gccctgctaccggcaacagagactttcaaagactgctaacgacaacaacagtaactttccttggacagcggcc
agcaaatatcatctcaatggccgcgactcgctggtgaatccaggaccagctatggccagtcacaaggacgatgaag
aaaaatttttccctatgcacggcaatctaatatttggcaaagaagggacaacggcaagtaacgcagaattagataat
gtaatgattacggatgaagaagagattcgtaccaccaatcctgtggcaacagagcagtatggaactgtggcaaata
acttgcagagctcaaatacagctcccacgactagaactgtcaatgatcaggggggccttacCTGGCATGGTGT
GGCAAGATCGTGACGTGTACCTTCAAGGACCTATCTGGGCAAAGATTCCTCACA
CGGATGGACACTTTCATCCTTCTCCTCTGATGGGAGGCTTTGGACTGAAACATC
CGCCTCCTCAAATCATGATCAAAATACTCCGGTACCGGCAAATCCTCCGACGA
CTTTCAGCCCGGCCAAGTTTGCTTCATTTATCACTCAGTACTCCACTGGACAGG
TCAGCGTGGAAATTGAGTGGAGctacagaaagaaaacagcaaacgttggaatccagagattcag
tacacttccaactacaacaagtctgttaatgtggactttactgtagacactaatggtgtttatagtgaacctcgccctattg
gaacccggtatctcacACGAAACTTGTAA

FIG. 7B

Splice acceptor

T (A in antisense)-rich region

Exon | CT ———— intron anti-sense mRNA of AAV cap genes

Splice acceptor

T (A in antisense)-rich region

| Exon | CT —— intron —— | anti-sense mRNA of AAV cap genes

Splice donor anti-sense mRNA of AAV cap genes

FIG. 9B

Splice donor anti-sense mRNA of AAV cap genes atggctgccgatggttatcttccagattggctcgaggacaacctctctgagggcattcgcgagtggtgggacttgaaac
ctggagccccgaagcccaaagccaaccagcaaaagcaggacgacggccggggtctggtgcttcctggctacaag
tacctcggacccttcaacggactcgacaaggggagcccgtcaacgcggcggacgcagcggccctcgagcacg
acaaggcctacgaccagcagctcaaagcgggtgacaatccgtacctgcggtataaccacgccgacgccgagtttc
aggagcgtCTgcaagaagatacgtcttttgggggcaacctcgggcgagcagtcttccaggccaagaagcgggttc
tcgaacctctcggtctggttgaggaaggcgctaagacggctcCTggaaagaaacgtccggtagagcagtcgccac
aagagccagactcctcctcgggcatcggcaagacaggccagcagcccgCTaaaaagagactcaattttggtcag
actggcgactcagagtcagtccccgatccacaacctctcggagaacctccagcaaccccgctgctgtgggaccta
ctacaatggcttcaggcggtggcgcaccaatggcagacaataacgaaggcgccgacggagtgggtaatgcctcag
gaaattggcattgcgattccacatggctgggcgacagagtcatcaccaccagcacccgcacctgggccttgcccac
ctacaataaccacctctacaagcaaatctccagtgcttcaacggggccagcaacgacaaccactacttcggctac
agcacccctgggggtattttgatttcaacagattccactgccacttttcaccacgtgactggcagcgactcatcaacaa
caattggggattccggcccaagagactcaacttcaaactcttcaacatccaagtcaaggaggtcacgacgaatgatg
gcgtcacaaccatcgctaataaccttACcagcacggttcaagtcttctcggactcggagtaccagcttccgtacgtcct
cggctctgcgcaccagggctgcctccctccgttcccggcggacgtgttcatgattccgcaatacggctacctgacgctc
aacaatggcagccaagccgtgggacgttcatccttttactgcCTggaatatttcccttctcagatgctgagaacgggc
aacaactttACcttcagctacacctttgaggaagtgcctttccacagcagctacgcgcacagccagagcctggaccg
gctgatgaatcctctcatcgaccaatacctgtattACCTgaacagaactcaaaatcagtccggaagtgcccaaaac
aaggacttgctgtttagccgtgggtctccagctggcatgtctgttcagcccaaaaactggctACctggaccctgttatcg
gcagcagcgcgtttCTaaaacaaaaacagacaacaacaacagcaattttACctggactggtgcttcaaaatataa
cctcaatgggcgtgaatccatcatcaaccctggcactgctatggcctcacacaaagacgacgaagacaagttctttcc
catgagcggtgtcatgattttggaaaagagagcgccggagcttcaaacaCTgcattggacaatgtcatgattacag
acgaagaggaaattaaagccactaaccctgtggccaccgaaagatttgggaccgtggcagtcaatttccagagca
gcagcacagaccctgcgaccggagatgtgcatgctatgggagcattACctggcatggtgtggcaagatagagacg
tgtACctgcagggtcccatttgggccaaaattcctcacacagatggacactttcacccgtctcctcttatgggcggcttt
ggactcaagaacccgcctcctcagatcctcatcaaaaacacgcctgttcctgcgaatcctccggcggagttttcagct
acaaagtttgcttcattcatcacccaatactccacaggacaagtgagtgtggaaattgaatgggagCTgcagaaag
aaaacagcaagcgctggaatcccgaagtgcagtacacatccaattatgcaaaatctgccaacgttgattttactgtgg
acaacaatggactttatactgagcctcgcccccattggcacccgttACcttACccgtcccctgtaa

METHODS FOR USING
TRANSCRIPTION-DEPENDENT DIRECTED
EVOLUTION OF AAV CAPSIDS

RELATED CASES

This application is a continuation of U.S. patent application Ser. No. 17/822,111, filed on Aug. 24, 2022, and entitled "METHODS FOR USING TRANSCRIPTION-DEPENDENT DIRECTED EVOLUTION OF AAV CAPSIDS," which is a continuation of U.S. patent application Ser. No. 17/337,341, filed on Jun. 2, 2021 (now U.S. Pat. No. 11,459,558, issued on Oct. 4, 2022), and entitled "METHODS FOR USING TRANSCRIPTION-DEPENDENT DIRECTED EVOLUTION OF AAV CAPSIDS," which is a continuation of International Patent Application No. PCT/US2020/016273 filed on Jan. 31, 2020, and entitled "METHODS FOR USING TRANSCRIPTION-DEPENDENT DIRECTED EVOLUTION OF AAV CAPSIDS," which claims priority to U.S. Provisional Patent Application No. 62/799,603, filed on Jan. 31, 2019, and entitled "TRANSCRIPTION-DEPENDENT DIRECTED EVOLUTION OF AAV CAPSIDS," each of which are hereby incorporated by reference in their entireties.

STATEMENT REGARDING FEDERALLY
SPONSORED RESEARCH

This invention was made with government support under Grant No. NS088399 awarded by the National Institutes of Health/National Institute of Neurological Disorders and Stroke. The government has certain rights in the invention.

SEQUENCE LISTING

The instant application contains a Sequence Listing which has been submitted electronically in XML format and is hereby incorporated by reference in its entirety. Said XML copy, created on Apr. 17, 2023, is named 60255701304_2.xml and is 521,686 bytes in size.

TECHNICAL FIELD

This disclosure relates to viral vectors used in gene delivery. More specifically, this disclosure relates to a method for transcription-dependent directed evolution and adeno-associated virus ("AAV") vectors that are selected by using this method.

BACKGROUND

Recombinant adeno-associated virus ("AAV") vectors are among the most promising for in vivo gene delivery. The usefulness of AAV vectors has been expanded since a number of naturally occurring new serotypes and subtypes were isolated from human and non-human primate tissues. Gao et al., *J Virol* 78, 6381-6388 (2004) and Gao et al., *Proc Natl Acad Sci USA* 99, 11854-11859 (2002). Among the newly-identified AAV isolates, AAV serotype 8 (AAV8) and AAV serotype 9 (AAV9) have gained attention because AAV vectors derived from these two serotypes can transduce a variety of organs including the liver, heart, skeletal muscles and central nervous system with high efficiency following systemic administration. Ghosh et al., *Mol Ther* 15, 750-755 (2007); Pacak et al., *Circ Res* 99, 3-9 (2006); Inagaki et al., *Mol Ther* 14, 45-53 (2006); Zhu et al., *Circulation* 112, 2650-2659(2005); Wang et al., *Nat Biotechnol* 23, 321-328 (2005); Nakai et al., *J Virol* 79, 214-224 (2005); and Foust et al., *Nature Biotechnol* 23, 321-328 (2009). This robust transduction by AAV8 and 9 vectors has been ascribed to strong tropism for these cell types, efficient cellular uptake of vectors, and/or rapid uncoating of virion shells in cells. Thomas et al., *J Virol* 78, 3110-3122 (2004). In addition, emergence of capsid-engineered AAV vectors with better performance has significantly broadened the utility of AAV as a vector toolkit. Asokan et al., *Mol Ther* 20, 699-708 (2012).

A proof-of-concept using AAV-mediated gene therapy has been shown in many preclinical animal models of human diseases. Phase I/II clinical studies have shown promising results for the treatment for hemophilia B (Nathwani et al., *N Engl J Med* 71, 1994-2004 (2014)), lipoprotein lipase deficiency (Carpentier et al., *J Clin Endocrinol Metab* 97, 1635-1644 (2012)), Leber congenital amaurosis (Jacobson et al., *Arch Ophthalmol* 130, 9-24 (2012) and Pierce and Bennett, *Cold Spring Harb Perspect Med* 5, a017285 (2015)), among others (reviewed in Mingozzi and High, *Nat Rev Genet* 12, 341-355 (2011) and Wang et al., *Nat Rev Drug Discov* 18, 358-378 (2019)).

Despite this promise, human studies have also revealed unexpected issues and potential challenges in AAV-mediated gene therapy. Manno et al., *Nat Med* 12, 342-347 (2006). In addition, despite rapid progress in our understanding of AAV biology and capsid-phenotype relationships (Adachi et al., *Nat Commun* 5, 3075, (2014); Grimm et al., *Hum Gene Ther* 28, 1075-1086, (2017); and Ogden et al., *Science* 366, 1139-1143, (2019)), there remain many desirable properties for clinical AAV vectors that we cannot rationally design.

To this end, high throughput screening methods for identifying novel AAV capsids with such desirable phenotypes have been employed. In particular, the development of in vivo AAV library selection strategies have produced a variety of designer AAV variants capable of highly efficient transduction of previously refractory cell types (reviewed in Kotterman and Schaffer, *Nat Rev Genet* 15, 445-451 (2014) and Grimm et al., *Mol Ther* 23, 1819-1831 (2015)).

The earliest attempts at in vivo library selection (1st Generation) relied on recovery of vector genome DNA from dissected tissue. Theoretically, this strategy results in recovery of both effective AAV variants, as well as AAV variants that mediate some, but not all of the steps required for vector-mediated transgene expression (FIG. 1). Thus, screening a diverse library of synthetic AAV variants potentially leads to a high background recovery of AAV variants that are completely ineffective gene therapy vectors. Furthermore, targeting a specific cell type requires further processing, such as fluorescence-activated cell sorting or laser capture microdissection. Nonetheless, there have been several reports of successfully employing this technology. Excoffon et al., *Proc Nat/Acad Sci USA* 106, 3865-3870 (2009); Grimm et al., *J Virol* 82, 5887-5911 (2008); Lisowski et al., *Nature* 506, 382-386 (2014); and Dalkara et al., *Sci Transl Med* 5, 189ra176 (2013). However, a landmark study in 2016 by Deverman et al. showed that this process could be greatly improved upon by using a Cre-dependent selection strategy (2nd Generation). Deverman et al., *Nat Biotechnol* 34, 204-209 (2016). Cre-dependent library selection takes advantage of the selective ability of Cre recombinase to act on double-stranded DNA, but not single-stranded DNA, in order to invert vector genome DNA containing a primer binding sequence. Inversion of this sequence allows for direction-selective PCR to specifically amplify viral DNA delivered to cells by AAV variants that are able to undergo the late stage of transduction at which double stranded DNA is formed from single-stranded AAV genomes. In addition, the use of Cre driver lines facilitates selective expression of Cre recombinase in a cell type-specific manner, allowing for selection of novel AAV variants that efficiently transduce. Indeed, the use of Cre-dependent selection allowed the authors to develop an AAV9 variant, AAV-PHP.B, that is capable of 40 times greater transduction than the parental AAV9 following systemic administration in C57BL/6J mice. Deverman et al., *Nat Biotechnol* 34, 204-209 (2016). Unfortunately, it has recently become clear that the enhancement exhibited by AAV-PHP.B in mice does not translate to the non-human primate context (Matsuzaki et al. 2018 and Hordeaux et al. 2019). Surprisingly, the enhancement does not even extend to all commonly used mouse strains (Matsuzaki et al. 2018 and Hordeaux et al. 2019). There is, therefore, a strong impetus to accelerate the development of clinically relevant AAV vectors by performing AAV library selection experiments in primate models. However, unlike the AAV variant selection in mice where a plethora of cell type-specific transgenic Cre driver lines are already established, Cre-dependent selection is not tractable in clinically relevant large animals, including non-human primates, because Cre transgenic animals are not readily available.

We therefore sought to develop a next-generation selection strategy (3rd Generation) with similar or better selective stringency as that provided by Cre-dependent selection, but without the need for Cre recombinase. In order to accomplish this goal, we developed the TRAnscription-dependent Directed Evolution system, or TRADE. In the transcription-dependent selection, we express the AAV cap gene as a non-coding antisense mRNA driven by a cell type-specific enhancer-promoter. Recovery of this antisense transcript by RT-PCR allows for stringent recovery of AAV cap genes at the level of vector-mediated mRNA expression in a specific cell type without the use of Cre recombinase. Targeting of different cell types merely requires cloning of a different cell type-specific enhancer-promoter into the plasmid construct. Thus, TRADE is a highly flexible system that can be applied in a wide variety of contexts, including the non-human primate context for development of enhanced AAV vectors for clinical gene therapy. Note that the same principle can be used for expressing AAV cap gene in an sense orientation. However, the sense strand approach results in expression of immunogenic capsid proteins in target cells and is therefore less ideal than the antisense strand approach employed by the TRADE system.

SUMMARY

This disclosure provides a next-generation directed evolution strategy, termed TRAnscription-dependent Directed Evolution ("TRADE"), that selects for AAV capsid transduction at the level of cell type-specific or ubiquitous mRNA expression. The method described herein provides the following advantages over Cre recombination-based AAV targeted evolution ("CREATE"), the most contemporary methods for AAV capsid directed evolution reported in the literature. Deverman et al., *Nat Biotech* 34, 204-209 (2016). First, the CREATE system requires Cre expression, which can be attained either by exogenously-delivered Cre expression or by the use of Cre-transgenic animals. In contrast, the TRADE system does not require Cre-transgenic animals; therefore, it can be applied to animals and cultured cells derived from any animal species and can be readily adapted to large animals, including non-human primates. Second, unlike the CREATE system, in which the cell-type specific selection is applied at the level of AAV viral genome conversion from single-stranded DNA to double-stranded DNA, TRADE allows for cell type-specific selection at the level of AAV genome transcription. Therefore, the TRADE system can provide greater selective pressure than the CREATE system. Third, multiple directed evolution schemes (e.g., neuron-specific, astrocyte-specific, oligodendrocyte-specific, and microglia-specific) can be integrated into one AAV capsid library and selection for AAV vectors targeting each cell type can be performed in a single animal. Fourth, any cell type-specific or tissue/organ-specific enhancers/promoters or ubiquitous enhancers/promoters can be readily used for AAV capsid directed evolution aimed at identification of cell type-specific or ubiquitous novel AAV capsids with enhanced potency. Fifth, the TRADE methodology is not limited to the genus Dependoparvovirus, including the common AAVs that have been used for gene delivery, but can also be applied more broadly to the family Parvoviridae, including in the genera Bocaparvoviruses and Erythroparvoviruses other than AAV (e.g., bocaviruses), and even more broadly to an DNA virus.

This disclosure also provides novel AAV capsid mutants. TRADE technology was used to identify novel AAV vectors that mediate neuronal transduction in the brain following intravenous administration. Application of TRADE in C57BL/6J mice and a rhesus macaque resulted in the identification of new AAV capsids that can transduce neurons more efficiently and more specifically than AAV9 in the mouse and non-human primate brain following intravenous administration. In addition, we identified a novel AAV capsid that can transduce an undefined cell population or populations, that reside in the lung and are potentially of neuronal origin, 5 to 18 times better than the AAV9.

The present disclosure also provides a method to prevent splicing of antisense mRNA of the AAV capsid gene. Antisense pre-mRNA transcribed from the AAV cap gene open reading frame ("ORF") can be spliced making (a) truncated mRNA species. To our knowledge, this is a new discovery that has never previously been reported. Such splicing has the potential to hinder effective recovery of full-length antisense mRNA of the AAV cap ORF, which is essential for TRADE when a wide region of the cap ORF is mutagenized. This disclosure provides a novel strategy to prevent splicing of antisense mRNA of the cap gene.

The TRADE system described herein uses antisense mRNA to recover capsid sequence information, TRADE using sense strand mRNA (i.e., sense strand TRADE) is also feasible using the same principle. However, it should be noted that the sense strand TRADE approach results in expression of immunogenic capsid proteins in target cells and therefore is presumably less ideal than the antisense strand approach.

BRIEF DESCRIPTION OF THE FIGURES

(FIG. 2A) A map of the AAV vector genome in a TRADE configuration (AAV-TRADE). A cell type-specific enhancer-promoter is placed in an antisense orientation to drive AAV cap gene transcription expression as antisense mRNA. A polyadenylation signal (pA) derived from the simian virus 40 (SV40) genome is placed within the AAV genome intron in an antisense orientation to terminate antisense AAV cap gene mRNA transcription. The eGFP open-reading frame (ORF) can be placed as depicted to serve as a reporter or facilitate enrichment of transduced cells by FACS; however, such a marker gene is not strictly necessary for TRADE. A ubiquitous promoter such as the CAG promoter can be also used in TRADE in placed of cell type-specific enhancers-promoters to identify AAV capsids that can transduce a variety of cell types. A cell type-specific enhancer-promoter can be placed upstream of the AAV cap gene ORF to drive expression of the AAV cap gene mRNA transcripts in a sense orientation (i.e., sense strand TRADE). However, this approach may not be ideal for TRADE because AAV capsid protein would be expressed in target cells, which may result in undesired biological consequences in the directed evolution process. (FIG. 2B) During AAV vector production in HEK293 cells, and in the presence of the adenoviral helper functions, the AAV2 viral p40 promoter drives cap gene expression (forward transcription) and cell type-specific transcripts are suppressed, leading to successful production of recombinant AAV vectors containing the AAV-TRADE vector genome. Following transduction of a specific cell type, the cell type-specific enhancer-promoter is activated, driving expression of eGFP and the antisense cap mRNA sequence, while the transcriptional activity of the p40 promoter remains inactive in transduced cells due to a lack of adenoviral helper functions. The entire cap gene ORF can be recovered by reverse transcription (RT)-PCR using antisense cap gene mRNA as a template that is expressed in a cell type-specific manner. We have observed that recombinant AAV vectors can be produced successfully at high levels even in the presence of antisense mRNA transcripts expressed due to leaky expression from the human synapsin I gene (hSynI) enhancer-promoter in HEK293 cells. We have also observed that recombinant AAV vectors can be produced successfully at high titers even when we use the CAG promoter that drives expression of antisense AAV cap mRNA transcripts at high levels.

(FIG. 3A) A map of the AAV-PHP.B-hSynI-GFP-TRADE vector genome. (FIG. 3B) To verify the TRADE system, this AAV vector genome was packaged into the AAV-PHP.B capsid as a single-stranded DNA genome and the resulting AAV vector was injected into two 8-week-old C57BL/6J mice intravenously at a dose of $3\times10^{11}$ vector genomes (vg) per mouse. Brain tissue was harvested 12 days post-injection. The brain tissue from one animal was fixed with 4% paraformaldehyde and used for immunofluorescence microscopy and the brain tissue from the other animal was unfixed and used for molecular analysis of AAV vector genome DNA and RNA. (FIG. 3C) Immunofluorescence microscopy image of brain sections stained with anti-GFP antibody confirmed expression of the cell type-specific enhancer-promoter-driven transcript. (FIG. 3D) hSynI enhancer-promoter-driven GFP expression was observed specifically in neurons (anti-HuC/D+). (FIG. 3E) RT-PCR was used to recover the full-length cap ORF sequence (RT+). RT−, a no reverse transcriptase control; Plas, a positive control obtained with DNA-PCR using a plasmid template containing the AAV-PHP.B-hSynI-GFP-TRADE vector genome sequence; NT, a no template PCR control. (FIG. 3F) Sanger sequencing of the RT-PCR product revealed expected splicing of the MVM intron in the antisense transcripts expressed by the hSynI enhancer-promoter (SEQ ID NO:190). The exon-exon junction is highlighted with gray. (FIG. 3G) Sanger sequencing confirmed the insertion of the PHP.B peptide (highlighted with gray) (SEQ ID NO:191).

FIG. 5 An intron identified in antisense mRNA derived from the AAV9 cap gene (SEQ ID NO:192). When the AAV-PHP.B cap gene sequence was transcribed in an antisense orientation in HEK293 cells or Neuro2a cells under the control of the neuron-specific human synapsin I (hSynI) enhancer-promoter, a splicing event was identified with cryptic splice donor and splice acceptor sites (please refer to FIGS. 6A-6F as well). The underlined sequence indicates the intron found within the AAV9 cap ORF. This splicing event was not observed in mouse brain neurons. It should be noted that (1) although the hSynI enhancer-promoter has been used as a neuron-specific element, it has been shown to drive leaky expression in HEK293 cells; and (2) the AAV9 cap ORF sequence used for the intron splicing experiment had the following silent mutations near the C-terminus:

Figure 1:
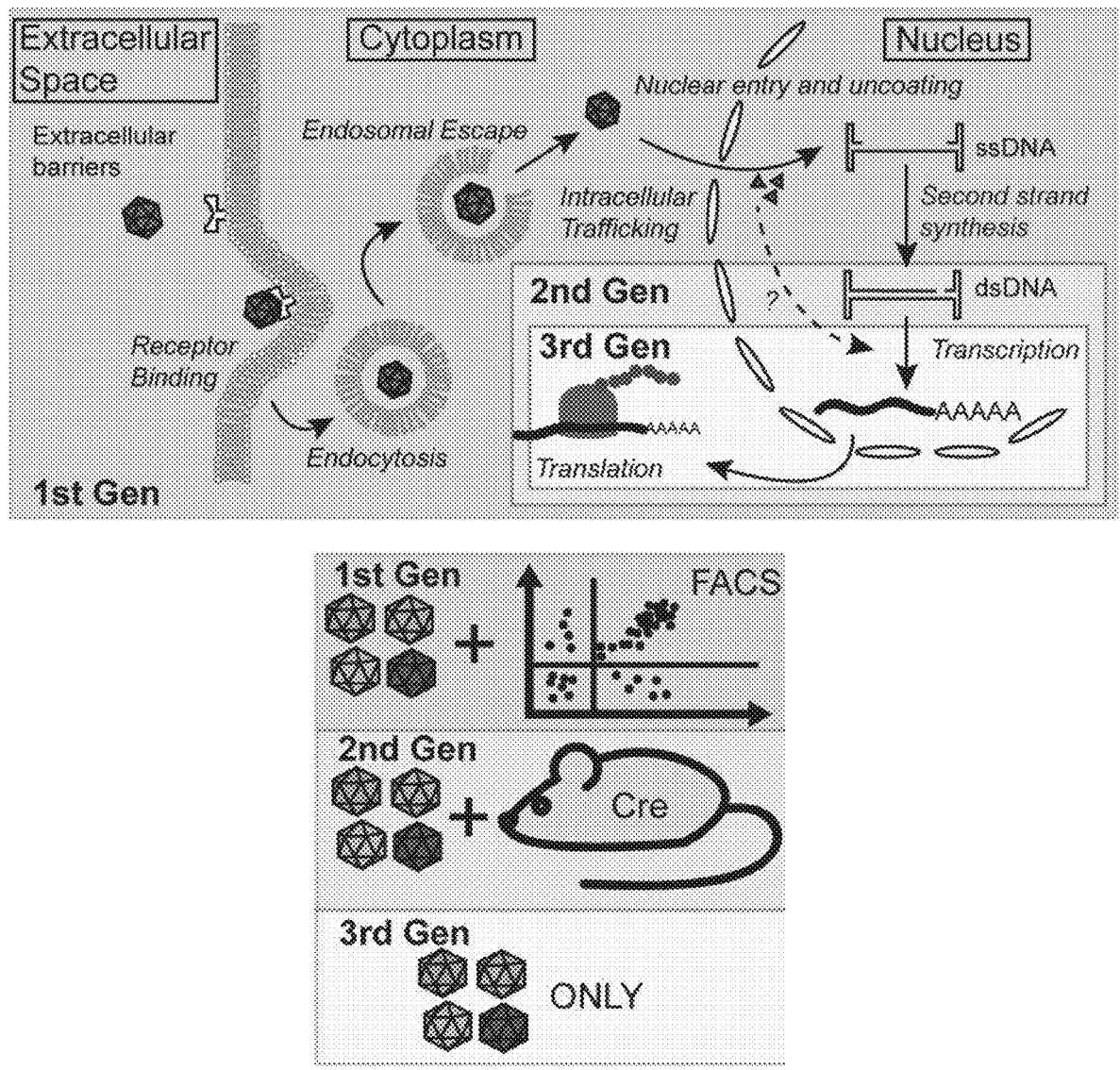
FIG. 1 An overview of in vivo library selection strategies utilized for directed evolution of the AAV capsid. AAV vector-mediated transduction is a multi-step process that requires the virion to overcome extracellular barriers, bind receptors on the target cell, enter the cell via endocytosis, escape the endosome, traffic to the nucleus, uncoat, achieve a double-stranded DNA configuration, and finally undergo transcription/translation. The earliest strategies for in vivo library selection (1st Gen) recovered all vector genome DNA from a tissue sample. Theoretically, this strategy would recover both effective AAV variants, as well as AAV variants that mediate some, but not all of the steps required for vector-mediated transgene expression. In addition, this strategy would also recover AAV vector genome DNA from AAV vector particles that do not enter cells and stay in the extracellular matrix. Thus, screening a diverse library of synthetic AAV variants would lead to a relatively high background recovery of AAV variants that are completely ineffective gene therapy vectors. Furthermore, focusing on a specific cell type requires further processing, such as fluorescence-activated cell sorting (FACS) or laser capture microdissection (LCM). The second generation of library selection ($2^{nd}$ Gen) substantially increased selection stringency by utilizing Cre-dependent recovery of only those AAV variants that are able to achieve the double-strand DNA stage of transduction. Furthermore, driving the expression of Cre with a cell type-specific enhancer-promoter allows for targeting of a specific cell type while retaining the benefits of processing bulk tissue samples. The third generation of library selection ($3^{rd}$ Gen) further builds on AAV directed evolution technology by employing transcription-dependent recovery of AAV variants that are able to mediate transgene mRNA expression from a cell type-specific enhancer-promoter, without the requirement of Cre expression.

(SEQ ID NO: 1)
gaacccccgccccattggcacGCgTtacCTGACTCGTAATCTGTAA.

The intron sequence is underlined, and the silent mutations that have been introduced into the intron to create an MluI (ACGCGT) recognition site are indicated in uppercase.

Figure 6F:
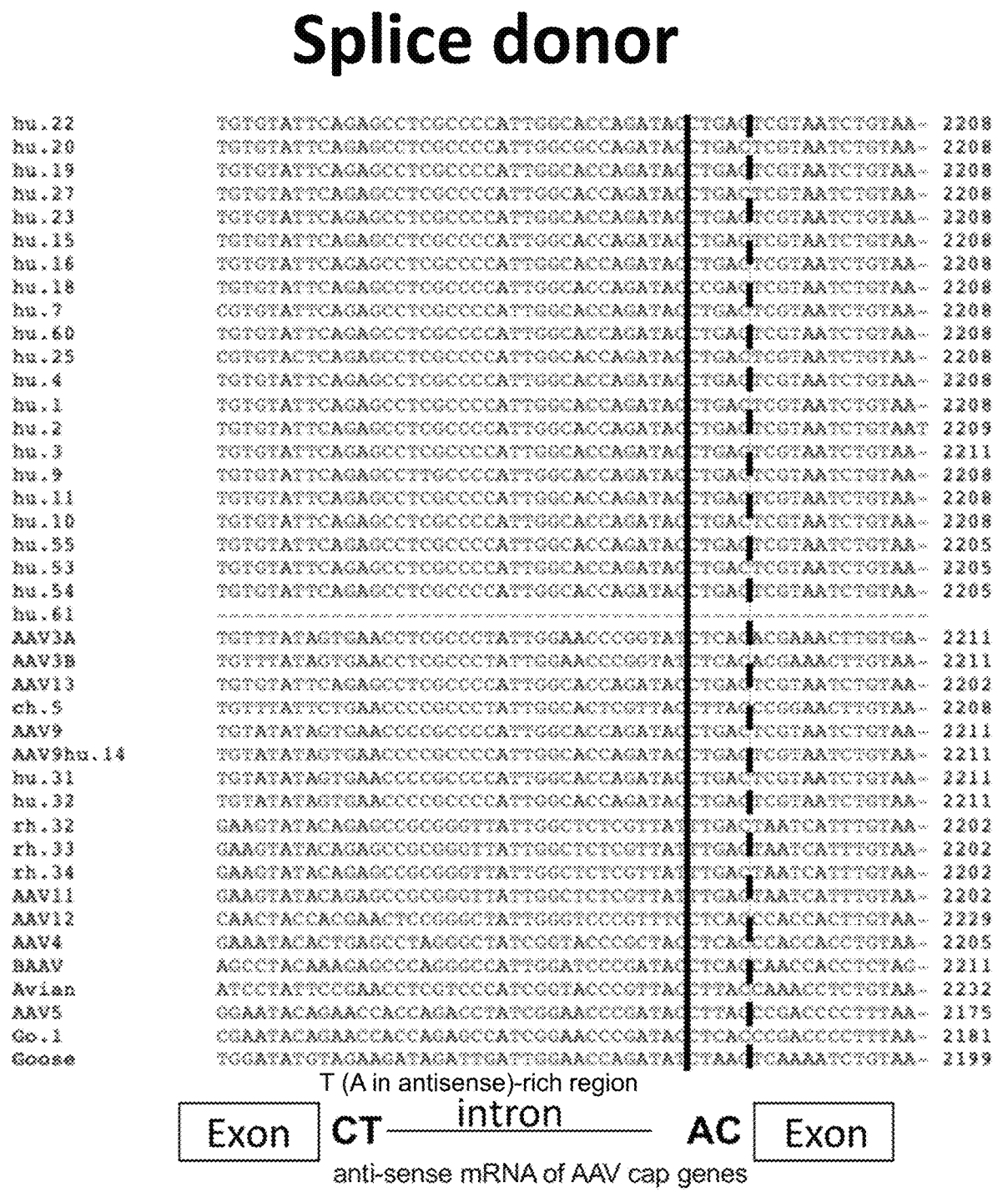

FIGS. 6A-6F: Cryptic splice donor (SD) and splice acceptor (SA) sites with the common features of exon-intron junctions present in the AAV cap ORFs in an antisense orientation. Nucleotide sequences of the cap genes derived from 122 naturally occurring AAV strains (serotypes and variants) are aligned using a multiple sequence alignment program (SEQ ID NO 223-316). The exon-intron junctions identified in the AAV9 cap ORF-derived antisense mRNA are indicated with solid lines. The dashed line in the splice acceptor region indicates putative splice acceptor sites in the AAV cap ORFs devoid of the splice acceptor AG/TC sequence at the position expected from the sequence conservation. The dashed line in the splice donor region indicates the splice donor site identified in the AAV3 cap ORF-derived antisense mRNA (please refer to FIGS. 7A-7B). The GT/CA splice donor sites and the AG/TC splice acceptor motifs, followed by a stretch of T's, are the common features of exon-intron junctions and are very well-conserved across many AAV strains. The splice donor and acceptor sites identified in the AAV9 cap ORF shown in this figure have also been identified in the AAV1 cap ORF. For serotypes other than AAV1, 3, 5 and 9, splicing events in antisense mRNA of the AAV cap ORFs are currently under investigation. The highlighted variants are common AAV serotypes.

FIGS. 7A-7B: Introns identified in antisense mRNA derived from the AAV3 cap gene. pAAV3-hnLSP-MCS-TRADE2 is a plasmid carrying the wild-type AAV3 cap ORF placed under a liver-specific enhancer-promoter with an MVM intron (hnLSP). The nucleotide sequence of the AAV3 cap ORF is the same as that of the naturally identified AAV3. HepG2 cells, a human hepatoma cell line, were transfected with plasmid pAAV3-hnLSP-MCS-TRADE2. Antisense mRNA derived from the AAV3 cap ORF was then analyzed by RT-PCR. Sequences of two truncated RT-PCR products were determined by Sanger sequencing following blunt-end TOPO cloning of the PCR products, which revealed introns found within the antisense AAV3 cap ORF (Panels A and B, SEQ ID NO:193). Intron sequences are in lowercase letters with underline. The most upstream splice donor site is found to be only 3 bp away from the splice donor site identified in the AAV9 cap ORF, which is indicated in a dashed line in FIGS. 6B-6F. The most downstream splice acceptor site is found approximately 80 bp upstream of that of the AAV9 cap ORF. Please note that all the splice donor and acceptor sites identified in the AAV3 cap ORF have also been identified in the AAV1 cap ORF.

Figure 8D:
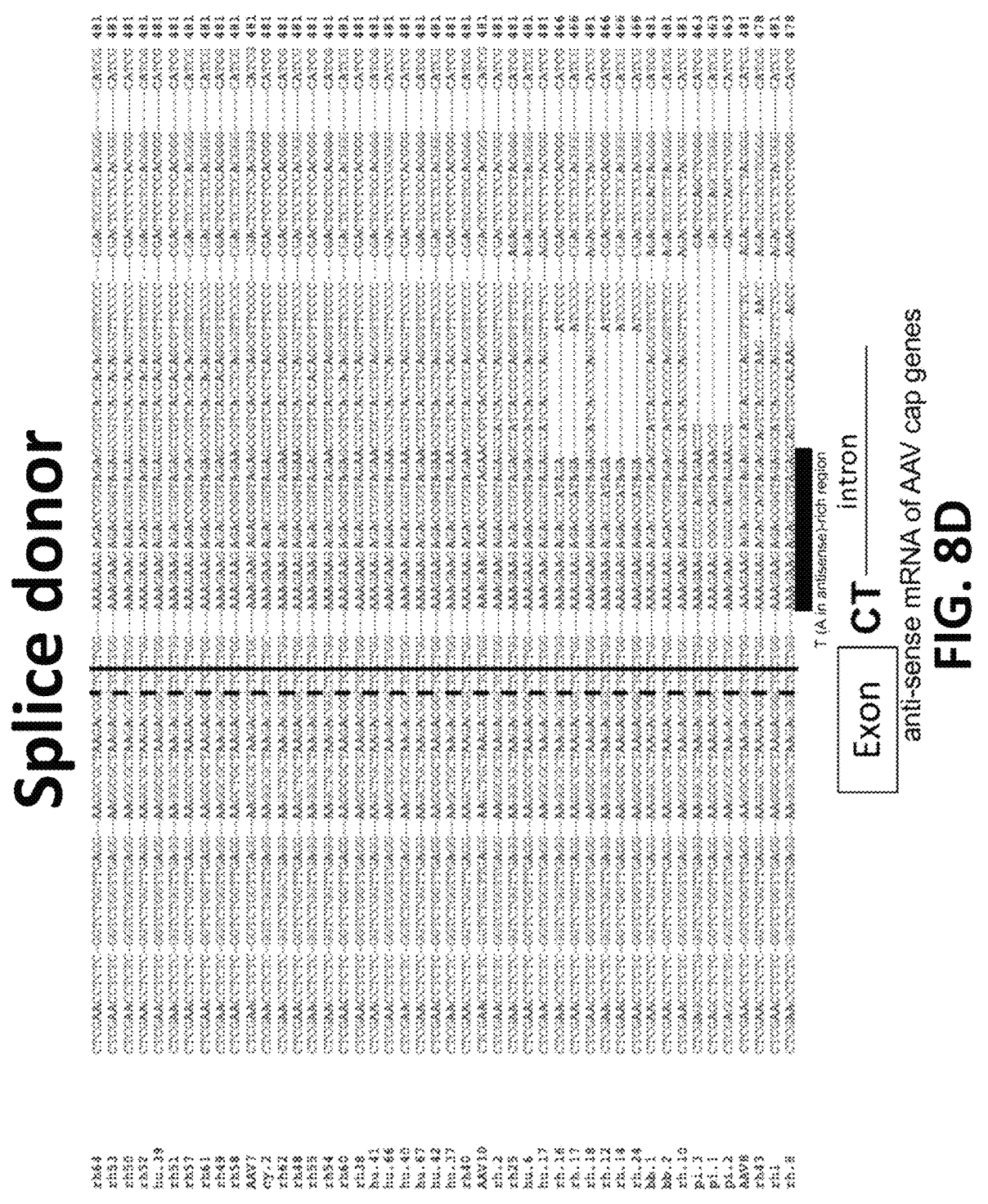
Figure 8E:
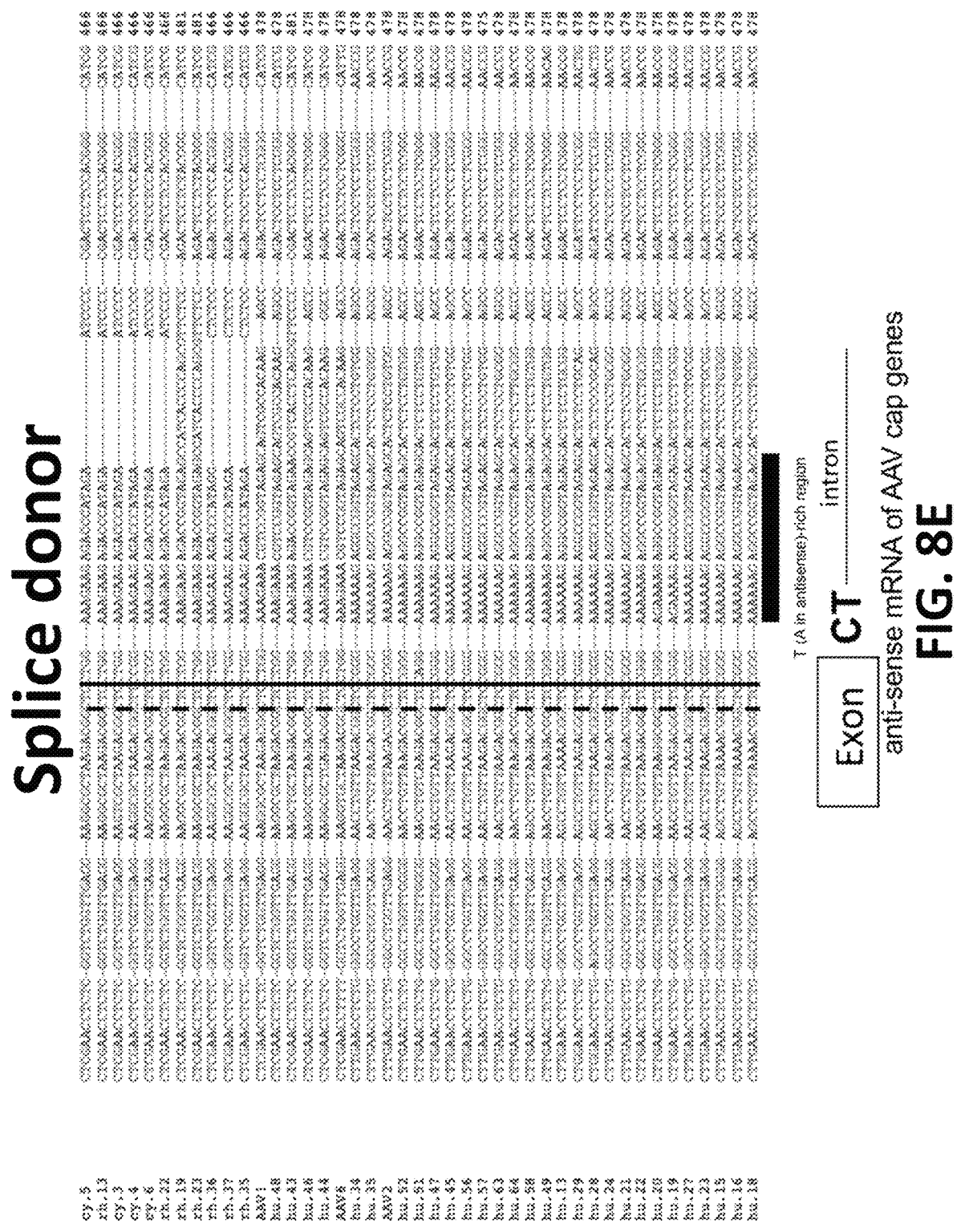
Figure 8F:
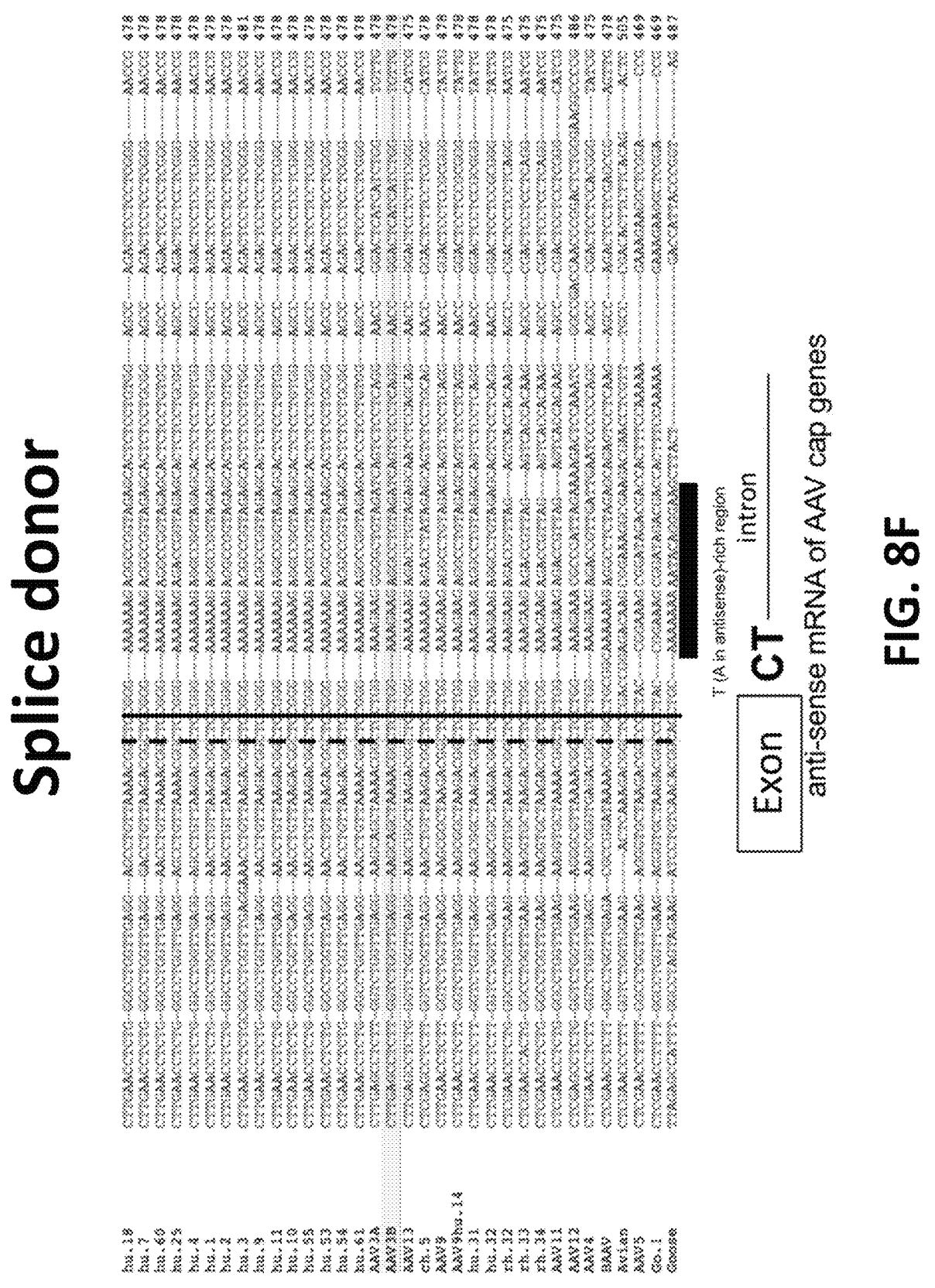

FIGS. 8A-8F. Additional cryptic splice acceptor sites present in the AAV cap ORFs. (FIG. 8A, FIG. 8B, FIG. 8C, FIG. 8D, FIG. 8E, and FIG. 8F) Nucleotide sequences of the cap genes derived from 122 naturally occurring AAV strains (serotypes and variants) are aligned using a multiple sequence alignment program (SEQ ID NO:317-420). The exon-intron junctions at the splice acceptor sites identified in the AAV3 cap ORF-derived antisense mRNA are indicated with solid thin lines. The dashed line in Panel A indicates alternative putative splice acceptor sites near the experimentally determined splice acceptor site. The AG/TC splice acceptor sites, followed by a stretch of T's, are a common feature of exon-intron junctions at splice acceptor sites and are very well conserved across many AAV strains. The AAV3 cap ORF is highlighted. The splice acceptor sites identified in the AAV3 cap ORF shown in Panels A and B have also been identified in the AAV1 cap ORF. As for the AAV5 cap ORF, no splicing events have been observed at any sites in antisense mRNA transcription. For serotypes other than AAV1, 3, 5 and 9, splicing events in antisense mRNA of the AAV cap ORFs are currently under investigation.

Figure 9A:
Figure 9B:
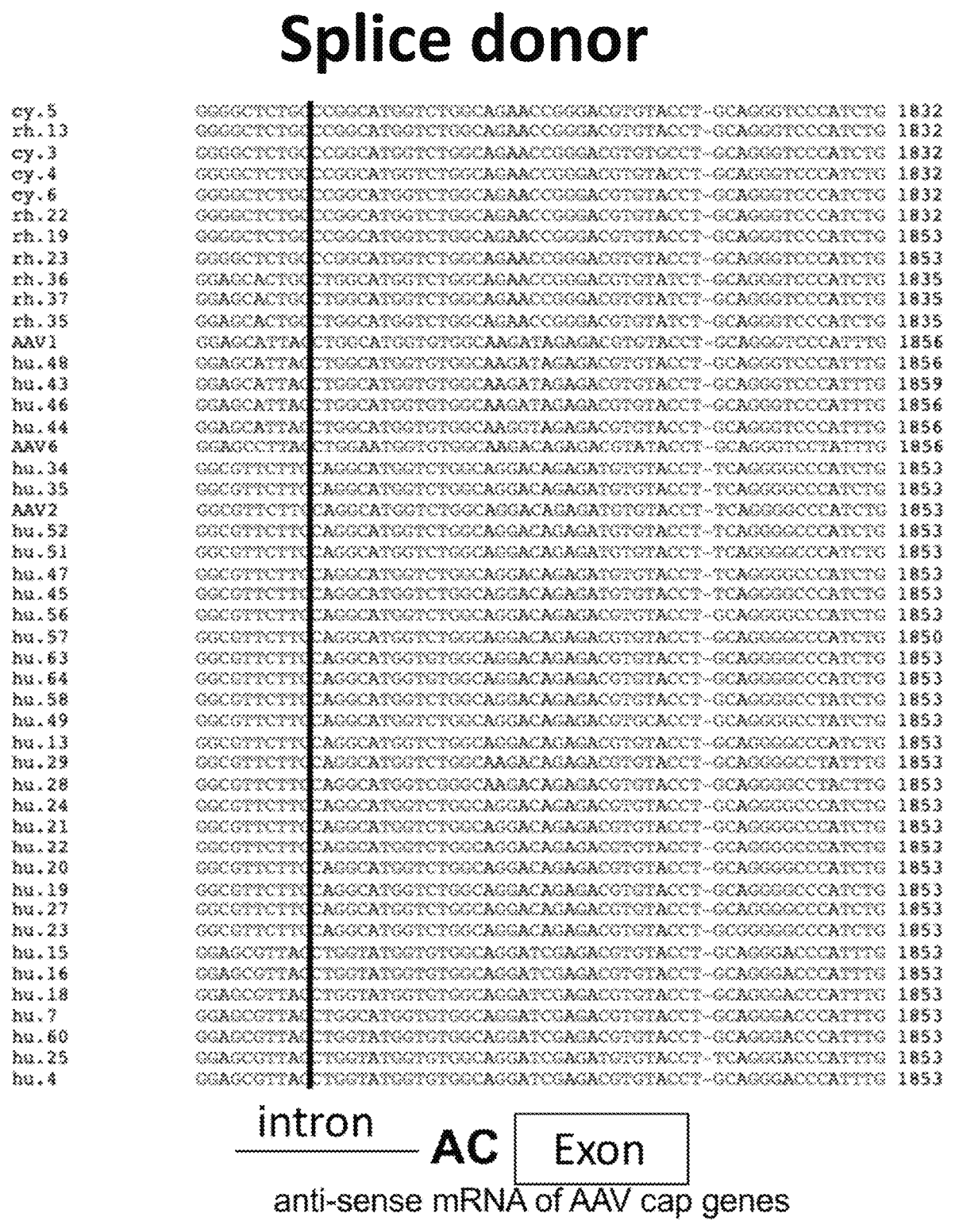
Figure 9C:

FIGS. 9A-9C: Additional potential splice donor sites present in the AAV cap ORFs. Nucleotide sequences of the cap genes derived from 122 naturally occurring AAV strains (serotypes and variants) are aligned using a multiple sequence alignment program (SEQ ID NO:421-461). The exon-intron junctions at the splice donor sites identified in the AAV3 cap ORF-derived antisense mRNA are indicated with a solid line. The GT/CA splice donor consensus sequence at this position is retained by only half of AAV strains. This splice donor site has been identified in the AAV1 cap ORF.

FIG. 10 Splice donor and splice acceptor sites identified in the AAV1 cap ORF. The nucleotide sequence of the AAV1 cap ORF is shown (SEQ ID NO:194). The AAV1 cap ORF was expressed by the hSynI enhancer-promoter in human embryonic kidney (HEK) 293 cells or Neuro2a cells in an antisense orientation. Antisense mRNA derived from the AAV1 cap ORF was then analyzed by RT-PCR. Sequences of RT-PCR products were determined by Sanger sequencing following blunt-end TOPO cloning of the PCR products, which revealed introns found within the AAV1 cap ORF. Exon-intron junctions identified in antisense AAV1 cap mRNA are indicated with AG/TC for the splice donor sites and GT/CA for the splice acceptor sites. AG/TC and GT/CA in uppercase are the consensus two nucleotides at the 5' end and the 3' end of an intron, respectively. Since the splicing occurs in antisense mRNA of the ORF, intron sequences are between CT (splice acceptor) and AC (splice donor) in various combinations in the above sequence. The detailed information about the observed combinations of the splice donors and acceptors is not shown. The two conserved nucleotides at exon-intron junctions (CT or AC) indicated in boldface are those that are highly conserved across different AAV serotypes. The two conserved nucleotides at exon-intron junctions (CT or AC) that are underlined are those that have also been identified in antisense AAV3 or AAV9 cap mRNA transcripts.

Figure 11:
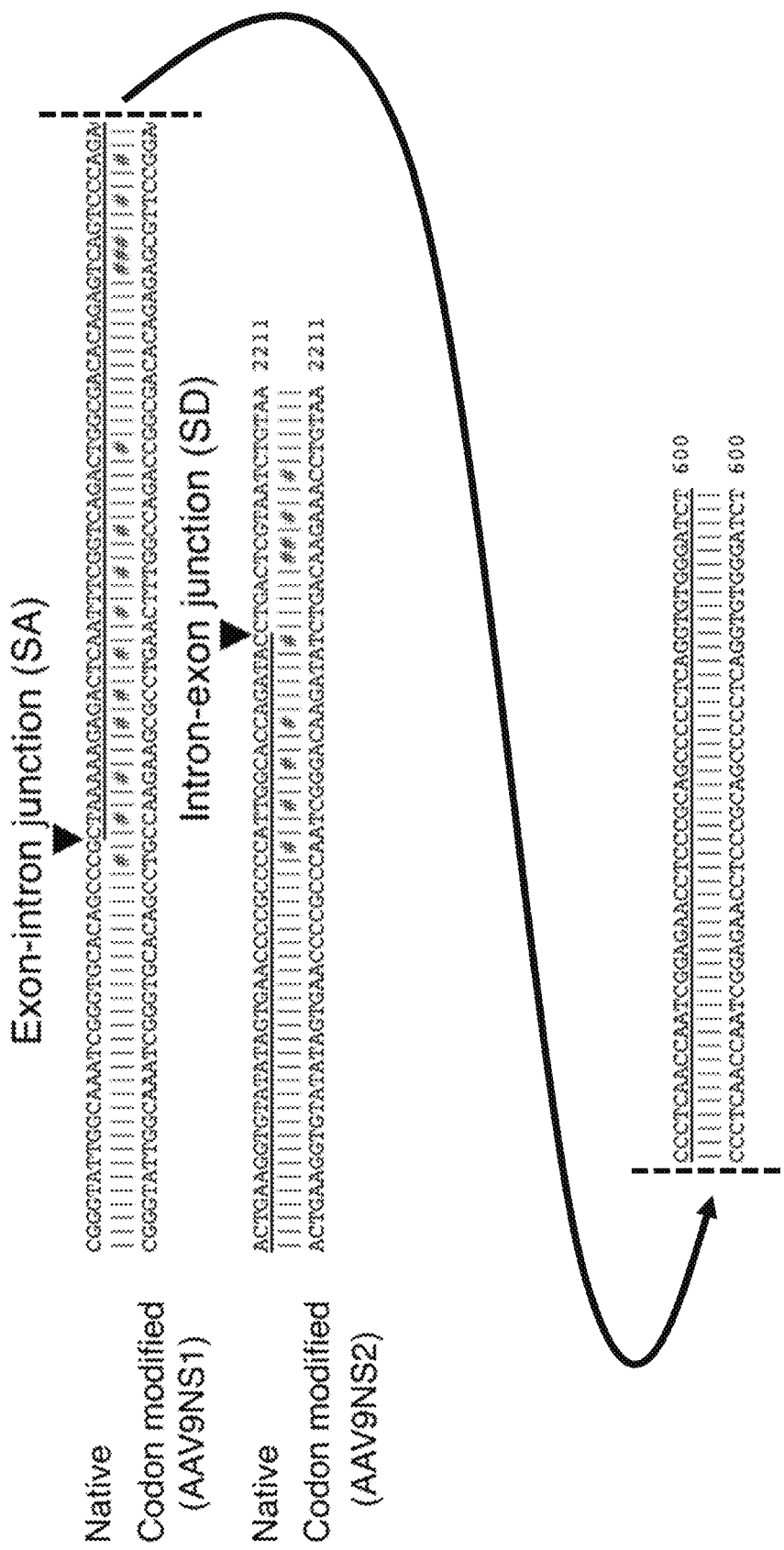

FIG. 11 Splicing-suppressing mutagenesis of the AAV9 cap ORF. Silent mutations are introduced around the splice acceptor (SA) site and/or the splice donor (SD) site in the AAV9 cap ORF to suppress the splicing observed on the antisense mRNA transcripts. The spliced-out intron from the native sequence (SEQ ID NO:195, SEQ ID NO:196) is indicated with underlines. The AAV9NS1 genome (SEQ ID NO:197) has a set of mutations around the SA site while the AAV9NS2 genome (SEQ ID NO:198) has a set of mutations around the SD site. The AAV9NS3 genome has both sets of mutations. The numbers to the right indicate the nucleotide position relative to the first nucleotide of the AAV9 cap ORF.

Figure 4:
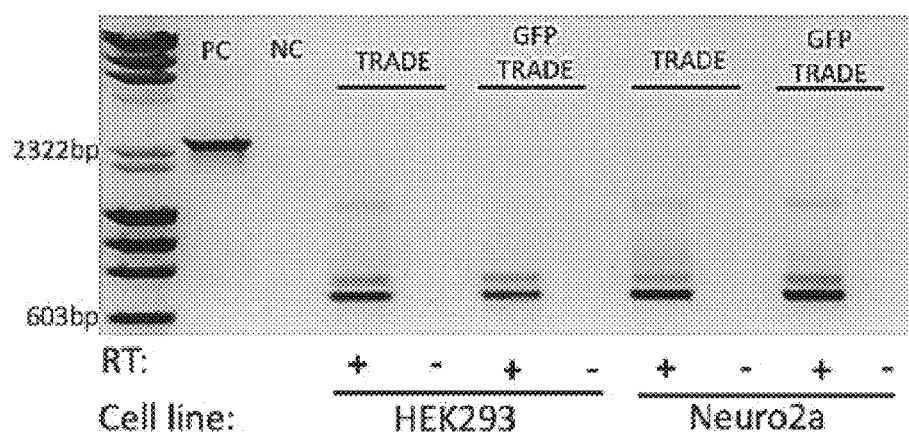
FIG. 4 Splicing of the antisense mRNA of the AAV9 cap ORF. Two cell lines, HEK293 and Neuro2a, were transfected with plasmids containing the AAV9 cap ORF in the TRADE configuration, with or without a GFP reporter. They are indicated as "GFP TRADE" and "TRADE", respectively, in the figure. Cells were harvested 3 days post-transfection, RNA was extracted, and RT-PCR was performed with a set of PCR primers that amplify the full cap ORF sequence. Instead of recovering the expected amplicon size of 2.4 kb as shown in the positive control (PC) lane, we consistently recovered amplicons of approximately 0.7 kb. Sanger sequencing of these RT-PCR products identified a truncation consistent with splicing of a 1.7 kb region of the AAV9 cap ORF indicated in FIG. 5. PC, a positive control using a plasmid template containing the AAV-PHP.B-hSynI-GFP-TRADE vector genome sequence; NC, a no template PCR control.
Figure 6A:
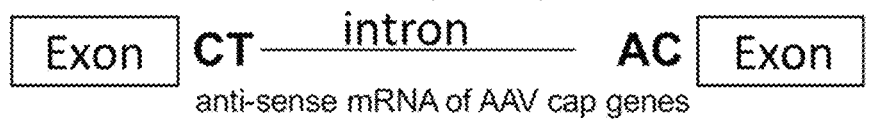
Figure 6B:
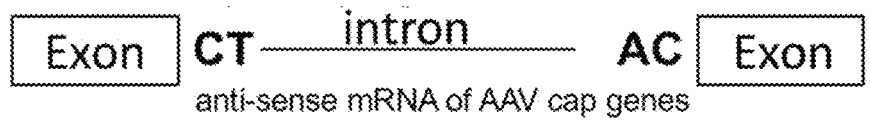
Figure 6C:
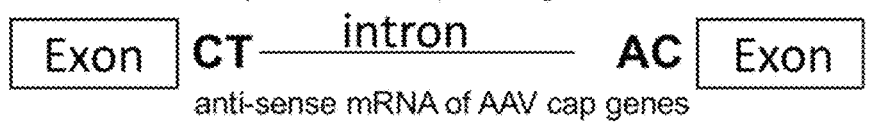
Figure 6D:
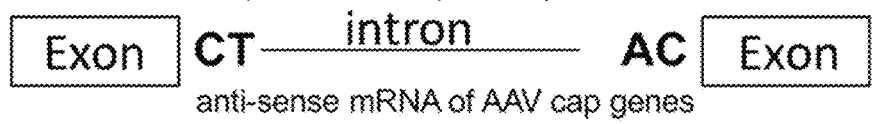
Figure 6E:
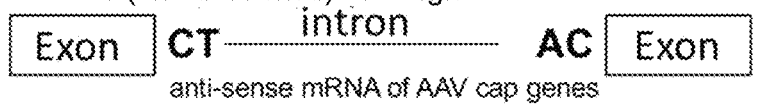
Figure 8A:
Figure 8B:
Figure 8C:
Figure 12:
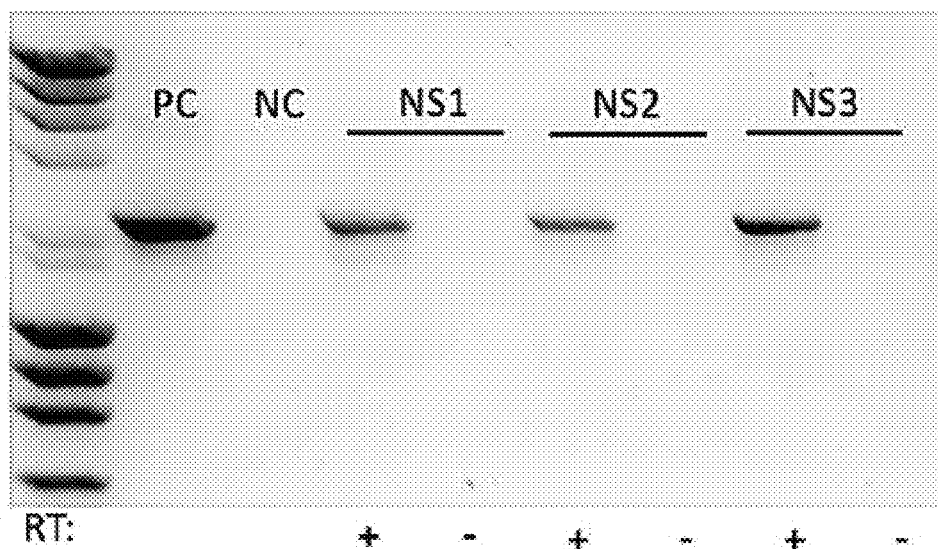

FIG. 12 Mutations introduced around the splice donor and/or accepter site(s) effectively suppress the splicing of antisense mRNA derived from the AAV9 cap ORF. Neuro2a cells were transfected with plasmids containing the AAV9 cap ORF and various potentially splicing-suppressing mutations in the TRADE configuration (NS1-3). RNA was harvested 3 days post-transfection and RT-PCR was performed with a set of PCR primers that can recover the full cap ORF sequence. In stark contrast to results seen in FIG. 4, full-length amplicons were successfully recovered. NS1, the AAV9-TRADE vector genome with a codon-modified splice acceptor. NS2, the AAV9-TRADE vector genome with a codon-modified splice donor. NS3, the AAV9-TRADE vector genome with codon-modified splice acceptor and splice-donor. PC, a positive control using a plasmid template containing the AAV-PHP.B-hSynI-GFP-TRADE vector genome sequence; NC, a no template PCR control.

Figure 13A:
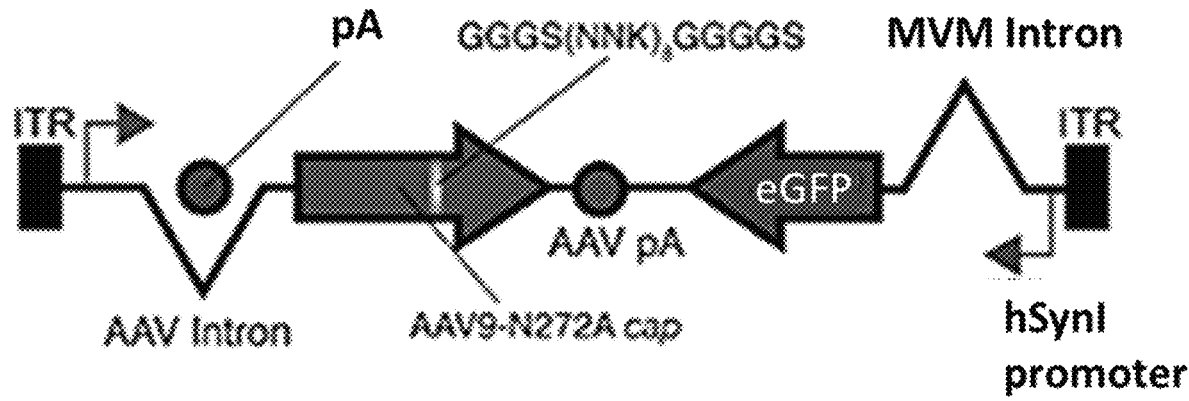
Figure 13B:
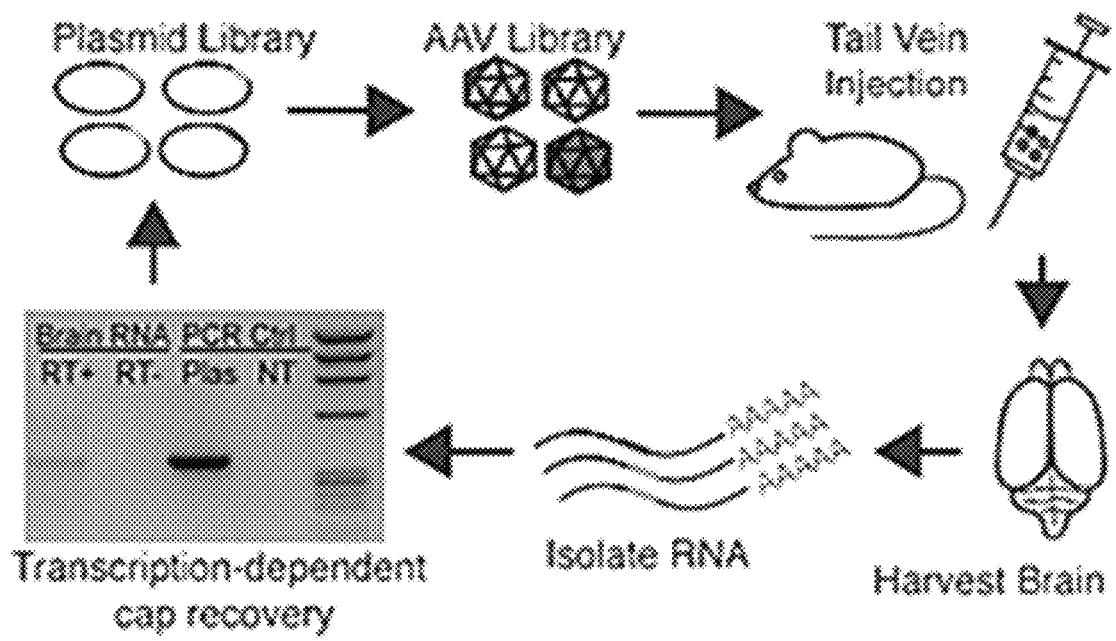

FIGS. 13A-13B: Study design for application of TRADE to identify enhanced AAV variants for brain neuron transduction following systemic AAV vector injection. (A) A map of the AAV9-N272A-hSynI-GFP-TRADE-PepLib vector genome. The hSynI enhancer-promoter is utilized to drive expression specifically in neurons. The liver-detargeted AAV9-N272A cap (PCT/US2017/068050) serves as the platform for AAV library generation. A randomized 8 amino acid peptide encoded by $(NNK)_8$ and flanked by glycine-serine linkers (SEQ ID NO:2) was substituted for Q588 of the AAV9-N272A cap sequence (SEQ ID NO:222). (B) The plasmid library was used to produce an AAV library using a triple transfection protocol. The library was purified through PEG precipitation and two rounds of CsCl ultracentrifugation, then injected via tail vein at a dose of $3 \times 10^{11}$ vg/mouse. Brain tissue was harvested 12 days post-injection. RNA was recovered using TRIzol and RT-PCR was used to recover a fragment of cap containing the peptide insertion, which was subsequently cloned back into the AAV vector plasmid backbone. This was repeated for 3 rounds of selection in C57BL/6J mice. In parallel, a single round of selection was performed in rhesus macaque using a dose of $2.7 \times 10^{12}$ vg/kg.

FIGS. 14A-14D: Validation of neuronal transduction of the 26 novel AAV capsids in mice and a nonhuman primate by AAV RNA Barcode-Seq. (FIG. 14A) A map of the double-stranded (ds) AAV-hSynI-GFP-BC vector. A pair of two 12 nucleotide-long DNA barcodes (VBCx-L and VBCx-R) are placed under the human synapsin I (hSynI) gene enhancer-promoter. These two virus barcodes (VBCs) can be expressed as transcripts specifically in cells where the hSynI enhancer-promoter is active (i.e., neurons). (FIG. 14B) Neuronal transduction of 26 novel AAV variants, HN1 to HN26, identified by TRADE (5 variants identified in mice and 21 variants identified in a non-human primate) and 3 control AAV capsids (AAV9, AAV9-N272A and AAV-PHP.B) in C57BL/6J and BALB/cJ mice. A DNA/RNA-barcoded dsAAV-hSynI-GFP-BC library (dsAAV-hSynI-GFP-BCLib) containing 26 novel AAV variants identified by TRADE (5 variants identified by TRADE in mice and 21 variants identified by TRADE in a non-human primate) and control AAV capsids (AAV9, AAV9-N272A and AAV-PHP.B) was injected intravenously into three adult male C57BL/6J mice and three adult male BALB/cJ mice at a dose of $5 \times 10^{11}$ vg per mouse. Two weeks post-injection, various tissues were harvested and analyzed for transduction at AAV vector genome transcripts levels by AAV RNA Barcode-Seq. Transduction levels are expressed as phenotypic difference (PD) values relative to the reference control, AAV9. For the AAV capsid amino acid sequence information of the HN1 to HN26 variants, please refer to Table 3. (FIG. 14C) Neuronal transduction of the 26 novel AAV variants and 3 control AAV capsids in the hippocampus of a rhesus macaque. The same DNA/RNA-barcoded AAV library was injected intravenously into one juvenile male rhesus macaque at a dose of $2 \times 10^{13}$ vg/kg. Two weeks post-injection, various brain regions were harvested and analyzed for transduction by AAV RNA Barcode-Seq. (FIG. 14D) Relative neuronal transduction efficiencies of 3 TRADE variants, HN1, HN2 and HN3, and AAV-PHP.B were analyzed by AAV RNA Barcode-Seq in 12 different brain regions in the single rhesus macaque used for Panel C. In Panels B, C and D, dashed lines indicate the PD value of AAV9 (i.e., 1.0).

Figure 15A:
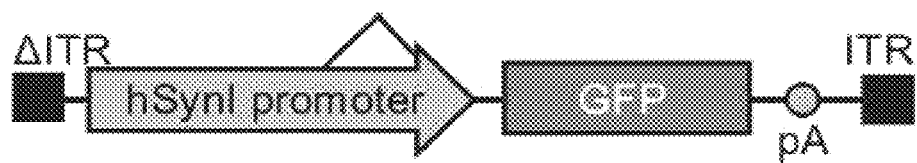
Figure 15B:
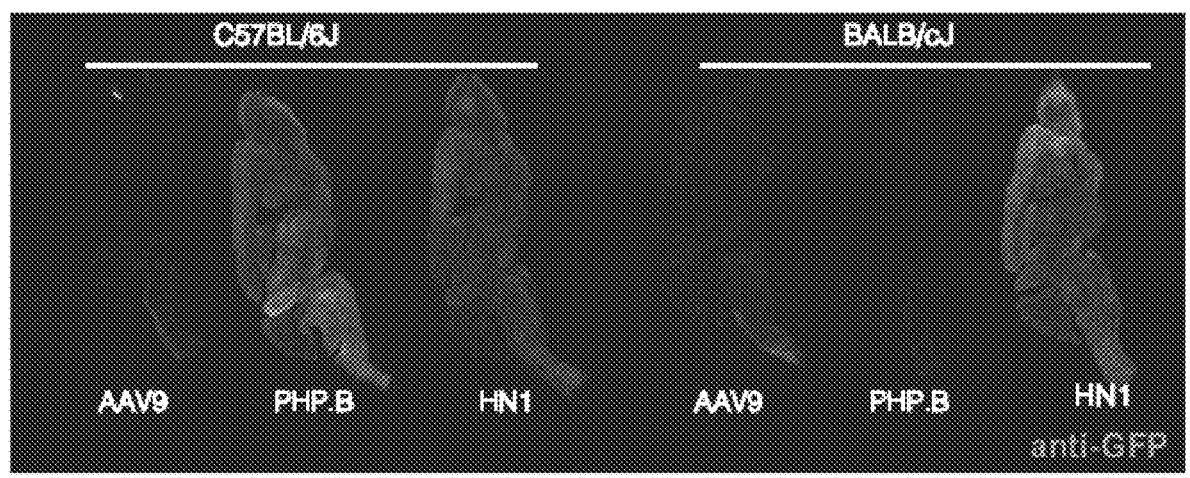
Figure 15C:
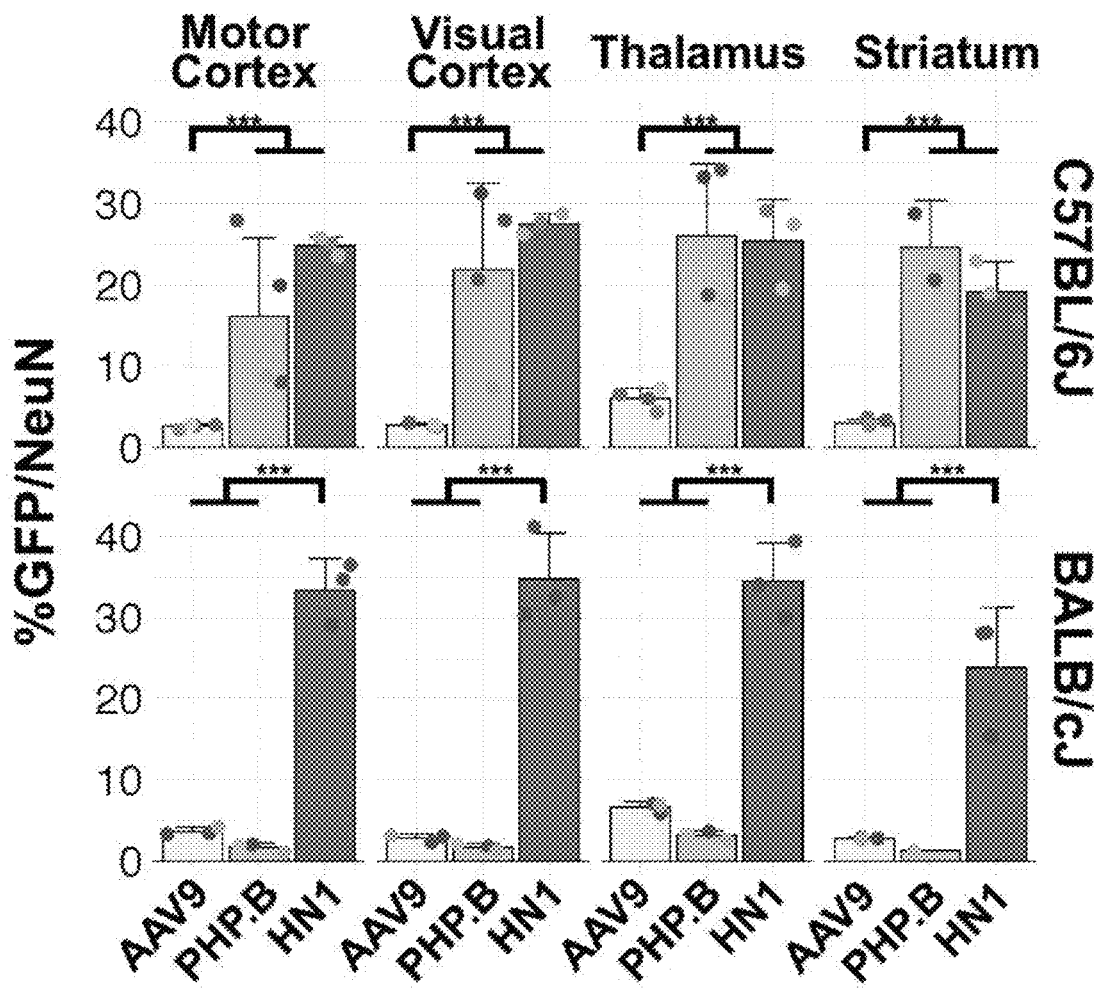
Figure 15D:
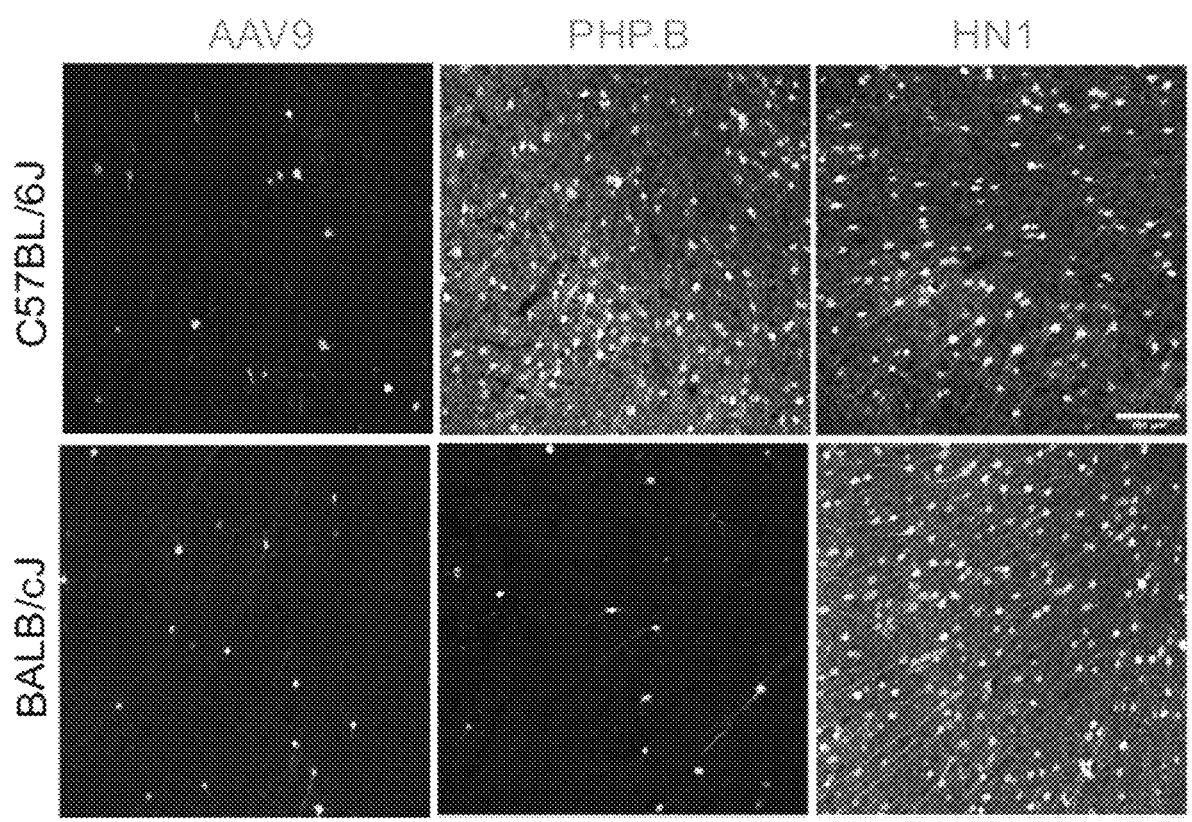
Figure 15E:
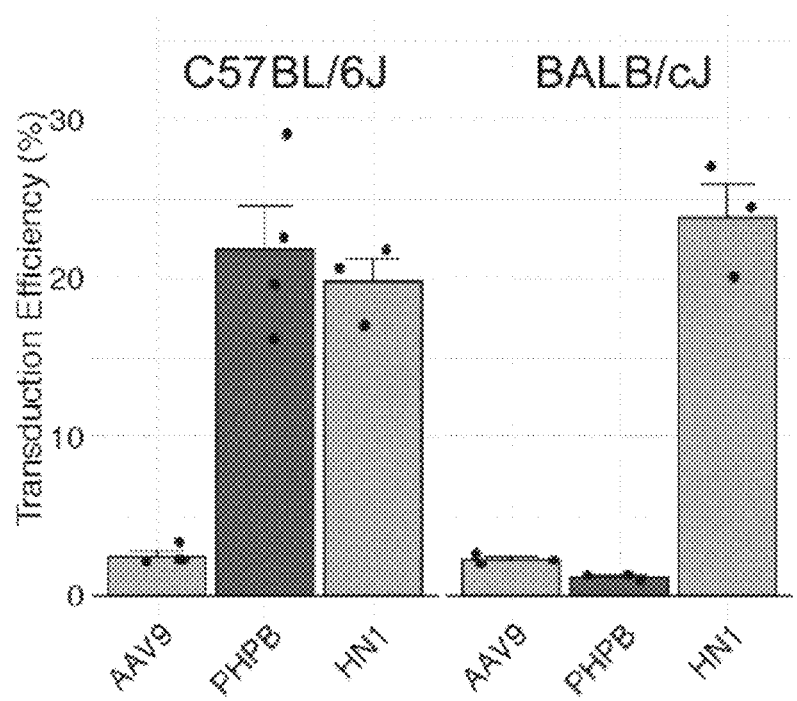

FIGS. 15A-15E: Validation of enhanced neuronal transduction of AAV9-N272A-HN1 in mice using conventional eGFP reporter vectors and histological quantification. We produced AAV9, AAV-PHP.B, and AAV9-N272A-HN1 vectors containing self-complementary AAV genomes expressing eGFP under the control of the hSynI enhancer-promoter (dsAAV-hSynI-eGFP). Purified vectors were administered via the tail vein at a dose of $3 \times 10^{11}$ vg/mouse into 8-week old male C57BL/6J or BALB/cJ mice (n=4 mice/vector/mouse strain). Three weeks post-injection, mice were transcardially perfused with 4% paraformaldehyde and brain tissue was processed for immunohistochemistry. (FIG. 15A) A map of the self-complementary hSynI-eGFP vector genome. (FIG. 15B) Representative tilescan images of sagittal sections stained with anti-GFP antibody. (FIG. 15C) Quantification of neuronal transduction in (FIG. 15B) based on automated counts of cells expressing eGFP and NeuN in four brain regions. (FIG. 15D) Validation of the automated counting process in (FIG. 15B) and (FIG. 15C). Representative 20× confocal images from visual cortex are shown. Scale bar=100 µm. (FIG. 15E) Quantification of neuronal transduction in (FIG. 15D) based on hand counts of cells expressing eGFP and NeuN by a blinded observer. Error bars represent mean+/−SEM. ***$p<0.001$.

Figure 16A:
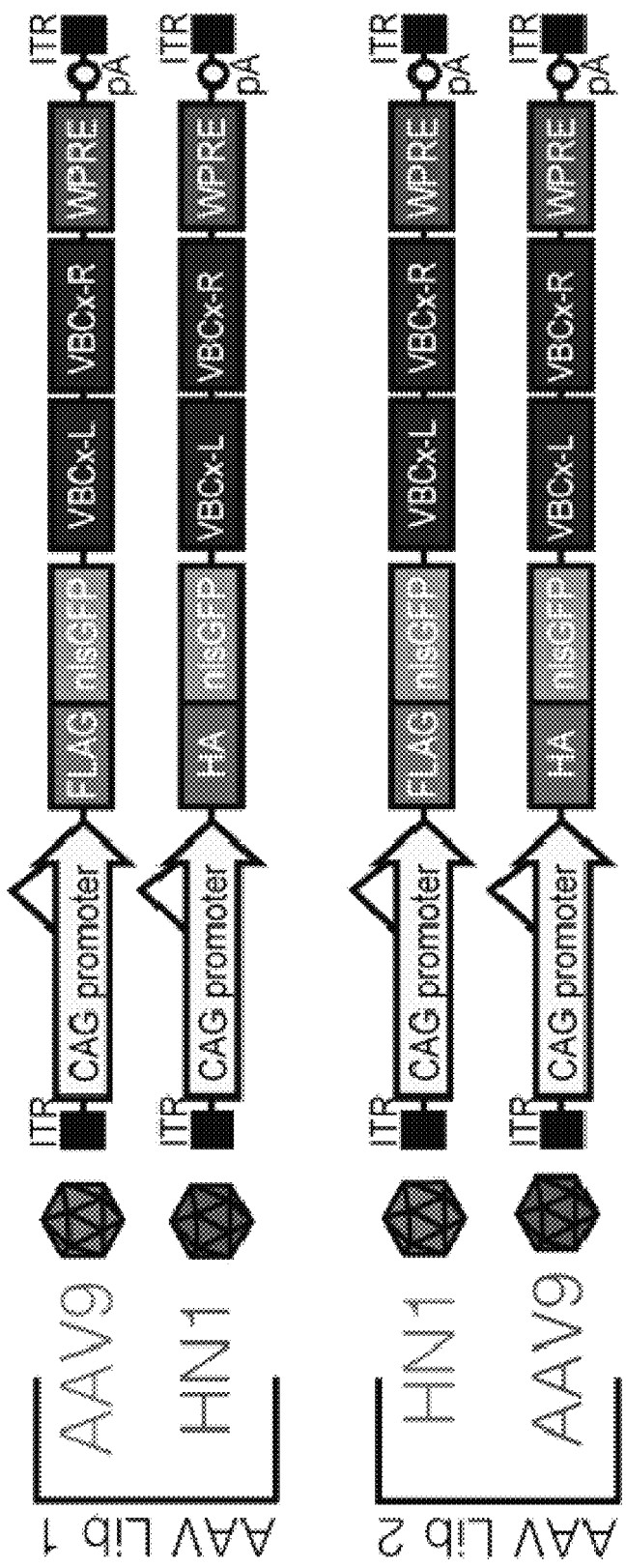
Figure 16B:
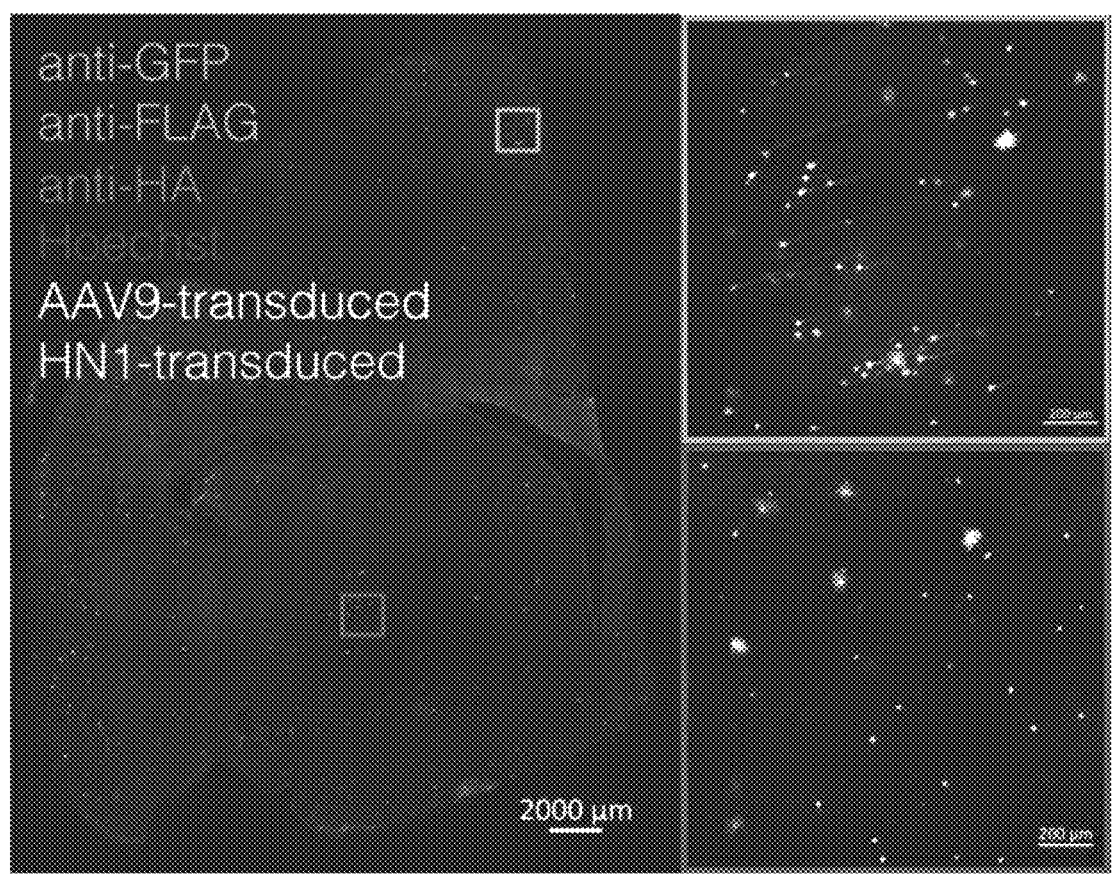

FIGS. 16A-16B: Validation of enhanced AAV9-N272A-HN1 transduction relative to AAV9 in rhesus macaques using epitope-tagged eGFP reporter vectors. (FIG. 16A) AAV-CAG-nlsGFP vectors used for this study. We produced 4 AAV vectors: AAV9-CAG-FLAGnlsGFP-BCLib, AAV9-CAG-HAnlsGFP-BCLib, AAV9-N272A-HN1-CAG-FLAGnlsGFP-BCLib and AAV9-N272A-HN1-CAG-HAnlsGFP-BCLib. The nlsGFP (eGFP with the nuclear localization signal derived from the SV40 large T antigen) was tagged with either the FLAG tag or the HA tag at the N-terminus. Each vector was a DNA/RNA-barcoded library containing an approximately 1 to 1 mixture of 9 different DNA/RNA-barcoded viral clones; however, this feature was not used in this study. The two vectors in the top half depicted in Panel A were mixed at a ratio of 1:1 to make AAV Library 1 (AAVLib1) and the two vectors in the bottom half were mixed at a ratio of 1:1 to make AAV Library 2 (AAVLib2). In this experimental scheme, AAVLib1 and AAVLib2 each contain AAV9 and AAV9-N272A-HN1 vectors expressing epitope-tagged nlsGFP at a ratio of 1:1, but the capsid-epitope relationship is inverted in order to avoid potential antibody bias in downstream analyses. (FIG. 16B) Representative tile-scanned brain section from one animal receiving AAVLib. Each AAV library was administered intravenously into a juvenile rhesus macaque at a dose of $3 \times 10^{13}$ vg/kg. Tissue was harvested 3-weeks post-injection, cut into 4 mm slabs, fixed in 4% paraformaldehyde, and processed for immunohistochemical analysis with anti-GFP, anti-FLAG and anti-HA antibodies. eGFP expression indicates that a cell was transduced by either AAV9 or AAV9-N272A-HN1 or both. FLAG staining indicates that the AAV9 capsid mediated transduction, while HA staining indicates that AAV9-N272A-HN1 mediated transduction. Top-right inset, motor cortex; bottom-right inset, putamen. This experiment revealed that AAV9-N272A-HN1 transduced the brain cells better than AAV9 by several fold with strong neuronal tropism compared to AAV9. Therefore, as far as neuronal transduction is concerned, AAV9-N272A-HN1 mediates much higher neuronal transduction than AAV9.

FIGS. 17A-17D: Biodistribution of AAV9-N272A-HN1 to major peripheral organs following systemic delivery in mice and rhesus macaques. We used AAV DNA Barcode-Seq to determine relative abundance of AAV vector genome DNAs in each peripheral organ, delivered by each AAV capsid contained in the dsAAV-hSynI-GFP-BCLib library (Panels FIG. 17A, FIG. 17B and FIG. 17C). As explained earlier, the dsAAV-hSynI-GFP-BCLib library contained 26 AAV variants identified by TRADE in mice and in a non-human primate together with the controls, AAV9, AAV9-N272A and AAV-PHP.B. DNA was extracted from various tissues following administration of the dsAAV-hSynI-GFP-BCLib library (see Table 3) and subjected to AAV DNA Barcode-Seq analysis. We also used AAV RNA Barcode-Seq to determine relative transduction efficiency compared to AAV9 in each peripheral organ of rhesus macaques intravenously injected with the ssAAV-CAG-nlsGFP-BCLib library depicted in FIG. 16A (Panel D). (FIG. 17A) Biodistribution of AAV9, AAV9-N272A, AAV-PHP.B, and TRADE variants to the liver, relative to AAV9, in C57BL/6J mice, BALB/cJ mice and rhesus macaques. (FIG. 17B) Biodistribution of AAV9-N272A-HN1 to major peripheral organs besides the liver in C57BL/6J mice and BALB/cJ mice (n=3 mice/strain). (FIG. 17C) Biodistribution of AAV9-N272A-HN1 to major peripheral organs besides the liver in a rhesus macaque (n=1) based on dsAAV-hSynI-GFP-BC analysis. For this experiment, AAV DNA Barcode-Seq analysis was performed on the samples collected from one rhesus macaque injected with the dsAAV-hSynI-GFP-BCLib library shown in FIG. 14D. (FIG. 17D) Biodistribution of AAV9-N272A-HN1 to major peripheral organs besides the liver in rhesus (n=2) based on ssAAV-CAG-nlsGFP-BC analysis. For this experiment, AAV RNA Barcode-Seq analysis was performed on the samples collected from rhesus macaques injected with the ssAAV-GAG-nlsGFP-BCLib vectors shown in FIG. 16A. Error bars represent mean+/−SEM. AAV9-N272A-HN1 capsid transduced peripheral organs to a lesser degree compared to AAV9 capsid.

Figure 18A:
Figure 18B:
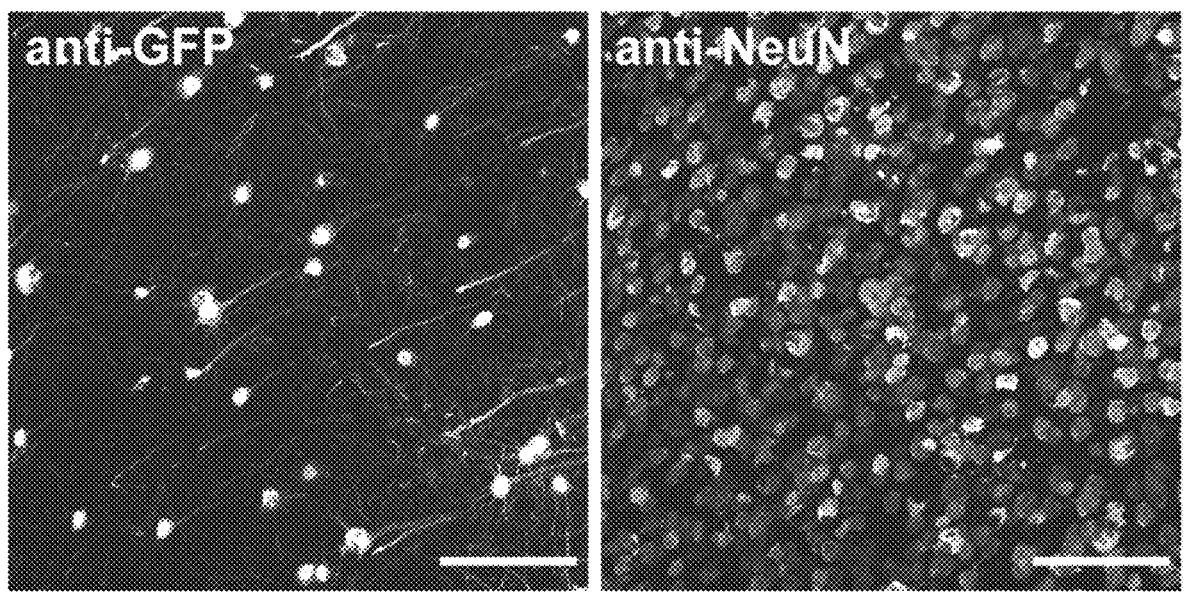
Figure 18C:
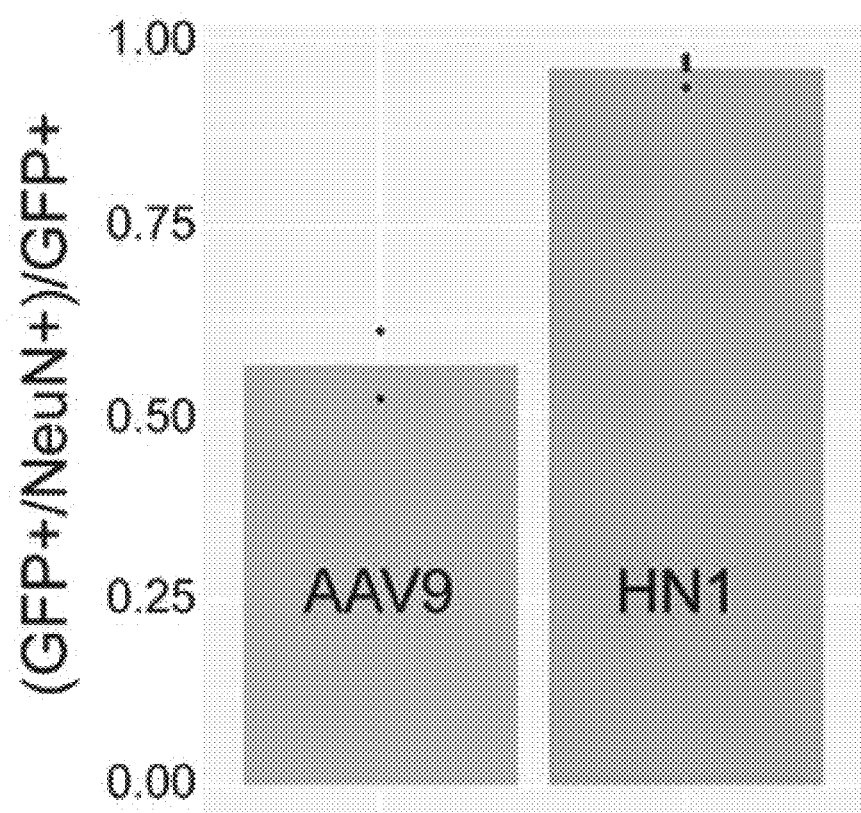

FIGS. 18A-18C: AAV9-N272A-HN1 is highly neurotropic following systemic administration in mice. AAV9 and AAV9-N272A-HN1 vectors expressing nlsGFP under the control of the strong, ubiquitous CAG promoter were injected intravenously into 8-week old male BALB/cJ mice at a dose of $3 \times 10^{11}$ vg/mouse. Tissues were harvested 12 days post-injection and analyzed by immunostaining with anti-GFP and anti-NeuN antibodies. (FIG. 18A) A map of the single-stranded (ss) AAV-CAG-nlsGFP vector genomes used in this study. (FIG. 18B) Representative image from mouse cerebral cortex transduced with AAV9-N272A-HN1-CAG-nlsGFP. The vast majority of cells transduced with AAV9-N272A-HN1-CAG-nlsGFP are also positive for the neuronal marker NeuN. Scale bar=100 µm. (FIG. 18C) Neuronal specificity of AAV9 and AAV9-N272A-HN1 capsids. Quantification of neuronal specificity was determined by dividing the number of double-positive cells (eGFP+/NeuN+) by the total number of GFP+ cells. AAV9-N272A-HN1 is highly specific to neurons (96%) compared to AAV9 (56%).

DETAILED DESCRIPTION

In some embodiments, the present disclosure provides a TRADE system that allows directed evolution of the AAV capsid using antisense mRNA of the cap ORF expressed in a cell type-specific or ubiquitous manner. Such a system does not require Cre-transgenic animals. Therefore, it can be applied to cell type-specific AAV capsid evolution in large animals, including non-human primates, for which Cre-transgenic strains are not readily available. Any cell type-specific or tissue/organ-specific enhancers/promoters or ubiquitous enhancers/promoters can be readily applied to the system with no requirement of transgenesis. The cell type-specific selection is given at the mRNA level. In certain embodiments, multiple directed evolution schemes may be combined into one directed evolution scheme. For example, selection of neuron-specific AAV capsids, astrocyte-specific AAV capsids, oligodendrocyte-specific AAV capsids and microglia-specific AAV capsids based on cell type-specific transgene mRNA expression can be performed simultaneously in a single animal.

In some embodiments, the present disclosure provides a sense strand TRADE system that allows directed evolution of the AAV capsid using mRNA of the cap ORF expressed in a cell type-specific or ubiquitous manner that is capable of expressing AAV capsid proteins in target cells. The sense strand TRADE has the same advantages of those antisense strand TRADE presented with data here in that it does not require Cre-transgenic animals, cell type-specific selection is given at the mRNA level, and it is capable of combining multiple directed evolution schemes into one directed evolution round done in a single animal. However, the possible disadvantage is that immunogenic AAV capsid proteins may be unavoidably expressed persistently in target cells, which may result in undesired consequences in the capsid selection process.

In some embodiments, the present disclosure also provides novel AAV capsids. In certain embodiments, these novel AAV capsids can transduce brain neurons several times better than AAV9 in C57BL/6J mice following intravenous injection. In certain embodiments, the novel AAV capsids transduced up to 8 times better than AAV9 in C57BL/6J mice following intravenous injection. The neuronal transduction levels may be greatly enhanced compared to AAV9 although they may not attain the levels obtained with AAV PHP.B. In certain embodiments, the novel AAV capsids may transduce brain neurons more efficiently than AAV PHP.B.

In some embodiments, this disclosure provides novel AAV capsids that can transduce brain neurons several times better than AAV9 following intravenous injection in BALB/cJ mice. In certain embodiments, the novel AAV capsids can transduce brain neurons up to 7 times better than AAV9 following intravenous injection in BALB/cJ mice. The transduction levels are much higher than AAV PHP.B.

In some embodiments, this disclosure provides novel AAV capsids that can transduce brain neurons several times better than AAV9 in rhesus macaques following intravenous injection. In certain embodiments, the novel AAV capsids can transduce brain neurons up to 4 times better than AAV9 in rhesus macaques following intravenous injection. These transduction levels are better than AAV PHP.B.

In some embodiments, the disclosure provides AAV capsids that can transduce the pulmonary cells with neuronal cell marker expression several times better than AAV9. In certain embodiments, the AAV capsids can transduce such cells up to 17 times better than AAV9.

In some embodiments, the novel AAV capsids exhibit a liver-detargeting phenotype.

In some embodiments, the disclosure provides codon-modified AAV cap sequences that are not spliced when expressed in an antisense direction. We have observed that unmodified AAV cap ORFs are spliced when expressed in an antisense direction (e.g., AAV1, AAV3 and AAV9). In contrast, some of the codon-modified AAV cap ORFs described in this disclosure are not spliced. Based on the knowledge we have developed about the putative splice donor and acceptor sites, it has become possible to design such non-spliced versions of AAV cap ORFs. The use of such non-spliced cap ORFs may be used for directed evolution using the TRADE system when mutagenesis of the cap gene takes place over a wide region of the cap ORF.

The term "AAV vector" as used herein means any vector that comprises or derives from components of AAV and is suitable to infect mammalian cells, including human cells, of any of a number of tissue types, such as brain, heart, lung, skeletal muscle, liver, kidney, spleen, or pancreas, whether in vitro or in vivo. The term "AAV vector" may be used to refer to an AAV type viral particle (or virion) comprising at least a nucleic acid molecule encoding a protein of interest.

Additionally, the AAVs disclosed herein may be derived from various serotypes, including combinations of serotypes (e.g., "pseudotyped" AAV) or from various genomes (e.g., single-stranded or self-complementary). In particular embodiments, the AAV vectors disclosed herein may comprise desired proteins or protein variants. A "variant" as used herein refers to an amino acid sequence that is altered by one or more amino acids. The variant may have "conservative" changes, wherein a substituted amino acid has similar structural or chemical properties, e.g., replacement of leucine with isoleucine. Alternatively, a variant may have "nonconservative" changes, e.g., replacement of a glycine with a tryptophan. Analogous minor variations may also include amino acid deletions or insertions, or both.

Nucleotide sequences, such as polynucleotides, encoding proteins of the present disclosure are provided herein. The nucleotides of the present disclosure can be composed of either RNA or DNA. The disclosure also encompasses those polynucleotides that are complementary in sequence to the polynucleotides disclosed herein.

Because of the degeneracy of the genetic code, a variety of different polynucleotide sequences can encode the proteins of the present disclosure. In addition, it is well within the skill of a person trained in the art to create alternative polynucleotide sequences encoding the same, or essentially the same, proteins disclosed herein. These variant or alternative polynucleotide sequences are within the scope of the current disclosure. As used herein, references to "essentially the same sequence" refers to one or more sequences that encode amino acid substitutions, deletions, additions, or insertions that do not eliminate the detectability of the polypeptide encoded by the polynucleotides of the present disclosure.

The current disclosure also includes variants of the polynucleotides and polypeptides disclosed herein. Variant sequences include those sequences wherein one or more peptides or nucleotides of the sequence have been substituted, deleted, and/or inserted.

Polynucleotide and polypeptide sequences of the current disclosure can also be defined in terms of particular identity and/or similarity with certain polynucleotides and polypeptides described herein. The sequence identity will typically be greater than 60%, preferably greater than 75%, more preferably greater than 80%, even more preferably greater than 90%, and can be greater than 95%. The identity and/or similarity of a sequence can be 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical as compared to a sequence disclosed herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used.

Methods of producing AAV vectors as disclosed herein are well known in the art, including methods, for example, of using packaging cells, auxiliary viruses or plasmids, and/or baculovirus systems. See, e.g., Samulski et al., *J. Virology* 63, 3822 (1989); Xiao et al., *J. Virology* 72, 2224 (1998); Inoue et al., *J. Virology* 72, 7024 (1998); WO1998/022607; and WO2005/072364.

Methods of producing pseudotyped AAV vectors are also known (see, e.g., WO00/28004), as well as various modifications or formulations of AAV vectors, to reduce their immunogenicity upon in vivo administration (see, e.g., WO01/23001; WO00/73316; WO04/112727; WO05/005610; and WO99/06562). In some embodiments, AAV vectors may be prepared or derived from various serotypes of AAVs which may be mixed together or mixed with other types of viruses to produce chimeric (e.g., pseudotyped) AAV viruses.

In particular embodiments, the AAV vector may be a human serotype AAV vector. In such embodiments, a human AAV may be derived from any known serotype, e.g., from any one of serotypes 1-11, for instance from AAV1, AAV2, AAV4, AAV6, or AAV9.

The AAV vectors disclosed herein may include a nucleic acid encoding a protein of interest. In various embodiments, the nucleic acid also may include one or more regulatory sequences allowing expression and, in some embodiments, secretion of the protein of interest, such as e.g., a promoter, enhancer, polyadenylation signal, an internal ribosome entry site ("IRES"), a sequence encoding a protein transduction domain ("PTD"), a 2A peptide, and the like. Thus, in some embodiments, the nucleic acid may comprise a promoter region operably linked to the coding sequence to cause or improve expression of the protein of interest in infected cells. Such a promoter may be ubiquitous, cell- or tissue-specific, strong, weak, regulated, chimeric, etc., for example, to allow efficient and stable production of the protein in the infected tissue. The promoter may be homologous to the encoded protein, or heterologous, although generally promoters of use in the disclosed methods are functional in human cells. Examples of regulated promoters include, without limitation, Tet on/off element-containing promoters, rapamycin-inducible promoters, tamoxifen-inducible promoters, and metallothionein promoters. Other promoters that may be used include promoters that are tissue specific for tissues such as kidney, spleen, and pancreas. Examples of ubiquitous promoters include viral promoters, particularly the CMV promoter, the RSV promoter, the SV40 promoter, etc., and cellular promoters such as the phosphoglycerate kinase (PGK) promoter and the β-actin promoter.

In some embodiments of the AAV vectors disclosed herein, one or more feedback elements may be used to dampen over-expression of the protein of interest. For example, some embodiments of the AAV vectors may include one or more siRNA sequences that would target the exogenous transcript. In other embodiments, the AAV vector may include one or more additional promoters that may be recognized by inhibitory transcription factors. In various embodiments, the AAV vectors disclosed herein may comprise a construct that may create a homoeostatic feedback loop that may maintain expression levels of the protein of interest at a physiological level.

In some embodiments of the AAV vectors disclosed herein, genome editing machinery may be used to genetically modify cellular genome DNA or mRNA transcripts at a site-specific manner. Komor et al., Cell 168, 20-36 (2017); and Katrekar et al., Nature Methods 16:239-242, 2019. For example, some embodiments of the AAV vectors may include a CRISPR-associated enzyme such as Cas9, a DNA base editor, an RNA editase and/or guide RNA (gRNA) to modify nucleic acid in cells in a site-specific manner. In addition, AAV vectors may contain a homology repair template (HDR) for genome editing.

In various embodiments, the AAV vectors disclosed herein can comprise a nucleic acid that may include a leader sequence allowing secretion of the encoded protein. In some embodiments, fusion of the transgene of interest with a sequence encoding a secretion signal peptide (usually located at the N-terminal of secreted polypeptides) may allow the production of the therapeutic protein in a form that can be secreted from the transduced cell. Examples of such signal peptides include the albumin, the 3-glucuronidase, the alkaline protease or the fibronectin secretory signal peptides.

As described herein, effective and long-term expression of therapeutic proteins of interest in brain, heart, lung, skeletal muscle, kidney, spleen, or pancreas can be achieved with non-invasive techniques, through peripheral administration of certain AAV vectors, such as a non-AAV9 vector with AAV9 sequences. Such peripheral administration may include any administration route that does not necessitate direct injection into brain, heart, lung, skeletal muscle, kidney, spleen, or pancreas. More particularly, peripheral administration may include systemic injections, such as intramuscular, intravascular (such as intravenous,) intraperitoneal, intra-arterial, or subcutaneous injections. In some embodiments, peripheral administration also may include oral administration (see, e.g., WO96/40954), delivery using implants, (see, e.g., WO01/91803), or administration by instillation through the respiratory system, e.g., using sprays, aerosols or any other appropriate formulations.

In various embodiments, the desired doses of the AAV vectors may be adapted by the skilled artisan, e.g., depending on the disease condition, the subject, the treatment schedule, etc. In some embodiments, from $10^5$ to $10^{12}$ viral genomes are administered per dose, for example, from $10^6$ to $10^{11}$, from $10^7$ to $10^{11}$, or from $10^8$ to $10^{11}$. In other embodiments, exemplary doses for achieving therapeutic effects may include virus titers of at least about $10^5$, $10^6$, $10^7$, $10^8$, $10^9$, $10^{10}$ or $10^{11}$ viral genomes or more. Virus titer may also be expressed in terms of transducing units, which may be readily calculated by those of skill in the art.

In various embodiments, the AAV vectors disclosed herein may be administered in any suitable form, for instance, either as a liquid solution or suspension, as a solid form suitable for solution or suspension in liquid prior to injection, as a gel or as an emulsion. The vectors may be formulated with any appropriate and pharmaceutically acceptable excipient, carrier, adjuvant, diluent, etc. For instance, for injection, a suitable carrier or diluent may be an isotonic solution, a buffer, sterile and pyrogen-free water, or, for instance, a sterile and pyrogen-free phosphate-buffered saline solution. For inhalation, the carrier may be in particulate form.

The vectors may be administered in a "therapeutically-effective" amount, e.g., an amount that is sufficient to alleviate (e.g., decrease, reduce) at least one of the symptoms associated with a disease state, or to provide improvement in the condition of the subject.

In some embodiments, repeated administrations may be performed, for instance using the same or a different peripheral administration route and/or the same vector or a distinct vector.

ENUMERATED EMBODIMENTS

Embodiment 1: A nucleic acid comprising: a Parvoviridae genome flanked by ITR sequences, wherein the Parvoviridae genome comprises a Parvoviridae intron, a Parvoviridae cap gene, and a first polyadenylation signal in a first orientation; a first promoter in the first orientation that drives expression of the Parvoviridae cap gene in the presence of adenoviral helper functions; and a second promoter and a second polyadenylation signal in a second orientation that is antisense with respect to the first orientation, and wherein the second polyadenylation signal is located at a position that causes termination of antisense mRNA transcription of the Parvoviridae cap gene.

Embodiment 2: The nucleic acid of embodiment 1, wherein the second promoter is a cell type-specific promoter.

Embodiment 3: The nucleic acid of embodiment 1, wherein the second promoter is a ubiquitous promoter.

Embodiment 4: The nucleic acid of any of embodiments 1-3, wherein the Parvoviridae genome is an AAV genome comprising an AAV intron and an AAV cap gene Embodiment 5: The nucleic acid of embodiment 4, wherein the AAV cap gene is a wild-type AAV cap gene.

Embodiment 6: The nucleic acid of embodiment 5, wherein the AAV cap gene sequence is the AAV1, AAV2, AAV3, AAV4, AAV5, AAV6, AAV7, AAV8, AAV9, AAV10, AAV11, AAV12, AAV13 or other natural AAV isolate cap gene sequence.

Embodiment 7: The nucleic acid of embodiment 4, wherein the AAV cap gene is an engineered AAV cap gene.

Embodiment 8: The nucleic acid of embodiment 4, wherein the AAV cap gene is one of a library of diverse AAV cap genes.

Embodiment 9: A nucleic acid library comprising a plurality of nucleic acids of embodiment 4, wherein the nucleic acids comprise a plurality of unique AAV cap gene sequences.

Embodiment 10: The nucleic acid library of embodiment 9, wherein the nucleic acid library comprises greater than about $10^2$, $10^3$, $10^4$, $10^5$, $10^6$, $10^7$ or $10^8$ unique AAV cap gene sequences.

Embodiment 11: The nucleic acid of any of embodiments 1-8, further comprising a gene of interest in the second orientation.

Embodiment 12: The nucleic acid of any of embodiments 4-8 or 11, wherein the second polyadenylation signal is located within the AAV intron.

Embodiment 13: The nucleic acid of any of embodiments 4-8 or 11, wherein the second polyadenylation signal is located such that the cap gene is correctly translated into a full-length capsid protein in the first orientation and the cap gene is correctly transcribed into anti-sense mRNA that contains a full-length AAV cap gene coding sequence.

Embodiment 14: A method for identifying an AAV vector with a cap gene sequence that has increased ability to transduce cells from a tissue of interest when compared to at least one other AAV vector with a different cap gene sequence, the method comprising: Preparing a first-round AAV TRADE vector library by introducing the nucleic acid library of embodiment 9 or 10 into an AAV packaging cell line and recovering the first round AAV TRADE vector library from the packaging cell line; Injecting one or more animals with the first-round AAV TRADE vector library; Recovering cap gene sequences of AAV vectors that are enriched in cells of the tissue of interest in the animals; Preparing a second-round AAV TRADE nucleic acid library comprising recovered cap gene sequences of the enriched AAV vectors and introducing this library into an AAV packaging cell line and recovering the second round AAV TRADE vector library from the packaging cell line; Performing a second round of enrichment by injecting one or more animals with the second-round AAV TRADE vector library and recovering cap gene sequence that are enriched in cells of the tissue of interest in the animals; and Identifying enriched AAV cap gene sequences after the first-round enrichment, after the second-round enrichment, and after any subsequent rounds of enrichment.

Embodiment 15: A method for producing an AAV TRADE vector or an AAV TRADE vector library comprising: Introducing the nucleic acid of any of embodiments 4-8 or 11-13, or the nucleic acid library of embodiment 9 or 10, into an AAV packaging cell line and recovering the AAV TRADE vector or AAV TRADE vector library from the packaging cell line.

Embodiment 16: A method for determining a sequence of a novel cap gene of an AAV vector that has increased ability to transduce cells from a tissue of interest comprising: Identifying the AAV vector according to the method of embodiment 14; Recovering antisense mRNA comprising the cap gene sequence; and determining the novel cap gene sequence.

Embodiment 17: The method of embodiment 16, wherein the antisense mRNA is recovered using RT-PCR.

Embodiment 18: The method of either embodiment 16 or 17, further comprising the step of determining the cap gene sequence Embodiment 19: An AAV vector comprising the nucleic acid of any of embodiments 4-8 or 11-13.

Embodiment 20: A nucleic acid comprising: a Parvoviridae genome flanked by ITR sequences, wherein the Parvoviridae genome comprises a Parvoviridae intron, a Parvoviridae cap gene, and a first polyadenylation signal in a first orientation; a first promoter in the first orientation that drives expression of the Parvoviridae cap gene in the presence of adenoviral helper functions; and a second promoter in the first orientation that drives expression of the Parvoviridae cap gene in the absence of adenoviral helper functions.

Embodiment 21: The nucleic acid of embodiment 20, wherein the second promoter is a cell type-specific promoter.

Embodiment 22: The nucleic acid of embodiment 20, wherein the second promoter is a ubiquitous promoter.

Embodiment 23: The nucleic acid of any of embodiments 20-22, wherein the Parvoviridae cap gene is a wild-type AAV cap gene.

Embodiment 24: The nucleic acid of embodiment 23, wherein the AAV cap gene sequences is the AAV1, AAV2, AAV3, AAV4, AAV5, AAV6, AAV7, AAV8, AAV9, AAV10, AAV11, AAV12, AAV13 or other natural AAV isolate cap gene sequence.

Embodiment 25: The nucleic acid of any of embodiments 20-22, wherein the Parvoviridae cap gene is an engineered AAV cap gene.

Embodiment 26: The nucleic acid of any of embodiments 20-25, wherein the Parvoviridae cap gene is one of a library of diverse AAV cap genes.

Embodiment 27: A nucleic acid library comprising a plurality of nucleic acids of embodiment 20, wherein the nucleic acids comprise a plurality of unique Parvoviridae cap gene sequences.

Embodiment 28: The nucleic acid library of embodiment 27, wherein the nucleic acid library comprises greater than about $10^2$, $10^3$, $10^4$, $10^5$, $10^6$, $10^7$ or $10^8$ unique AAV cap gene sequences.

Embodiment 29: The nucleic acid of any of embodiments 20-26, further comprising a gene of interest.

Embodiment 30: A method for identifying an AAV vector with a cap gene sequence that has increased ability to transduce cells from a tissue of interest when compared to at least one other AAV vector with a different cap gene sequence, the method comprising: Preparing a first-round AAV TRADE vector library by introducing the nucleic acid library of embodiment 27 or 28 into an AAV packaging cell line and recovering the first round AAV TRADE vector library from the packaging cell line; Injecting one or more animals with the first-round AAV TRADE vector library; Recovering cap gene sequences of AAV vectors that are enriched in cells of the tissue of interest in the animals; preparing a second-round AAV TRADE nucleic acid library comprising recovered cap gene sequences of the enriched AAV vectors and introducing this library into an AAV packaging cell line and recovering the second round AAV TRADE vector library from the packaging cell line; Performing a second round of enrichment by injecting one or more animals with the second-round AAV TRADE vector library and recovering cap gene sequence that are enriched in cells of the tissue of interest in the animals; and Identifying enriched AAV cap gene sequences after the first-round enrichment, after the second-round enrichment, and after any subsequent rounds of enrichment.

Embodiment 31: A method for producing an AAV TRADE vector or an AAV TRADE vector library comprising: Introducing the nucleic acid of any of embodiments 23-26 or 29, or the nucleic acid library of embodiment 27 or 28, into an AAV packaging cell line and recovering the AAV TRADE vector or AAV TRADE vector library from the packaging cell line.

Embodiment 32: A method for determining a sequence of a novel cap gene of an AAV vector that has increased ability to transduce cells from a tissue of interest comprising: Identifying the AAV vector according to the method of embodiment 30; Recovering sense mRNA comprising the cap gene sequence; and Determining the novel cap gene sequence.

Embodiment 33: The method of embodiment 32, wherein the sense mRNA is recovered using RT-PCR.

Embodiment 34: The method of either embodiment 32 or 33, further comprising the step of determining the cap gene sequence.

Embodiment 35: An AAV vector comprising the nucleic acid of any of embodiments 23-26 or 29.

Embodiment 36: The nucleic acid of any of embodiments 1-8 or 11-13, further comprising at least one mRNA splicing suppressing mutation in the second orientation.

Embodiment 37: The nucleic acid of embodiment 36, wherein the at least one mRNA splicing suppressing mutation comprises an alteration of one or more nucleotides located within ten nucleotides of the splice donor and/or splice acceptor site.

Embodiment 38: The nucleic acid of embodiment 36 or 37, wherein the alteration does not change the amino acid sequence encoded by the AAV cap gene.

Embodiment 39: An AAV cap ORF sequence comprising one or more following mutations in the exon-intron junctions at splicing donor sites:

```
                                          (SEQ ID NO: 199)
AAV1 VP1 cap ORF 1009-CTTAC(junction)CAGCA-1018*

(SEQ ID NO: 199)
AAV3 VP1 cap ORF 1006-CTTAC(junction)CAGCA-1015*

(SEQ ID NO: 200)
AAV1 VP1 cap ORF 1228-TTTAC(junction)CTTCA-1237

(SEQ ID NO: 201)
AAV3 VP1 cap ORF 1237-TATAC(junction)CTTCG-1246

(SEQ ID NO: 202)
AAV1 VP1 cap ORF 1331-ATTAC(junction)CTGAA-1340

(SEQ ID NO: 203)
AAV1 VP1 cap ORF 1434-GCTAC(junction)CTGGA-1443

(SEQ ID NO: 204)
AAV1 VP1 cap ORF 1502-TTTAC(junction)CTGGA-1510

(SEQ ID NO: 205)
AAV1 VP1 cap ORF 1803-ATTAC(junction)CTGGC-1812

(SEQ ID NO: 206)
AAV3 VP1 cap ORF 1803-CTTAC(junction)CTGGC-1812

(SEQ ID NO: 207)
AAV1 VP1 cap ORF 1835-TGTAC(junction)CTGCA-1844

(SEQ ID NO: 208)
AAV1 VP1 cap ORF 2189-GTTAC(junction)CTTAC-2198

(SEQ ID NO: 209)
AAV9 VP1 cap ORF 2189-GATAC(junction)CTGAC-2198

(SEQ ID NO: 210)
AAV1 VP1 cap ORF 2194-CTTAC(junction)CCGTC-2203

(SEQ ID NO: 211)
AAV3 VP1 cap ORF 2194-CTCAC(junction)ACGAA-2203.
(*Although the nucleotide numbers are different,
they are corresponding nucleotides of the AAV
cap ORFs in sequence alignment.)
```

Embodiment 40: An AAV cap ORF sequence comprising one or more following mutations in the exon-intron junctions at splicing donor sites:

```
                                          (SEQ ID NO: 212)
AAV1 VP1 cap ORF 305-AGCGT(junction)CTGCA-314

(SEQ ID NO: 213)
AAV1 VP1 cap ORF 414-GGCTC(junction)CTGGA-423

(SEQ ID NO: 213)
AAV3 VP1 cap ORF 414-GGCTC(junction)CTGGA-423

(SEQ ID NO: 214)
AAV1 VP1 cap ORF 495-GCCCG(junction)CTAAA-504

(SEQ ID NO: 214)
AAV9 VP1 cap ORF 495-GCCCG(junction)CTAAA-504

(SEQ ID NO: 215)
AAV3 VP1 cap ORF 1133-TCACC(junction)CTGAA-1142

(SEQ ID NO: 216)
AAV1 VP1 cap ORF 1181-ACTGC(junction)CTGGA-1190

(SEQ ID NO: 202)
AAV1 VP1 cap ORF 1331-ATTAC(junction)CTGAA-1340**

(SEQ ID NO: 217)
AAV3 VP1 cap ORF 1328-ACTAC(junction)CTGAA-1337**

(SEQ ID NO: 218)
AAV1 VP1 cap ORF 1464-CGTTT(junction)CTAAA-1473

(SEQ ID NO: 219)
AAV1 VP1 cap ORF 1653-AAACA(junction)CTGCA-1662

(SEQ ID NO: 220)
AAV1 VP1 cap ORF 2054-GGGAG(junction)CTGCA-2063

(SEQ ID NO: 463)
AAV3 VP1 cap ORF 2054-GGGAG(junction)CTACA-2063
(**Although the nucleotide numbers are different,
they are corresponding nucleotides of the AAV
cap ORFs in sequence alignment.)
```

Embodiment 41: An AAV cap ORF sequence comprising one or more following mutations in the exon-intron junctions at splicing donor or splicing acceptor sites:

```
Splice donors
                                          (SEQ ID NO: 199)
AAV1 VP1 cap ORF 1009-CTTAC(junction)CAGCA-1018*

(SEQ ID NO: 199)
AAV3 VP1 cap ORF 1006-CTTAC(junction)CAGCA-1015*

(SEQ ID NO: 200)
AAV1 VP1 cap ORF 1228-TTTAC(junction)CTTCA-1237

(SEQ ID NO: 201)
AAV3 VP1 cap ORF 1237-TATAC(junction)CTTCG-1246

(SEQ ID NO: 202)
AAV1 VP1 cap ORF 1331-ATTAC(junction)CTGAA-1340

(SEQ ID NO: 203)
AAV1 VP1 cap ORF 1434-GCTAC(junction)CTGGA-1443

(SEQ ID NO: 204)
AAV1 VP1 cap ORF 1502-TTTAC(junction)CTGGA-1510

(SEQ ID NO: 205)
AAV1 VP1 cap ORF 1803-ATTAC(junction)CTGGC-1812

(SEQ ID NO: 206)
AAV3 VP1 cap ORF 1803-CTTAC(junction)CTGGC-1812

(SEQ ID NO: 207)
AAV1 VP1 cap ORF 1835-TGTAC(junction)CTGCA-1844

(SEQ ID NO: 208)
AAV1 VP1 cap ORF 2189-GTTAC(junction)CTTAC-2198

(SEQ ID NO: 209)
AAV9 VP1 cap ORF 2189-GATAC(junction)CTGAC-2198

(SEQ ID NO: 210)
AAV1 VP1 cap ORF 2194-CTTAC(junction)CCGTC-2203

(SEQ ID NO: 211)
AAV3 VP1 cap ORF 2194-CTCAC(junction)ACGAA-2203

Splice acceptor
                                          (SEQ ID NO: 212)
AAV1 VP1 cap ORF 305-AGCGT(junction)CTGCA-314
```

-continued

AAV1 VP1 cap ORF 414-GGCTC(junction)CTGGA-423 (SEQ ID NO: 213)

AAV3 VP1 cap ORF 414-GGCTC(junction)CTGGA-423 (SEQ ID NO: 213)

AAV1 VP1 cap ORF 495-GCCCG(junction)CTAAA-504 (SEQ ID NO: 214)

AAV9 VP1 cap ORF 495-GCCCG(junction)CTAAA-504 (SEQ ID NO: 214)

AAV3 VP1 cap ORF 1133-TCACC(junction)CTGAA-1142 (SEQ ID NO: 215)

AAV1 VP1 cap ORF 1181-ACTGC(junction)CTGGA-1190 (SEQ ID NO: 216)

AAV1 VP1 cap ORF 1331-ATTAC(junction)CTGAA-1340** (SEQ ID NO: 202)

AAV3 VP1 cap ORF 1328-ACTAC(junction)CTGAA-1337** (SEQ ID NO: 217)

AAV1 VP1 cap ORF 1464-CGTTT(junction)CTAAA-1473 (SEQ ID NO: 218)

AAV1 VP1 cap ORF 1653-AAACA(junction)CTGCA-1662 (SEQ ID NO: 219)

AAV1 VP1 cap ORF 2054-GGGAG(junction)CTGCA-2063 (SEQ ID NO: 220)

AAV3 VP1 cap ORF 2054-GGGAG(junction)CTACA-2063. (SEQ ID NO: 463)

EXAMPLES

The following examples are for illustration only. In light of this disclosure, those of skill in the art will recognize that variations of these examples and other embodiments of the disclosed subject matter are enabled without undue experimentation.

Figure 2A:
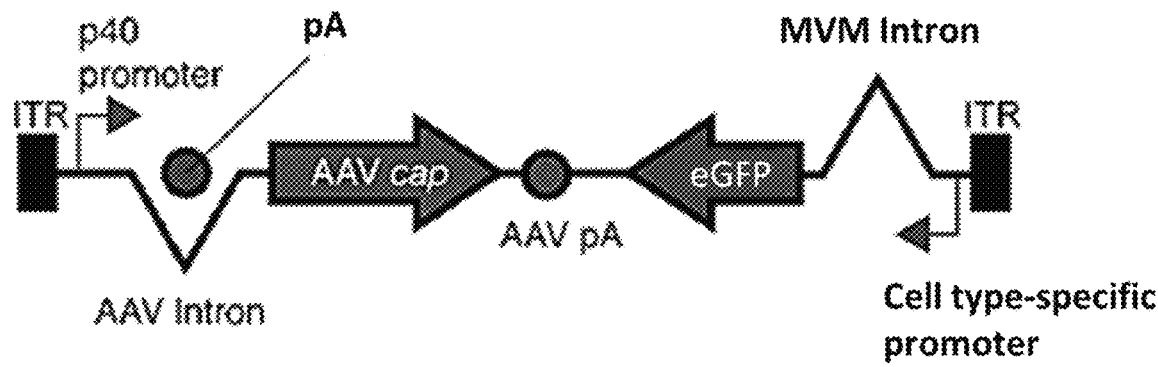
FIGS. 2A-2B: Principle of TRADE.
Figure 2B:
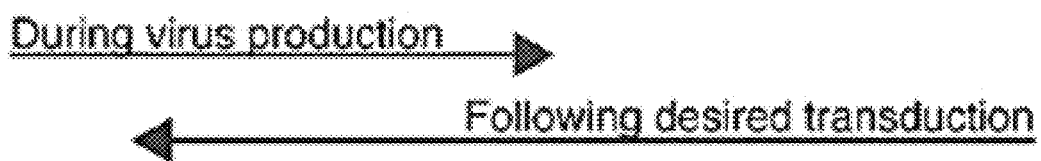

We applied the TRADE system in both C57BL/6J mice and a rhesus macaque in order to identify novel AAV capsids that efficiently transduce brain neurons following systemic delivery. The TRADE system utilizes a plasmid construct containing an overlapping bicistronic AAV genome flanked by ITR sequences (FIG. 2A). In the sense direction, the AAV2 p40 promoter drives expression of the AAV cap gene to facilitate efficient production of viral particles (FIG. 2B). In the antisense direction, a cell type-specific enhancer-promoter (e.g. the human synapsin I (hSynI) enhancer-promoter) drives expression of transcripts encoding GFP and the antisense cap sequence (FIG. 2B), terminating at a polyadenylation signal (poly A) embedded in the intron present in the AAV2 genome. Utilizing the TRADE construct as a cloning backbone, we generated an AAV library based on the liver-detargeted AAV9-N272A (PCT/US2017/068050) cap gene platform that contained random 8-mer peptides with glycine-serine linkers (5'-GGGS; 3'-GGGGS) substituted at the position Q588 in the AAV9 capsid. In vivo selection in a specific cell type (e.g. neurons) was performed by recovering capsid sequences as antisense cap ORF mRNA from brain tissue by RT-PCR. This method ensures that recovered sequences are only derived from AAV variants that are capable of mediating RNA expression in infected cells of our interest. When the hSynI enhancer-promoter is used, only sequences of AAV capsids that are capable of transducing neurons can be retrieved, thus enabling neuron-specific selection of AAV capsids.

Figure 3A:
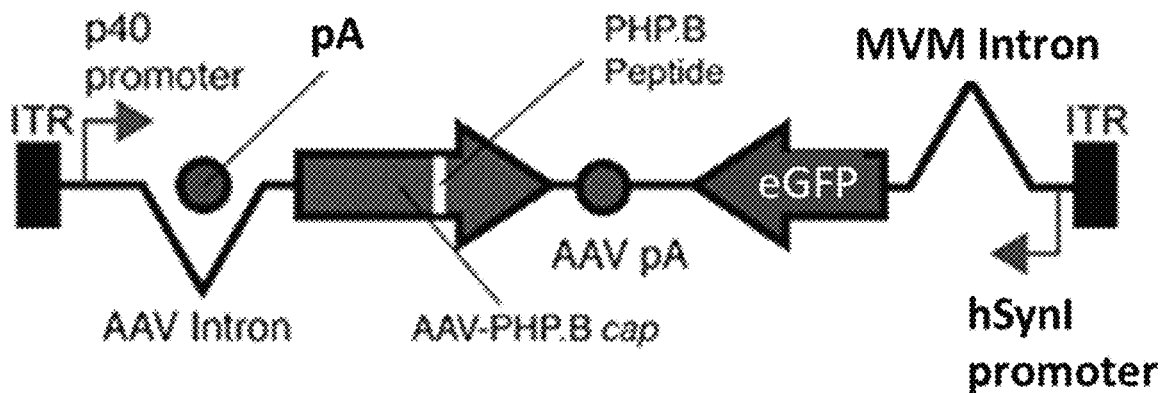
FIGS. 3A-3G: Validation of the TRADE system targeting brain neurons.
Figure 3B:
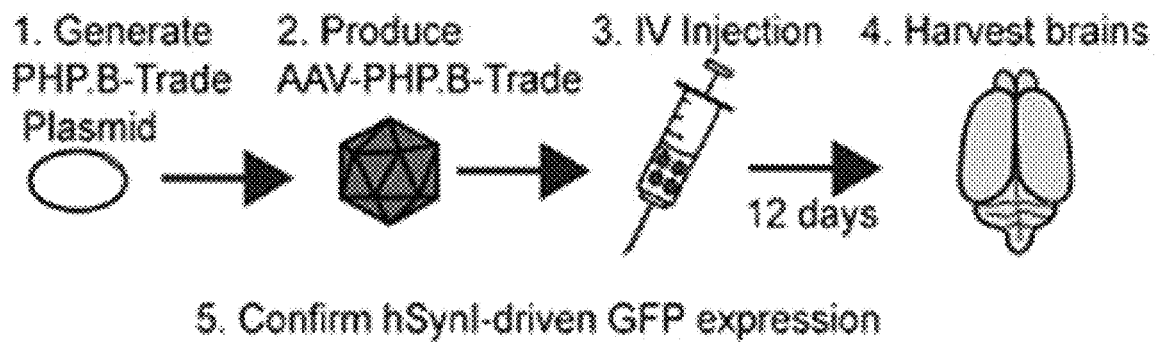
Figure 3C:
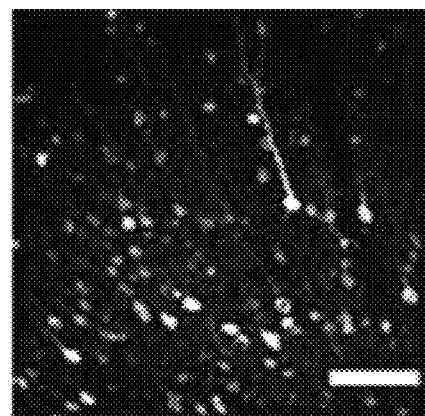
Figure 3D:
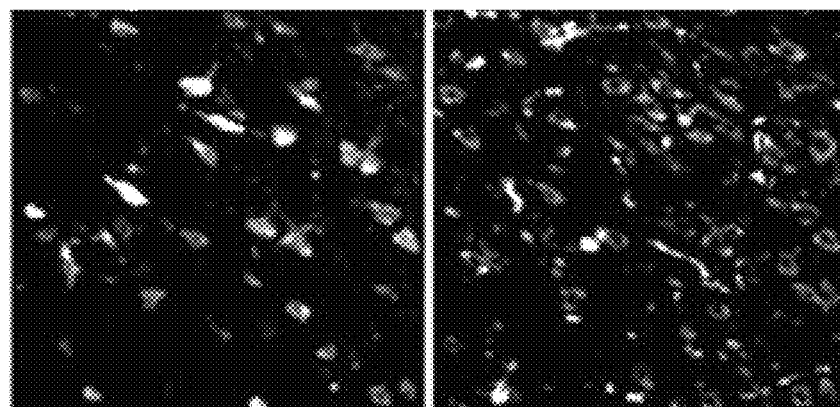
Figure 3E:
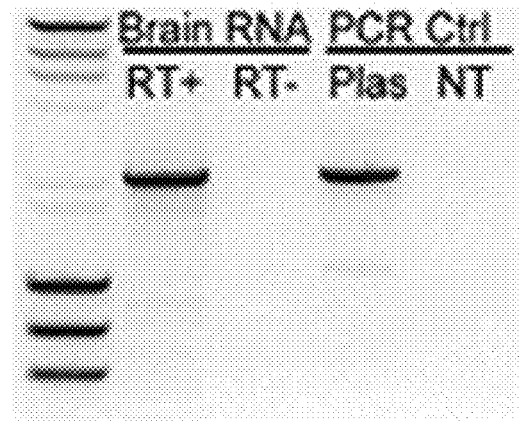
Figure 3F:
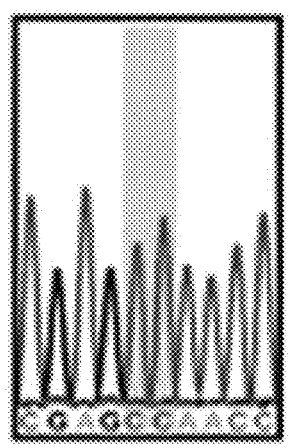
Figure 3G:
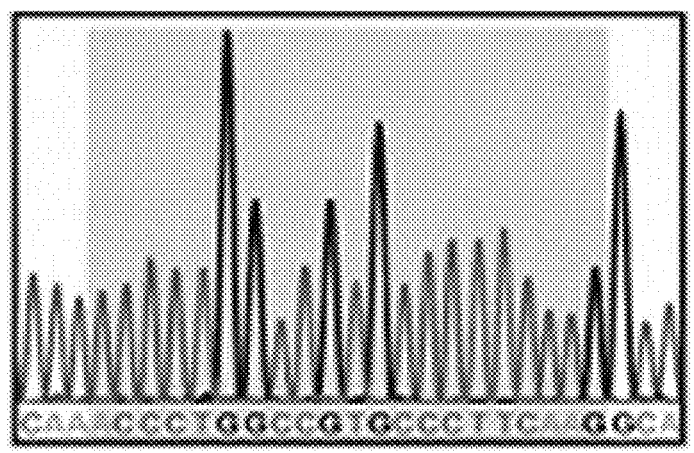

We first tested the ability of the TRADE system to recover the sequence of the AAV cap gene from cell type-specific antisense mRNA using an AAV-PHP.B-hSynI-GFP-TRADE vector (FIGS. 3A-3G). A hSynI enhancer-promoter-driven GFP expression cassette was incorporated in the AAV-PHP.B capsid gene-containing AAV vector genome in the TRADE configuration (FIG. 3A). This vector genome was packaged into the AAV-PHP.B capsid, and the resulting AAV vector was injected intravenously into two 8-week-old male C57BL/6J mice (FIG. 3B). Twelve days after injection, brain tissue was harvested. Tissue fixed with 4% paraformaldehyde was analyzed by immunofluorescence microscopy. Unfixed tissue was utilized for RNA extraction and RT-PCR analysis. We confirmed that eGFP was expressed only in neurons (FIG. 3C and FIG. 3D), indicating that the antisense mRNA transcribed from the cap gene is expressed in a cell type-specific manner. We recovered antisense mRNA of the cap gene efficiently by RT-PCR (FIG. 3E). Sanger sequencing of a splice junction unique to the antisense mRNA confirmed that RT-PCR products were indeed derived from the hSynI enhancer-promoter-driven antisense mRNA (FIG. 3F). In addition, Sanger sequencing confirmed the sequence of the PHP.B peptide insertion (FIG. 3F). Together, these observations established the ability of the TRADE system to successfully recover the AAV cap sequence from the hSynI enhancer-promoter-driven antisense mRNA expressed in AAV vector-transduced brain neurons.

Figure 14A:
Figure 14B:
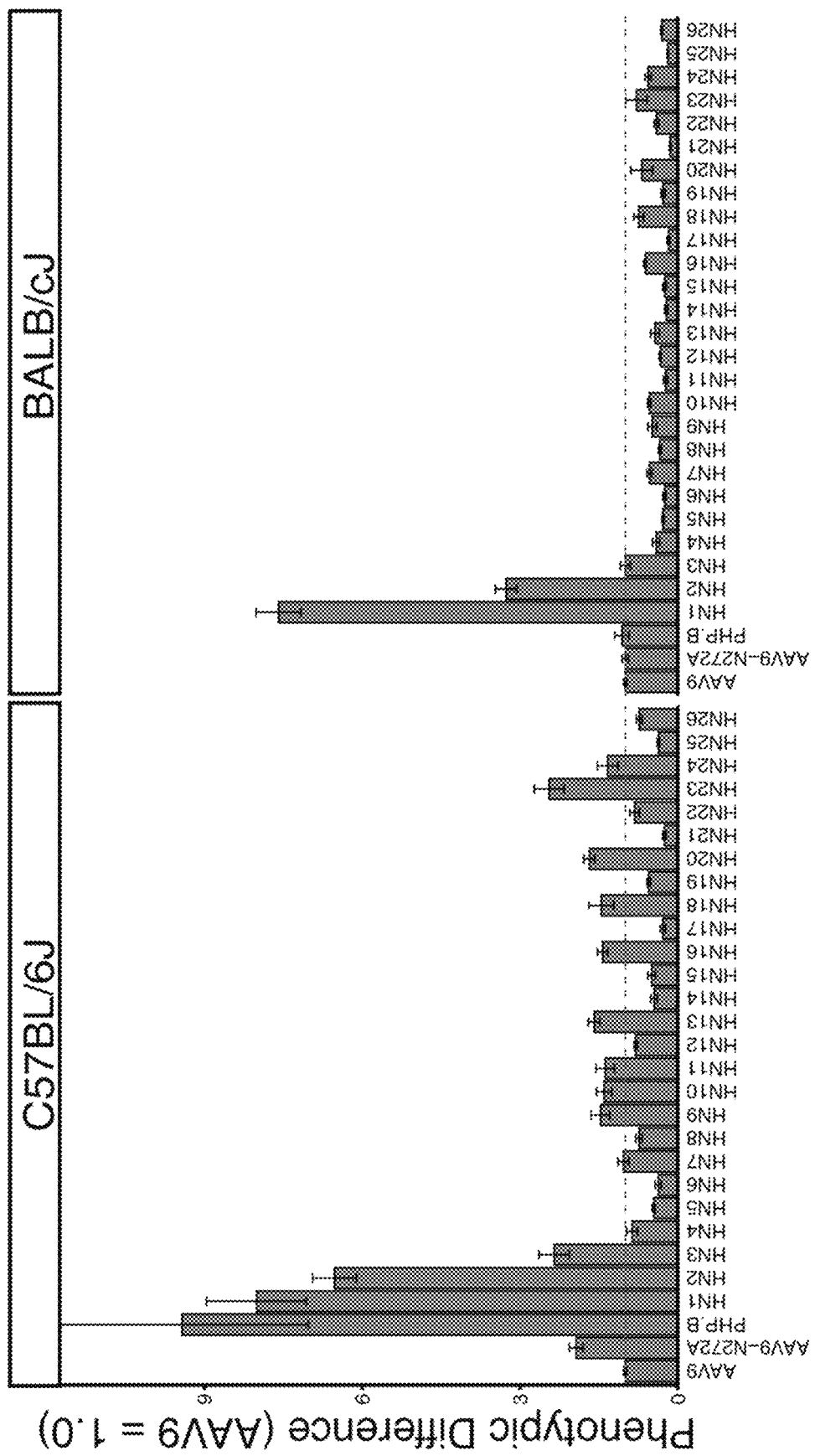
Figure 14C:
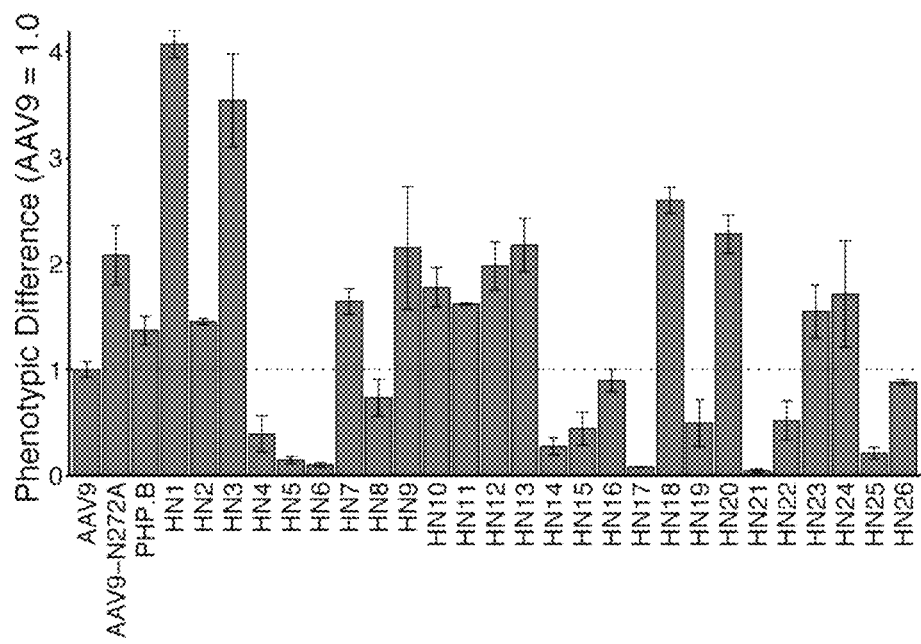
Figure 14D:
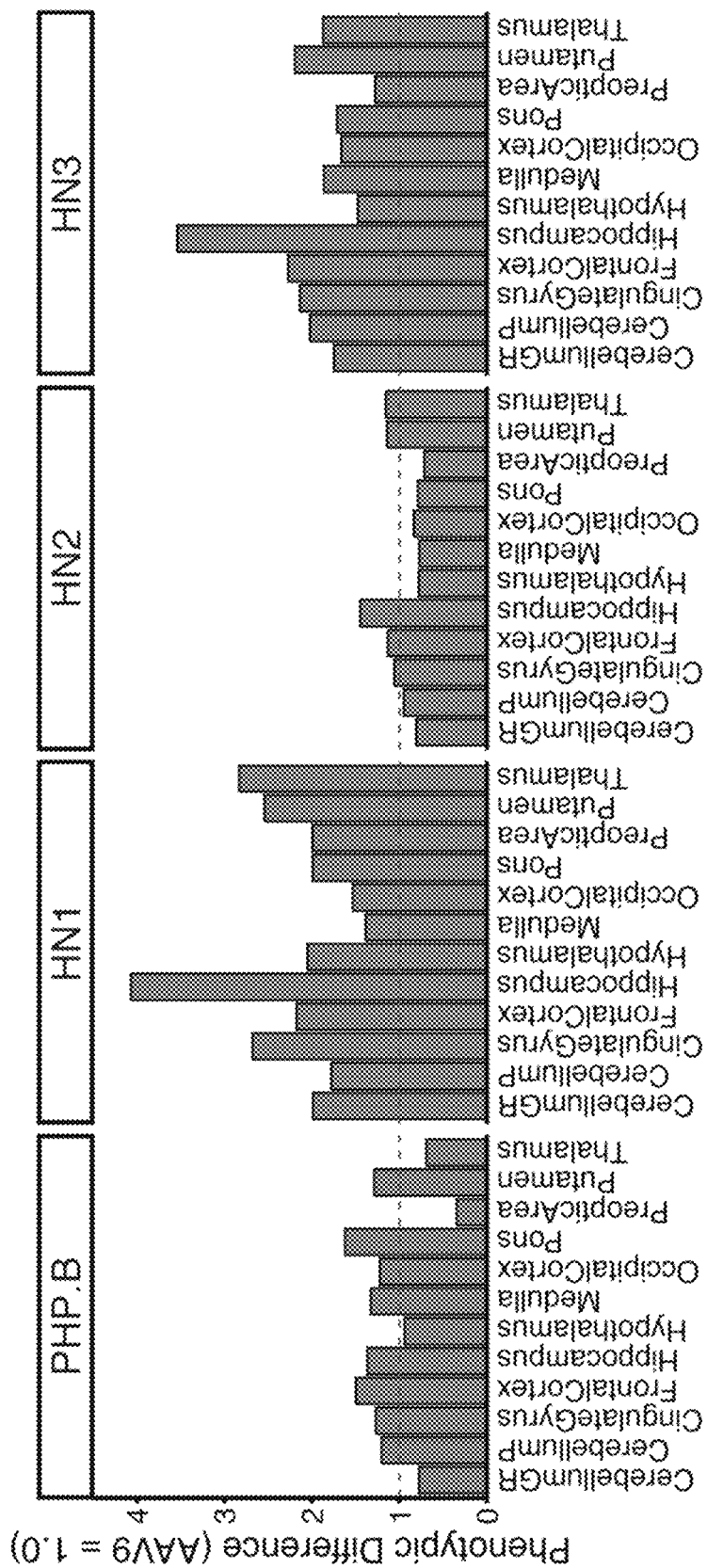
Figure 17A:
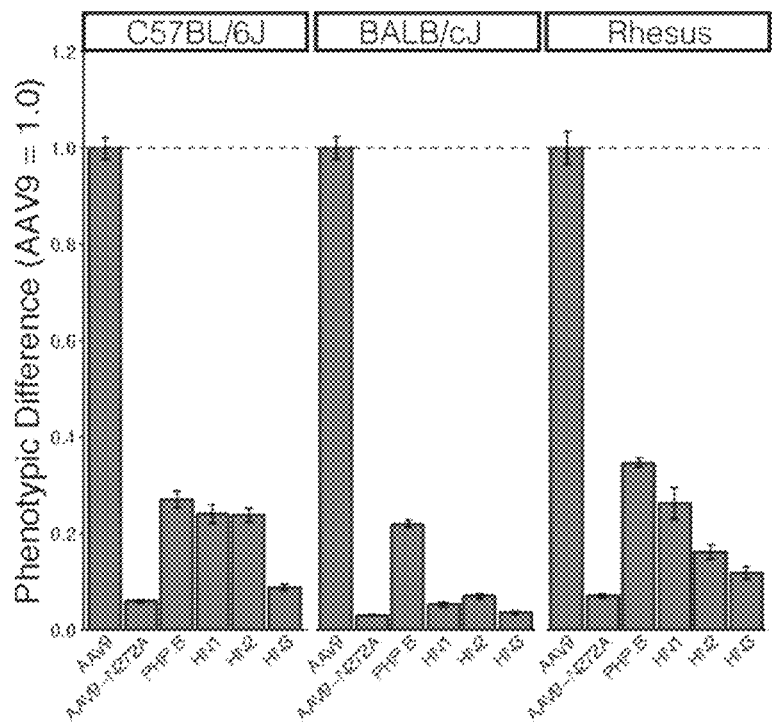
Figure 17B:
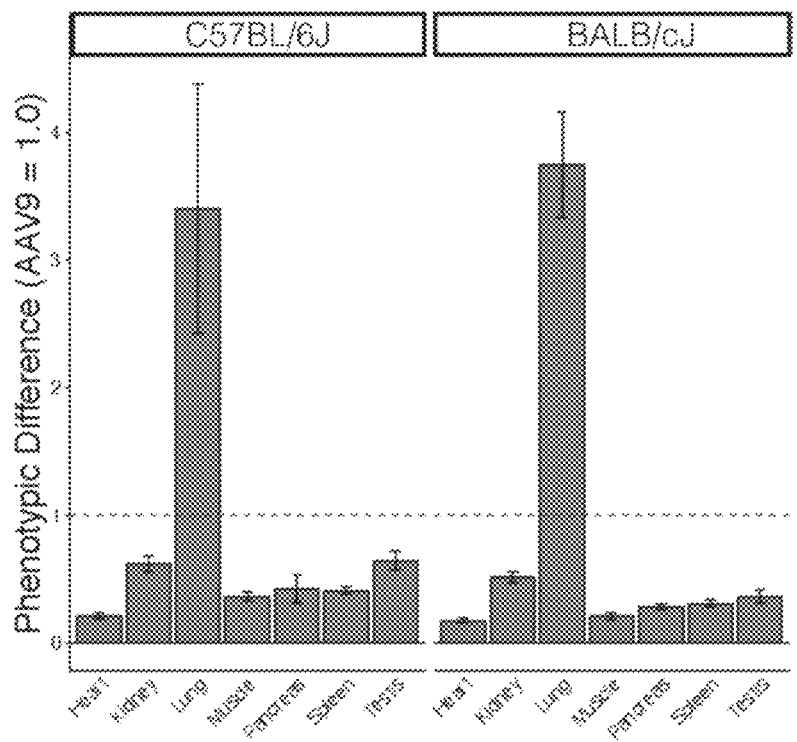
Figure 17C:
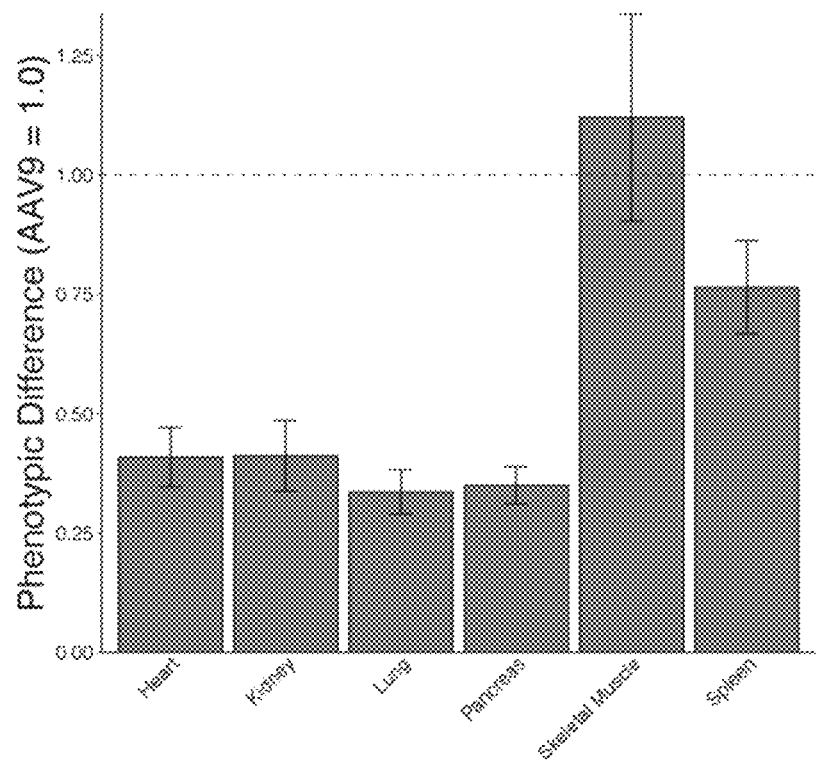
Figure 17D:
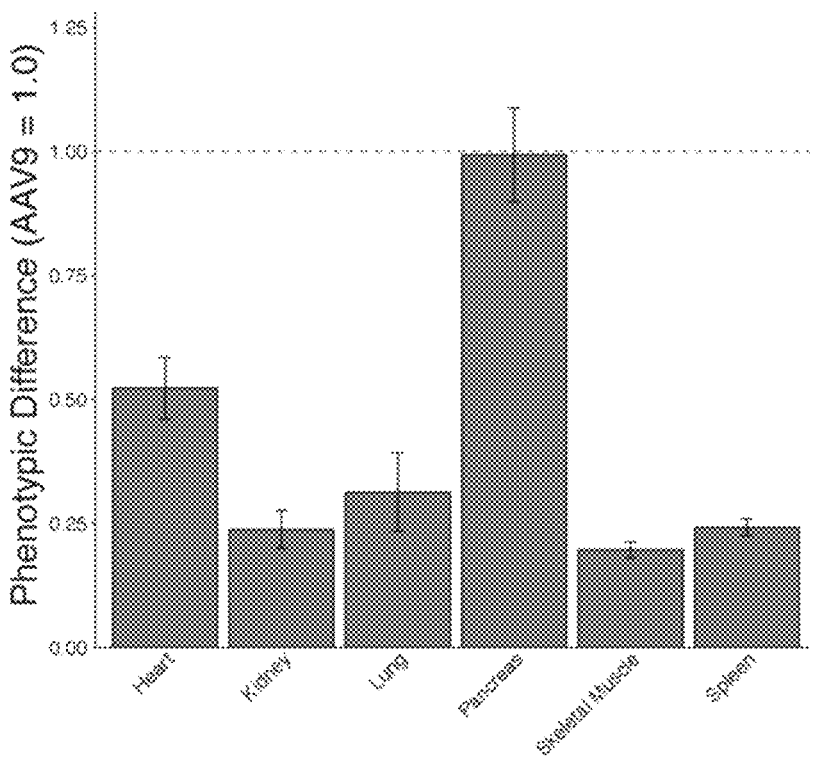

With the successful establishment of the TRADE system, we performed two AAV capsid directed evolution experiments; one used 8-week-old male C57BL/6J mice and the other used one 8-month-old male rhesus macaque. We produced an AAV9-N272A-hSynI-GFP-TRADE-Lib library composed of AAV9-derived mutant capsids that have a GGGS($N_8$)GGGGS (SEQ ID NO:2) peptide insertion at the position of Q588 where $N_8$ represents a random 8-mer peptide encoded by $(NNK)_8$. For the peptide insertion, Q588 was substituted with each peptide sequence. The diversity of the AAV library was at least $10^7$. In the mouse directed evolution experiment, we infused the AAV library via the tail vein at a dose of $3\times10^{11}$ vector genomes (vg) per mouse. For the second round of selection, we injected the AAV library at a dose of $1\times10^{12}$, $1\times10^{11}$, $1\times10^{10}$, or $1\times10^9$ vector genomes (vg) using two mice. For the third round of selection, we injected the AAV library at a dose of $1\times10^{11}$ vg using two mice. We harvested brain tissues twelve days after injection, and separated them into three regions, i.e., the cerebrum, the cerebellum and the brain stem. Only the cerebrum samples were used for the directed evolution experiments. We extracted total RNA from the cerebrum, reverse-transcribed the RNA using an oligo dT primer, and amplified the peptide region including the flanking regions by a pair of the cap gene-specific PCR primers. The RT-PCR products were then used to create the next AAV9-N272A-hSynI-TRADE-Lib plasmid library, which was subsequently used to produce the next AAV9-N272A-hSynI-TRADE-Lib virus library. For the second and third round selection, we packaged an AAV9-N272A-hSynI-TRADE-Lib genome that was devoid of the GFP ORF. In the non-human primate directed evolution experiment, we infused the AAV9-N272A-hSynI-GFP-TRADE-Lib library via the saphenous vein at a dose of $2.0\times10^{12}$ vg per kg. Twelve days post-injection, the whole brain was harvested and sliced using a brain matrix, treated with RNAlater (Thermo Fisher Scientific), and stored frozen. Total RNA was then extracted from the following brain regions: frontal cortex, occipital cortex, cerebellum (Purkinje and granular layers), medulla, pons, frontal cortex, hypothalamus, thalamus, cingulate gyrus, caudate nucleus, putamen, hippocampus, and preoptic area. We retrieved the peptide sequences by RT-PCR in the same manner as described above except that we performed nested PCR to obtain PCR products sufficient for the downstream Illumina and Sanger sequencing procedures. For some samples, we cloned the first PCR products directly into a plasmid backbone without performing nested PCR for Sanger sequencing. Following three rounds of selection in mice (Table 1) and one round of selection in non-human primate, we identified a number of potentially transduction-enhancing peptides inserted into the AAV9 capsids (Table 2). We then generated a barcoded AAV library and utilized DNA/RNA Barcode-Seq technology, previously developed in the Nakai lab (Adachi et al. *Nat Commun* 5, 3075 (2014); and PCT/US2017/068050), to compare the transduction efficiency, tropism/biodistribution, and pharmacokinetics of 26 selected novel AAV variants (Table 3) following intravenous administration in two commonly used mouse lines (C57BL/6J and BALB/cJ) and one rhesus macaque. As a result, we have found: (1) Some of the novel variants identified by TRADE technology, in particular AAV9-N272A-TTNLAKNS (HN1) and AAV9-N272A-QQNGTRPS (HN2), performed up to 8 times better than AAV9 in the brain of C57BL/6J mice (FIG. 14B and FIG. 14C). For HNx designation, please refer to *Table* 3. (2) *As previously reported* by Hordeaux et al. (Hordeaux et al. 2018), AAV-PHP.B transduced the brain of BALB/cJ mice only at a level comparable to or lower than that of AAV9 (FIG. 14B and FIG. 14C), demonstrating a mouse strain dependency for AAV-PHP.B's robust neurotropic enhancement. (3) In contrast, AAV9-N272A-TTNLAKNS (HN1) and AAV9-N272A-QQNGTRPS (HN2) retained robust neuronal transduction in BALB/cJ mice showing up to 7 times better transduction than AAV9 (FIG. 14B). (4) In a rhesus macaque, many of the novel AAV mutants showed enhanced neuronal transduction, up to 4-fold greater than AAV9 in certain brain regions, while AAV-PHP.B transduced non-human primate brain similarly to or lower than AAV9. In particular, AAV9-N272A-TTNLAKNS (HN1) transduced the non-human primate brain best in multiple brain regions (FIG. 14C and FIG. 14D). (5) All of the AAV9-N272A-derived variants including HN1, HN2 and HN3 showed varying degrees of liver-detargeting properties in mice and rhesus macaques (FIG. 17A). (6) AAV9-N272A-TTNLAKNS (HN1) and AAV9-N272A-QQNGTRPS (HN2) can transduce cells with the hSynI enhancer-promoter transcriptional activity in the lung up to 17 times better than AAV9 in mice (FIG. 17B, Tables 4 and 6). (7) AAV9-N272A-TTNLAKNS (HN1) exhibits vector genome dissemination to peripheral organs to a lesser degree compared to AAV9 (FIG. 17C and FIG. 17D). The AAV Barcode-Seq data are summarized in Tables 4 to 9. Representative data presented in Tables 4 to 9 are also shown in a graph format in FIG. 14B, FIG. 14C and FIG. 17A, FIG. 17B, FIG. 17C, and FIG. 17D.

TABLE 1

Peptide sequences identified by the hSyn1-TRADE system using an AAV9-N272N-GGGS($N_8$)GGGGS library targeting mouse brain neurons.

| 1st round | 2nd round | 3rd round |
|---|---|---|
| ADKPPGLS SEQ ID NO: 3 | APTNFAHP SEQ ID NO: 97 | AGAAYTPA (2) SEQ ID NO: 150 |
| AGEDGSSR SEQ ID NO: 4 | AQTNLAAG SEQ ID NO: 98 | APSVSREK (2) SEQ ID NO: 151 |
| ALGTATQR SEQ ID NO: 5 | ASLPNLGQ SEQ ID NO: 99 | DYMHKTGL SEQ ID NO: 152 |
| ALNTALVE SEQ ID NO: 6 | DYMHNTGL SEQ ID NO: 100 | EEDAQLLI (2) SEQ ID NO: 14 |
| AMVRLTHN SEQ ID NO: 7 | DYMHTTGL SEQ ID NO: 101 | ENKSAPLP SEQ ID NO: 18 |
| ASRDPSAT SEQ ID NO: 8 | ERNAWHAG SEQ ID NO: 102 | GDYTVQRP SEQ ID NO: 107 |
| DANDARQR SEQ ID NO: 9 | ETQATPMP SEQ ID NO: 103 | GGMNETTR SEQ ID NO: 153 |
| DLARMAAA SEQ ID NO: 10 | EWEDSARS SEQ ID NO: 104 | GGSAFVTG SEQ ID NO: 154 |
| DQGSITAH SEQ ID NO: 11 | FTGDTDTL SEQ ID NO: 105 | GGSPLAHP SEQ ID NO: 21 |
| DRTPGVNV SEQ ID NO: 12 | FTNRTSTT SEQ ID NO: 106 | GNSHTGSS SEQ ID NO: 155 |
| DTDTLSPG SEQ ID NO: 13 | GDYTVQRP SEQ ID NO: 107 | GPQEGSER (2) SEQ ID NO: 109 |
| EEDAQLLI SEQ ID NO: 14 | GGLRTDYG SEQ ID NO: 108 | GQRGLPIA SEQ ID NO: 27 |
| EKLNDWPT SEQ ID NO: 15 | GGSPLAHP SEQ ID NO: 21 | GSNHTQSL SEQ ID NO: 110 |
| ELNSARQV SEQ ID NO: 16 | GKQPVQPY SEQ ID NO: 24 | HQVTSSGA (4) SEQ ID NO: 33 |
| ELQSFAGL SEQ ID NO: 17 | GPQEGSER SEQ ID NO: 109 | LEQQRGAS SEQ ID NO: 113 |
| ENKSAPLP SEQ ID NO: 18 | GSNHTQSL SEQ ID NO: 110 | LERNRDSD SEQ ID NO: 39 |
| ERTAVKGN SEQ ID NO: 19 | GTPQTTKE SEQ ID NO: 29 | LLVTARSH (3) SEQ ID NO: 44 |
| GGIQTVVT SEQ ID NO: 20 | HDRDTRQA SEQ ID NO: 111 | MESQRANS (2) SEQ ID NO: 117 |
| GGSPLAHP SEQ ID NO: 21 | LDQNRRPQ SEQ ID NO: 112 | MSGQGYQA (2) SEQ ID NO: 50 |
| GGTAAQGV SEQ ID NO: 22 | LEQQRGAS SEQ ID NO: 113 | NSARTQLS SEQ ID NO: 156 |
| GKMASGSL SEQ ID NO: 23 | LERNRDSD SEQ ID NO: 39 | PLTILNRH SEQ ID NO: 157 |
| GKQPVQPY SEQ ID NO: 24 | LGGNAQGL SEQ ID NO: 114 | QGTRTNPP SEQ ID NO: 158 |
| GNPHTGST SEQ ID NO: 25 | LLVTTRSH SEQ ID NO: 115 | QQNGTRPS (4) SEQ ID NO: 128 |
| GPTLGGSG SEQ ID NO: 26 | LVTNTTR SEQ ID NO: 116 | QSGDSALN (3) SEQ ID NO: 67 |
| GQRGLPIA SEQ ID NO: 27 | MESQRANS SEQ ID NO: 117 | QSSAMPRN (2) SEQ ID NO: 159 |

TABLE 1-continued

Peptide sequences identified by the hSyn1-TRADE system using an AAV9-N272N-GGGS(N$_8$)GGGGS library targeting mouse brain neurons.

| 1st round | 2nd round | 3rd round |
|---|---|---|
| GREPRRLH SEQ ID NO: 28 | MISQTLMA SEQ ID NO: 118 | SATISLQV SEQ ID NO: 136 |
| GTPQTTKE SEQ ID NO: 29 | MMSQSLRA SEQ ID NO: 119 | SHNSQPVA SEQ ID NO: 160 |
| GVTERPNR SEQ ID NO: 30 | NNVQSALN SEQ ID NO: 120 | SHTNLRDT SEQ ID NO: 137 |
| HLGDNLAR SEQ ID NO: 31 | NSARTQLS SEQ ID NO: 121 | SSGYLTAN SEQ ID NO: 139 |
| HPGSGAGP SEQ ID NO: 32 | PQWNRTPL SEQ ID NO: 122 | TAQGAAFR (4) SEQ ID NO: 161 |
| HQVTSSGA SEQ ID NO: 33 | PRFNNSSL SEQ ID NO: 123 | TPGLNNAR SEQ ID NO: 162 |
| HVGSQMHA SEQ ID NO: 34 | PRPTVVGT SEQ ID NO: 60 | TSLGTPEA SEQ ID NO: 163 |
| IG*TVPMQ SEQ ID NO: 35 | PVDGGRHL SEQ ID NO: 124 | TTNLAKNS (6) SEQ ID NO: 164 |
| KFTRDGPY SEQ ID NO: 36 | PWFNKSSL SEQ ID NO: 125 | VVQGEQKR (4) SEQ ID NO: 146 |
| KGPAEQGH SEQ ID NO: 37 | QDMNSQRS SEQ ID NO: 126 | WSPDAVEG SEQ ID NO: 165 |
| LAHSPRLW SEQ ID NO: 38 | QGASNSQL SEQ ID NO: 127 | WSQDAVKG (2) SEQ ID NO: 148 |
| LERNRDSD SEQ ID NO: 39 | QQNGTRPS SEQ ID NO: 128 | WTGGGSGT (3) SEQ ID NO: 149 |
| LETHTSLT SEQ ID NO: 40 | QRSAYPTS SEQ ID NO: 129 | WTGGRHL SEQ ID NO: 166 |
| LHDGKYST SEQ ID NO: 41 | QRTPSITP SEQ ID NO: 130 | |
| LKATGRGK SEQ ID NO: 42 | QWMKEQAG SEQ ID NO: 131 | |
| LLPGSADG SEQ ID NO: 43 | RDGRHPSE SEQ ID NO: 132 | |
| LLVTARSH SEQ ID NO: 44 | RGTVTVEQ SEQ ID NO: 133 | |
| LPEVEPTN SEQ ID NO: 45 | RPANHSTA SEQ ID NO: 134 | |
| LPWENSSQ SEQ ID NO: 46 | RQGDADTL SEQ ID NO: 135 | |
| LQRNSDAN SEQ ID NO: 47 | SATISLQV SEQ ID NO: 136 | |
| LQSAPRAT SEQ ID NO: 48 | SHTNLRDT SEQ ID NO: 137 | |
| MLGSQVPT SEQ ID NO: 49 | SRMGETPQ SEQ ID NO: 138 | |
| MSGQGYQA SEQ ID NO: 50 | SSGYLTAN SEQ ID NO: 139 | |
| NPGRDFRD SEQ ID NO: 51 | SSVVSQGP SEQ ID NO: 79 | |
| NQPSDYVS SEQ ID NO: 52 | TGNSPEQA SEQ ID NO: 140 | |
| NSVGSADK SEQ ID NO: 53 | THSQGRLA SEQ ID NO: 141 | |
| NVQRTQRG SEQ ID NO: 54 | TPIVGSNV SEQ ID NO: 142 | |
| PAQLNGPR SEQ ID NO: 55 | TPPKSPSM SEQ ID NO: 143 | |
| PERERLPR SEQ ID NO: 56 | TRMDERSP SEQ ID NO: 144 | |
| PGNGSHTM SEQ ID NO: 57 | TTATTSIT SEQ ID NO: 145 | |
| PIPGTPQP SEQ ID NO: 58 | VVQGEQKR SEQ ID NO: 146 | |
| PMSVPASN SEQ ID NO: 59 | WNDRSGER SEQ ID NO: 147 | |
| PRPTVVGT SEQ ID NO: 60 | WSQDAVKG SEQ ID NO: 148 | |
| PRTNRGPE SEQ ID NO: 61 | WTGGGSGT SEQ ID NO: 149 | |
| PVANPTTA SEQ ID NO: 62 | | |
| PVLGGPPK SEQ ID NO: 63 | | |
| QGSRQGSS SEQ ID NO: 64 | | |
| QMAETPIS SEQ ID NO: 65 | | |
| QMLGIGRS SEQ ID NO: 66 | | |
| QSGDSALN SEQ ID NO: 67 | | |
| RAGLTSSE SEQ ID NO: 68 | | |
| RLDNTGVG SEQ ID NO: 69 | | |
| RMPGKPYS SEQ ID NO: 70 | | |
| RVAGASQP SEQ ID NO: 71 | | |
| RVESSQLE SEQ ID NO: 72 | | |
| SARTGASE SEQ ID NO: 73 | | |
| SERNRASM SEQ ID NO: 74 | | |
| SIDVRMAA SEQ ID NO: 75 | | |

TABLE 1-continued

Peptide sequences identified by the hSyn1-TRADE system using an AAV9-N272N-GGGS(N8)GGGGS library targeting mouse brain neurons.

| 1st round | 2nd round | 3rd round |
|---|---|---|

SRDGHILR
SEQ ID NO: 76

SRQVVLPG
SEQ ID NO: 77

SSRGYTST
SEQ ID NO: 78

SSVVSQGP
SEQ ID NO: 79

SVAESGRE
SEQ ID NO: 80

TALTANTQ
SEQ ID NO: 81

TESSVGNL
SEQ ID NO: 82

TGREGANL
SEQ ID NO: 83

TLSEPPKK
SEQ ID NO: 84

TNAVSGKS
SEQ ID NO: 85

TRAPTIHL
SEQ ID NO: 86

TRESTDRG
SEQ ID NO: 87

TVAAAPNL
SEQ ID NO: 88

TYHNNTPR
SEQ ID NO: 89

VSNSTRTS
SEQ ID NO: 90

VTLQIDTK
SEQ ID NO: 91

WMSRPGPT
SEQ ID NO: 92

WPYRGLTQ
SEQ ID NO: 93

WRRQGSRA
SEQ ID NO: 94

YAQRFAKM
SEQ ID NO: 95

YNSPRQTV
SEQ ID NO: 96

The table lists peptide insertions on AAV9-N272A after each of three rounds of selection. The numbers in parentheses indicate the frequency of each peptide among a total of 69 peptides identified after the three round of selection. Peptides with no number were found only once. The sequences of the peptide region were determined by Sanger sequencing. Actual peptide sequences were randomized octapeptides flanked by glycine-serine linkers such that position Q588 was substituted with GGGS(N8)GGGGS. For example, "-TNHQSAGGGSTTNLAKNSGGGGSAQAQTG-" for TTNLAKNS and "-TNHQSAGGGSQQNGTRPSGGGGSAQAQTG-" for QQNGTRPS.

TABLE 2

Peptide sequences identified by the hSyn1-TRADE system using an AAV9-N272A-GGGS(N8)GGGGS library targeting *rhesus macaque* brain neurons.

1st round

| | |
|---|---|
| AVAGDRLL | SEQ ID NO: 167 |
| DLLTRSVS | SEQ ID NO: 168 |
| EWKTQLAL | SEQ ID NO: 169 |
| GNINVVPH | SEQ ID NO: 170 |
| GSPAASSW | SEQ ID NO: 171 |
| KHSLTLES | SEQ ID NO: 172 |
| KPVSTDTF | SEQ ID NO: 173 |
| LDRSGSTG | SEQ ID NO: 174 |
| LGAQNHVV | SEQ ID NO: 175 |
| LMATDYGP | SEQ ID NO: 176 |
| LRATDYGP | SEQ ID NO: 177 |
| MERTEPLG | SEQ ID NO: 178 |
| NDGLRLHL | SEQ ID NO: 179 |
| NLSAHSHA | SEQ ID NO: 180 |
| NLSAHSHD | SEQ ID NO: 181 |
| RALDLVTR | SEQ ID NO: 182 |
| SAGMARNS | SEQ ID NO: 183 |
| SGQRVGSA | SEQ ID NO: 184 |
| SGQRVGSD | SEQ ID NO: 185 |
| TAQGAAFR | SEQ ID NO: 161 |
| TGRPEQPK | SEQ ID NO: 186 |
| THSPIKLP | SEQ ID NO: 187 |
| TQFSQAQR | SEQ ID NO: 188 |
| VGDSANLR | SEQ ID NO: 189 |

The sequences of the peptide region were determined either by Illumina sequencing or Sanger sequencing. Actual peptide sequences were randomized octapeptides flanked by glycine-serine linkers such that position Q588 was substituted with GGGS(N8)GGGGS. These peptides were recovered from frontal cortex, occipital cortex, hypothalamus and thalamus.

TABLE 3

A list of the 29 AAV capsids contained in the DNA/RNA-barcoded dsAAV-hSyn1-GFP-BCLib library used for phenotype determination of each AAV strain.

| AAV strain (AAV capsid) | Abbreviation | Number of viral clones in the AAV library | Note |
|---|---|---|---|
| AAV9 | AAV9 | 15 | Reference |
| AAV9-N272A | AAV9-N272A | 5 | Reference |

TABLE 3-continued

A list of the 29 AAV capsids contained in the DNA/RNA-barcoded dsAAV-hSyn1-GFP-BCLib library used for phenotype determination of each AAV strain.

| AAV strain (AAV capsid) | Abbreviation | Number of viral clones in the AAV library | Note |
|---|---|---|---|
| AAV-PHP.B | AAV-PHP.B | 2 | Reference |
| AAV9-N272A-TTNLAKNS (peptide insertion site SEQ ID NO: 164) | HN1 | 2 | TRADE variant (C57BL/6J) |
| AAV9-N272A-QQNGTRPS (peptide insertion site SEQ ID NO: 128) | HN2 | 2 | TRADE variant (C57BL/6J) |
| AAV9-N272A-SGQRVGSD (peptide insertion site SEQ ID NO: 185) | HN3 | 2 | TRADE variant (rhesus macaque) |
| AAV9-N272A-AVAGDRLL (peptide insertion site SEQ ID NO: 167) | HN4 | 2 | TRADE variant (rhesus macaque) |
| AAV9-N272A-DLLTRSVS (peptide insertion site SEQ ID NO: 168) | HN5 | 2 | TRADE variant (rhesus macaque) |
| AAV9-N272A-EWKTQLAL (peptide insertion site SEQ ID NO: 169) | HN6 | 2 | TRADE variant (rhesus macaque) |
| AAV9-N272A-GNINVVPH (peptide insertion site SEQ ID NO: 170) | HN7 | 2 | TRADE variant (rhesus macaque) |
| AAV9-N272A-GSPAASSW (peptide insertion site SEQ ID NO: 171) | HN8 | 2 | TRADE variant (rhesus macaque) |
| AAV9-N272A-KHSLTLES (peptide insertion site SEQ ID NO: 172) | HN9 | 2 | TRADE variant (rhesus macaque) |
| AAV9-N272A-KPVSTDTF (peptide insertion site SEQ ID NO: 173) | HN10 | 2 | TRADE variant (rhesus macaque) |
| AAV9-N272A-LDRSGSTG (peptide insertion site SEQ ID NO: 174) | HN11 | 2 | TRADE variant (rhesus macaque) |
| AAV9-N272A-LGAQNHVV (peptide insertion site SEQ ID NO: 175) | HN12 | 2 | TRADE variant (rhesus macaque) |
| AAV9-N272A-LRATDYGP (peptide insertion site SEQ ID NO: 177) | HN13 | 2 | TRADE variant (rhesus macaque) |
| AAV9-N272A-MERTEPLG (peptide insertion site SEQ ID NO: 178) | HN14 | 2 | TRADE variant (rhesus macaque) |
| AAV9-N272A-NDGLRLHL (peptide insertion site SEQ ID NO: 179) | HN15 | 2 | TRADE variant (rhesus macaque) |
| AAV9-N272A-NLSAHSHD (peptide insertion site SEQ ID NO: 181) | HN16 | 2 | TRADE variant (rhesus macaque) |
| AAV9-N272A-RALDLVTR | HN17 | 2 | TRADE variant |

TABLE 3-continued

A list of the 29 AAV capsids contained in the DNA/RNA-barcoded dsAAV-hSyn1-GFP-BCLib library used for phenotype determination of each AAV strain.

| AAV strain (AAV capsid) | Abbreviation | Number of viral clones in the AAV library | Note |
|---|---|---|---|
| (peptide insertion site SEQ ID NO: 182) | | | (rhesus macaque) |
| AAV9-N272A-SAGMARNS (peptide insertion site SEQ ID NO: 183) | HN18 | 2 | TRADE variant (rhesus macaque) |
| AAV9-N272A-TAQGAAFR (peptide insertion site SEQ ID NO: 161) | HN19 | 2 | TRADE variant (rhesus macaque) |
| AAV9-N272A-TGRPEQPK (peptide insertion site SEQ ID NO: 186) | HN20 | 2 | TRADE variant (rhesus macaque) |
| AAV9-N272A-THSPIKLP (peptide insertion site SEQ ID NO: 187) | HN21 | 2 | TRADE variant (rhesus macaque) |
| AAV9-N272A-TQFSQAQR (peptide insertion site SEQ ID NO: 188) | HN22 | 2 | TRADE variant (rhesus macaque) |
| AAV9-N272A-VGDSANLR (peptide insertion site SEQ ID NO: 189) | HN23 | 2 | TRADE variant (rhesus macaque) |
| AAV9-N272A-HQVTSSGA (peptide insertion site SEQ ID NO: 33) | HN24 | 2 | TRADE variant (mouse) |
| AAV9-N272A-LLVTARSH (peptide insertion site SEQ ID NO: 44) | HN25 | 2 | TRADE variant (mouse) |
| AAV9-N272A-VVQGEQKR (peptide insertion site SEQ ID NO: 146) | HN26 | 2 | TRADE variant (mouse) |

The novel AAV9-hSyn1-TRADE-derived capsid variants were selected from those identified following three rounds of selection in mice (Table 1) and one round of selection in a *rhesus macaque* (Table 2). Each recovered AAV variant was assigned an abbreviation, HNX. A DNA/RNA-barcoded dsAAV-hSyn1-GFP-BCLib library containing was constructed such that each AAV variant packaged a unique dsAAV-hSyn1-GFP-BC viral genome expressing AAV variant-specific RNA barcodes. The number of unique AAV barcode clones for each variant, including critical reference variants, is presented in this table.

TABLE 4

Brain neuronal transduction efficiency and biodistribution of the TRADE-identified AAV variants in C57BL/6J mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 |
| AAV9-N272A | 1.93 | 0.22 | 0.82 | 2.11 | 0.06 | 0.51 | 0.17 | 0.25 | 4.49 | 1.42 |
| AAV-PHP.B | 9.42 | 0.64 | 0.92 | 2.35 | 0.27 | 0.81 | 0.36 | 0.62 | 2.69 | 1.45 |
| HN1 | 8.01 | 2.74 | 0.21 | 0.62 | 0.24 | 3.40 | 0.36 | 0.42 | 0.41 | 0.64 |
| HN2 | 6.52 | 1.19 | 0.36 | 0.56 | 0.24 | 2.55 | 0.32 | 0.33 | 0.66 | 0.91 |
| HN3 | 2.35 | 0.41 | 0.95 | 1.29 | 0.09 | 0.45 | 0.20 | 0.25 | 2.57 | 1.45 |
| HN4 | 0.87 | 0.15 | 0.65 | 2.96 | 0.02 | 0.48 | 0.11 | 0.21 | 4.02 | 1.22 |
| HN5 | 0.46 | 0.10 | 0.57 | 2.66 | 0.01 | 0.47 | 0.09 | 0.21 | 3.90 | 1.10 |
| HN6 | 0.37 | 0.22 | 0.64 | 3.13 | 0.01 | 0.52 | 0.08 | 0.27 | 4.27 | 1.22 |
| HN7 | 1.03 | 0.21 | 0.40 | 0.54 | 0.25 | 0.17 | 0.23 | 0.10 | 0.75 | 0.43 |
| HN8 | 0.74 | 0.11 | 0.61 | 2.61 | 0.02 | 0.45 | 0.09 | 0.16 | 3.27 | 1.06 |

TABLE 4-continued

Brain neuronal transduction efficiency and biodistribution of the TRADE-identified AAV variants in C57BL/6J mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| HN9 | 1.47 | 0.28 | 0.62 | 1.49 | 0.08 | 0.30 | 0.15 | 0.16 | 2.41 | 0.82 |
| HN10 | 1.40 | 0.18 | 0.64 | 1.48 | 0.04 | 0.24 | 0.12 | 0.16 | 2.64 | 0.97 |
| HN11 | 1.38 | 0.21 | 0.73 | 1.37 | 0.05 | 0.29 | 0.15 | 0.17 | 3.17 | 1.12 |
| HN12 | 0.80 | 0.17 | 0.26 | 0.42 | 0.24 | 0.16 | 0.20 | 0.06 | 0.49 | 0.21 |
| HN13 | 1.59 | 0.28 | 0.77 | 1.17 | 0.10 | 0.28 | 0.19 | 0.18 | 2.28 | 0.93 |
| HN14 | 0.45 | 0.05 | 0.47 | 1.31 | 0.01 | 0.20 | 0.07 | 0.14 | 1.86 | 0.65 |
| HN15 | 0.50 | 0.21 | 0.68 | 3.48 | 0.01 | 0.58 | 0.10 | 0.24 | 4.70 | 1.30 |
| HN16 | 1.43 | 0.24 | 0.58 | 1.28 | 0.02 | 0.32 | 0.11 | 0.22 | 3.70 | 1.07 |
| HN17 | 0.29 | 0.07 | 0.50 | 2.80 | 0.01 | 0.46 | 0.08 | 0.19 | 3.73 | 1.05 |
| HN18 | 1.46 | 0.12 | 0.68 | 1.78 | 0.11 | 0.28 | 0.17 | 0.14 | 2.10 | 0.92 |
| HN19 | 0.56 | 0.10 | 0.57 | 3.07 | 0.01 | 0.52 | 0.09 | 0.18 | 3.98 | 1.16 |
| HN20 | 1.68 | 0.35 | 0.90 | 1.10 | 0.18 | 0.29 | 0.24 | 0.18 | 1.89 | 0.89 |
| HN21 | 0.26 | 0.08 | 0.50 | 2.53 | 0.01 | 0.46 | 0.06 | 0.14 | 3.44 | 1.01 |
| HN22 | 0.82 | 0.06 | 0.51 | 2.55 | 0.02 | 0.42 | 0.10 | 0.19 | 3.32 | 1.05 |
| HN23 | 2.45 | 0.26 | 0.72 | 1.02 | 0.05 | 0.30 | 0.15 | 0.21 | 2.25 | 1.12 |
| HN24 | 1.33 | 0.22 | 0.63 | 1.31 | 0.05 | 0.28 | 0.14 | 0.15 | 2.83 | 0.90 |
| HN25 | 0.37 | 0.12 | 0.64 | 3.25 | 0.02 | 0.53 | 0.09 | 0.22 | 4.35 | 1.23 |
| HN26 | 0.73 | 0.14 | 0.63 | 2.53 | 0.06 | 0.40 | 0.12 | 0.17 | 2.86 | 1.07 |

A DNA/RNA-barcoded dsAAV-hSynI-GFP-BC library (dsAAV-hSynI-GFP-BCLib) containing 26 novel AAV variants identified by TRADE and control AAV capsids was injected intravenously into 3 C57BL/6J mice at a dose of $5 \times 10^{11}$ vg per mouse (for the library, see Table 3). Two weeks post-injection, various tissues were harvested and analyzed for brain transduction by AAV RNA Barcode-Seq and biodistribution to peripheral organs by AAV DNA Barcode-Seq. All the values are normalized with those of AAV9 (AAV9 = 1.0).

TABLE 5

Pharmacokinetic profiles of TRADE-identified AAV variants in C57BL/6J mice following intravenous administration.

| | 1 m | 10 m | 30 m | 1 h | 4 h | 8 h | 24 h | 72 h |
|---|---|---|---|---|---|---|---|---|
| AAV9 | 1.00 | 1.00 | 1.00 | 1.00 | 1.00 | 1.00 | 1.00 | 1.00 |
| AAV9-N272A | 1.16 | 1.17 | 1.28 | 1.34 | 1.77 | 2.02 | 3.14 | 0.13 |
| AAV-PHP.B | 1.38 | 1.42 | 1.44 | 1.62 | 1.88 | 2.15 | 3.14 | 0.39 |
| HN1 | 0.87 | 0.47 | 0.29 | 0.29 | 0.27 | 0.31 | 0.37 | 0.02 |
| HN2 | 0.79 | 0.60 | 0.49 | 0.55 | 0.59 | 0.66 | 0.91 | 0.03 |
| HN3 | 1.12 | 1.15 | 1.21 | 1.32 | 1.65 | 1.88 | 3.05 | 0.04 |
| HN4 | 1.32 | 1.50 | 1.43 | 1.52 | 2.01 | 2.37 | 3.78 | 0.03 |
| HN5 | 1.14 | 1.30 | 1.37 | 1.42 | 1.84 | 2.03 | 3.37 | 0.02 |
| HN6 | 1.21 | 1.34 | 1.43 | 1.60 | 1.99 | 2.38 | 3.90 | 0.02 |
| HN7 | 0.92 | 0.88 | 0.93 | 0.93 | 1.09 | 1.21 | 1.22 | 0.03 |
| HN8 | 1.20 | 1.29 | 1.30 | 1.44 | 1.83 | 2.10 | 3.42 | 0.03 |
| HN9 | 0.94 | 0.91 | 0.97 | 0.99 | 1.26 | 1.36 | 1.97 | 0.04 |
| HN10 | 0.98 | 0.98 | 1.00 | 1.06 | 1.31 | 1.36 | 1.89 | 0.02 |
| HN11 | 1.00 | 1.04 | 1.04 | 1.14 | 1.39 | 1.48 | 2.11 | 0.02 |
| HN12 | 0.93 | 0.93 | 0.84 | 0.79 | 0.71 | 0.61 | 0.62 | 0.01 |
| HN13 | 0.95 | 0.90 | 0.95 | 0.95 | 1.20 | 1.28 | 1.60 | 0.03 |
| HN14 | 0.94 | 0.95 | 1.00 | 1.08 | 1.41 | 1.58 | 2.56 | 0.01 |
| HN15 | 1.39 | 1.56 | 1.67 | 1.66 | 2.20 | 2.76 | 4.26 | 0.03 |
| HN16 | 0.98 | 1.00 | 1.04 | 1.15 | 1.46 | 1.63 | 2.77 | 0.02 |
| HN17 | 1.32 | 1.28 | 1.27 | 1.31 | 1.94 | 2.13 | 4.03 | 0.04 |
| HN18 | 1.10 | 1.06 | 0.96 | 0.93 | 0.82 | 0.84 | 1.27 | 0.01 |
| HN19 | 1.39 | 1.39 | 1.51 | 1.49 | 2.04 | 2.50 | 4.09 | 0.03 |
| HN20 | 1.15 | 1.09 | 1.19 | 1.14 | 1.41 | 1.70 | 1.97 | 0.06 |
| HN21 | 1.25 | 1.19 | 1.34 | 1.38 | 1.90 | 1.99 | 3.30 | 0.02 |
| HN22 | 1.16 | 1.24 | 1.32 | 1.35 | 1.74 | 2.13 | 3.74 | 0.02 |
| HN23 | 1.03 | 1.02 | 1.04 | 1.14 | 1.43 | 1.64 | 2.56 | 0.03 |
| HN24 | 0.99 | 1.01 | 1.05 | 1.16 | 1.45 | 1.58 | 2.38 | 0.03 |
| HN25 | 1.29 | 1.40 | 1.44 | 1.49 | 1.93 | 2.49 | 3.74 | 0.03 |
| HN26 | 1.21 | 1.19 | 1.29 | 1.30 | 1.74 | 2.03 | 3.09 | 0.03 |

AAV DNA Barcode-Seq analysis was performed on the blood samples obtained from the mice injected with $1 \times 10^{13}$ vg/kg of the DNA/RNA-barcoded dsAAV-hSynI-GFP-BCLib library (see Table 3, n = 2) All the values are normalized with those of AAV9 (AAV9 = 1.0). All the values are normalized to AAV9 (AAV9 = 1.0).

TABLE 6

Brain neuronal transduction efficiency and biodistribution of the TRADE-identified AAV variants in BALB/cJ mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 |
| AAV9-N272A | 1.00 | 0.30 | 0.45 | 1.23 | 0.03 | 0.64 | 0.29 | 1.23 | 2.75 | 0.17 |
| AAV-PHP.B | 1.06 | 0.44 | 0.56 | 1.30 | 0.22 | 0.67 | 0.40 | 1.12 | 1.69 | 0.30 |
| HN1 | 7.59 | 17.84 | 0.18 | 0.52 | 0.05 | 3.75 | 0.21 | 0.28 | 0.31 | 0.36 |
| HN2 | 3.26 | 4.71 | 0.31 | 0.52 | 0.07 | 3.13 | 0.25 | 0.39 | 0.69 | 0.44 |
| HN3 | 1.00 | 0.35 | 0.51 | 1.04 | 0.04 | 0.41 | 0.20 | 0.60 | 1.38 | 0.14 |
| HN4 | 0.41 | 0.41 | 0.29 | 1.58 | 0.01 | 0.44 | 0.16 | 1.18 | 2.50 | 0.09 |
| HN5 | 0.28 | 0.15 | 0.25 | 1.34 | 0.00 | 0.38 | 0.13 | 1.05 | 2.25 | 0.07 |
| HN6 | 0.25 | 0.06 | 0.30 | 1.60 | 0.01 | 0.45 | 0.17 | 1.17 | 2.69 | 0.07 |
| HN7 | 0.54 | 0.21 | 0.27 | 0.65 | 0.12 | 0.22 | 0.16 | 0.32 | 0.75 | 0.11 |
| HN8 | 0.34 | 0.03 | 0.28 | 1.53 | 0.01 | 0.38 | 0.14 | 0.94 | 2.10 | 0.07 |

TABLE 6-continued

Brain neuronal transduction efficiency and biodistribution of the TRADE-identified AAV variants in BALB/cJ mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| HN9 | 0.49 | 0.19 | 0.28 | 1.18 | 0.02 | 0.22 | 0.11 | 0.45 | 1.08 | 0.07 |
| HN10 | 0.54 | 0.19 | 0.33 | 1.25 | 0.01 | 0.30 | 0.14 | 0.50 | 1.82 | 0.08 |
| HN11 | 0.23 | 0.12 | 0.23 | 1.15 | 0.03 | 0.17 | 0.09 | 0.62 | 0.95 | 0.05 |
| HN12 | 0.34 | 0.13 | 0.19 | 0.98 | 0.03 | 0.12 | 0.07 | 0.23 | 0.48 | 0.04 |
| HN13 | 0.43 | 0.25 | 0.36 | 1.25 | 0.03 | 0.25 | 0.15 | 0.41 | 1.01 | 0.09 |
| HN14 | 0.22 | 0.08 | 0.20 | 0.93 | 0.02 | 0.14 | 0.08 | 0.38 | 0.68 | 0.04 |
| HN15 | 0.25 | 0.26 | 0.33 | 1.80 | 0.01 | 0.46 | 0.19 | 1.39 | 3.03 | 0.10 |
| HN16 | 0.62 | 0.25 | 0.32 | 0.93 | 0.01 | 0.41 | 0.16 | 0.71 | 1.55 | 0.10 |
| HN17 | 0.18 | 0.12 | 0.22 | 1.40 | 0.00 | 0.37 | 0.13 | 0.96 | 2.29 | 0.07 |
| HN18 | 0.75 | 0.16 | 0.40 | 1.46 | 0.04 | 0.29 | 0.15 | 0.59 | 1.36 | 0.08 |
| HN19 | 0.28 | 0.10 | 0.28 | 1.57 | 0.01 | 0.44 | 0.15 | 1.14 | 2.51 | 0.08 |
| HN20 | 0.69 | 0.11 | 0.42 | 0.56 | 0.08 | 0.31 | 0.13 | 0.53 | 0.85 | 0.12 |
| HN21 | 0.14 | 0.15 | 0.25 | 1.38 | 0.00 | 0.34 | 0.11 | 0.91 | 2.34 | 0.08 |
| HN22 | 0.41 | 0.09 | 0.22 | 1.33 | 0.01 | 0.36 | 0.12 | 1.01 | 2.09 | 0.07 |
| HN23 | 0.79 | 0.32 | 0.33 | 0.99 | 0.02 | 0.36 | 0.17 | 0.43 | 1.24 | 0.10 |
| HN24 | 0.56 | 0.25 | 0.34 | 1.17 | 0.02 | 0.34 | 0.14 | 0.53 | 1.33 | 0.08 |
| HN25 | 0.19 | 0.02 | 0.30 | 1.65 | 0.01 | 0.49 | 0.17 | 1.15 | 2.68 | 0.09 |
| HN26 | 0.31 | 0.11 | 0.33 | 1.52 | 0.02 | 0.35 | 0.17 | 0.84 | 1.77 | 0.09 |

A DNA/RNA-barcoded dsAAV-hSynl-GFP-BC library (dsAAV-hSynl-GFP-BCLib) containing 26 novel AAV variants identified by TRADE and control AAV capsids was injected intravenously into 3 BALB/cJ mice at a dose of $5 \times 10^{11}$ vg per mouse (for the library, see Table 3). Two weeks post-injection, various tissues were harvested and analyzed for brain transduction by AAV RNA Barcode-Seq and biodistribution to peripheral organs by AAV DNA Barcode-Seq. All the values are normalized with those of AAV9 (AAV9 = 1.0).

TABLE 7

Transduction efficiency of hSynl-TRADE-derived AAV variants in various brain regions of one *rhesus macaque* following intravenous administration as determined by AAV hSynl-RNA Barcode-Seq analysis

| | Cerebellum (Granular layer) | Cerebellum (Purkinje) | Cingulate Gyrus | Frontal Cortex | Hippo-campus | Hypo-thalamus | Medulla | Occipital Cortex | Pons | Preoptic Area | Putamen | Thalamus |
|---|---|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 | 1.00 | 1.00 |
| AAV9-N272A | 1.28 | 1.63 | 1.76 | 1.75 | 2.08 | 1.00 | 1.45 | 1.51 | 1.45 | 0.66 | 1.99 | 1.19 |
| AAV-PHP.B | 0.78 | 1.21 | 1.27 | 1.50 | 1.39 | 0.94 | 1.33 | 1.23 | 1.62 | 0.35 | 1.29 | 0.69 |
| HN1 | 1.99 | 1.78 | 2.68 | 2.18 | 4.07 | 2.05 | 1.39 | 1.54 | 1.99 | 1.99 | 2.54 | 2.84 |
| HN2 | 0.81 | 0.96 | 1.06 | 1.13 | 1.45 | 0.78 | 0.77 | 0.84 | 0.79 | 0.72 | 1.15 | 1.16 |
| HN3 | 1.75 | 2.03 | 2.14 | 2.28 | 3.54 | 1.48 | 1.87 | 1.67 | 1.71 | 1.28 | 2.20 | 1.87 |
| HN4 | 0.27 | 0.61 | 0.70 | 0.68 | 0.37 | 0.39 | 0.58 | 0.54 | 0.27 | 0.30 | 0.49 | 0.62 |
| HN5 | 0.15 | 0.27 | 0.35 | 0.22 | 0.15 | 0.01 | 0.27 | 0.17 | 0.27 | 0.22 | 0.31 | 0.15 |
| HN6 | 0.06 | 0.28 | 0.36 | 0.12 | 0.10 | 0.27 | 0.04 | 0.12 | 0.12 | 0.01 | 0.26 | 0.10 |
| HN7 | 0.96 | 1.40 | 1.44 | 1.45 | 1.64 | 1.13 | 1.48 | 1.18 | 1.01 | 0.87 | 1.39 | 1.29 |
| HN8 | 0.38 | 0.61 | 0.59 | 0.67 | 0.73 | 0.42 | 0.56 | 0.42 | 0.45 | 0.35 | 0.57 | 0.50 |
| HN9 | 1.17 | 1.45 | 1.91 | 1.66 | 2.15 | 0.92 | 1.65 | 1.30 | 1.27 | 1.10 | 1.96 | 1.48 |
| HN10 | 1.08 | 1.24 | 1.40 | 1.45 | 1.78 | 0.87 | 1.33 | 1.16 | 1.11 | 0.76 | 1.50 | 1.00 |
| HN11 | 0.96 | 1.22 | 1.37 | 1.42 | 1.62 | 1.00 | 1.28 | 1.15 | 1.12 | 0.65 | 1.41 | 1.19 |
| HN12 | 1.04 | 1.43 | 1.64 | 1.70 | 1.98 | 0 | 1.49 | 1.26 | 1.09 | 0.73 | 1.74 | 1.44 |
| HN13 | 1.77 | 1.74 | 1.86 | 1.82 | 2.17 | 1.20 | 2.38 | 1.54 | 1.97 | 1.36 | 2.14 | 1.77 |
| HN14 | 0.13 | 0.45 | 0.27 | 0.26 | 0.28 | 0.14 | 0.30 | 0.32 | 0.19 | 0.04 | 0.23 | 0.17 |
| HN15 | 0.38 | 0.43 | 0.19 | 0.46 | 0.44 | 0.04 | 0.28 | 0.19 | 0.23 | 0.63 | 0.36 | 0.09 |
| HN16 | 0.57 | 0.65 | 0.79 | 0.82 | 0.89 | 0.35 | 0.75 | 0.77 | 0.64 | 0.18 | 0.72 | 0.54 |
| HN17 | 0.05 | 0.18 | 0.24 | 0.14 | 0.08 | 0.28 | 0.16 | 0.11 | 0.07 | 0.01 | 0.19 | 0.03 |
| HN18 | 1.21 | 1.23 | 1.62 | 1.70 | 2.60 | 1.17 | 1.47 | 1.15 | 1.09 | 0.69 | 1.46 | 1.13 |
| HN19 | 0.24 | 0.24 | 0.21 | 0.59 | 0.50 | 0.13 | 0.14 | 0.26 | 0.26 | 0.01 | 0.31 | 0.17 |
| HN20 | 1.08 | 1.42 | 1.60 | 1.81 | 2.28 | 1.45 | 1.51 | 1.22 | 1.41 | 1.32 | 2.27 | 1.34 |
| HN21 | 0.19 | 0.11 | 0.05 | 0.15 | 0.04 | 0.49 | 0.27 | 0.19 | 0.08 | 0.01 | 0.10 | 0.14 |
| HN22 | 0.27 | 0.17 | 0.48 | 0.59 | 0.49 | 0.24 | 0.24 | 0.27 | 0.19 | 0.01 | 0.23 | 0.12 |
| HN23 | 0.60 | 1.01 | 1.21 | 1.11 | 1.55 | 0.61 | 1.23 | 0.92 | 0.95 | 0.49 | 1.25 | 0.76 |
| HN24 | 0.99 | 1.18 | 1.19 | 1.33 | 1.71 | 0.70 | 1.17 | 1.06 | 1.04 | 0.57 | 1.39 | 1.21 |
| HN25 | 0.13 | 0.14 | 0.06 | 0.32 | 0.21 | 0.12 | 0.23 | 0.24 | 0.07 | 0.01 | 0.28 | 0.08 |
| HN26 | 0.35 | 0.52 | 0.42 | 0.60 | 0.88 | 0.40 | 0.50 | 0.44 | 0.36 | 0.27 | 0.61 | 0.28 |

AAV RNA Barcode-Seq analysis was performed on RNAs extracted from various brain regions of one *rhesus macaque* (n = 1) intravenously injected with $2.0 \times 10^{13}$ vg/kg of a DNA/RNA-barcoded dsAAV-hSynl-GFP-BCLib library that expresses RNA barcodes under the control of the hSynl enhancer-promoter. All the values are normalized with those of AAV9 (AAV9 = 1.0).

TABLE 8

Pharmacokinetic profiles of hSynI-TRADE-derived AAV variants in *rhesus macaque* following intravenous administration.

| | 1 m | 10 m | 30 m | 1 h | 4 h | 8 h | 24 h | 72 h |
|---|---|---|---|---|---|---|---|---|
| AAV9 | 1.00 | 1.00 | 1.00 | 1.00 | 1.00 | 1.00 | 1.00 | 1.00 |
| AAV9-N272A | 0.95 | 0.96 | 1.06 | 1.05 | 1.24 | 1.79 | 2.64 | 1.18 |
| AAV-PHP.B | 1.00 | 1.10 | 1.16 | 1.11 | 1.27 | 1.99 | 2.94 | 1.69 |
| HN1 | 0.78 | 0.66 | 0.71 | 0.65 | 0.67 | 0.88 | 0.65 | 0.30 |
| HN2 | 0.69 | 0.72 | 0.69 | 0.62 | 0.75 | 0.92 | 1.24 | 0.25 |
| HN3 | 0.85 | 0.86 | 0.96 | 0.77 | 1.12 | 1.70 | 2.60 | 0.60 |
| HN4 | 1.07 | 1.07 | 1.15 | 1.15 | 1.30 | 1.88 | 3.39 | 2.15 |
| HN5 | 0.99 | 0.98 | 1.14 | 1.06 | 1.19 | 1.62 | 2.83 | 1.39 |
| HN6 | 1.13 | 1.09 | 1.18 | 1.09 | 1.32 | 1.97 | 3.32 | 1.90 |
| HN7 | 0.75 | 0.78 | 0.81 | 0.79 | 0.95 | 1.33 | 1.78 | 0.27 |
| HN8 | 1.05 | 1.06 | 1.02 | 1.07 | 1.27 | 1.82 | 3.02 | 1.67 |
| HN9 | 0.83 | 0.76 | 0.87 | 0.78 | 0.92 | 1.36 | 1.91 | 0.29 |
| HN10 | 0.84 | 0.87 | 0.90 | 0.87 | 1.14 | 1.32 | 2.32 | 0.28 |
| HN11 | 0.88 | 0.89 | 0.90 | 0.86 | 1.20 | 1.55 | 2.42 | 0.61 |
| HN12 | 0.81 | 0.80 | 0.86 | 0.80 | 0.99 | 1.41 | 1.90 | 0.27 |
| HN13 | 0.76 | 0.71 | 0.82 | 0.76 | 0.90 | 1.31 | 1.86 | 0.29 |
| HN14 | 0.76 | 0.75 | 0.83 | 0.78 | 0.99 | 1.40 | 2.21 | 0.18 |
| HN15 | 1.31 | 1.07 | 1.27 | 1.23 | 1.36 | 2.37 | 4.46 | 2.03 |
| HN16 | 0.76 | 0.80 | 0.91 | 0.84 | 0.98 | 1.41 | 1.90 | 0.26 |
| HN17 | 1.02 | 1.07 | 1.21 | 1.00 | 1.29 | 1.88 | 2.91 | 1.84 |
| HN18 | 0.88 | 0.88 | 0.96 | 0.90 | 1.10 | 1.57 | 2.44 | 0.58 |
| HN19 | 1.08 | 1.04 | 1.15 | 1.14 | 1.26 | 2.04 | 3.69 | 2.05 |
| HN20 | 0.89 | 0.82 | 0.88 | 0.81 | 0.91 | 1.62 | 2.28 | 0.39 |
| HN21 | 1.00 | 1.00 | 1.11 | 0.98 | 1.20 | 1.54 | 2.41 | 2.10 |
| HN22 | 0.96 | 0.97 | 1.09 | 1.03 | 1.24 | 1.74 | 2.90 | 1.82 |
| HN23 | 0.76 | 0.76 | 0.86 | 0.80 | 0.97 | 1.50 | 2.14 | 0.35 |
| HN24 | 0.93 | 1.00 | 0.96 | 1.00 | 1.41 | 1.48 | 2.31 | 1.41 |
| HN25 | 1.05 | 1.16 | 1.08 | 1.19 | 1.18 | 2.00 | 3.52 | 1.54 |
| HN26 | 1.03 | 0.98 | 1.08 | 1.07 | 1.18 | 1.77 | 2.72 | 1.56 |

AAV DNA Barcode-Seq analysis was performed on the blood samples obtained from a single *rhesus macaque* injected with $2 \times 10^{13}$ vg/kg of the DNA/RNA-barcoded dsAAV-hSynI-GFP-BCLib library (the same animal as in Table 7). All the values are normalized with those of AAV9 (AAV9 = 1.0).

TABLE 9

Biodistribution of hSynI-TRADE-derived AAV variants to peripheral tissues of a *rhesus macaque* following intravenous administration as determined by AAV DNA Barcode-Seq analysis

| | Liver | Heart | Lung | Kidney | Pancreas | Spleen | Gastrocnemius muscle | Soleus muscle | Intestine | Bone marrow | Smooth muscle (Stomach) |
|---|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 | 1.00 |
| AAV9-N272A | 0.07 | 0.20 | 0.79 | 1.29 | 2.91 | 4.67 | 0.26 | 0.50 | 0.64 | 0.06 | 0.82 |
| AAV-PHP.B | 0.35 | 0.42 | 1.09 | 1.22 | 2.55 | 2.14 | 0.54 | 0.77 | 0.40 | 0.43 | 0.80 O |
| HN1 | 0.26 | 0.41 | 0.34 | 0.41 | 0.35 | 0.76 | 1.04 | 1.12 | 0.24 | 0.33 | 0.33 |
| HN2 | 0.16 | 0.17 | 0.35 | 0.32 | 0.51 | 0.71 | 0.32 | 0.52 | 0.11 | 0.07 | 0.30 |
| HN3 | 0.12 | 0.21 | 0.78 | 0.91 | 2.19 | 2.48 | 0.25 | 0.58 | 0.18 | 0.05 | 0.63 |
| HN4 | 0.02 | 0.08 | 0.78 | 1.12 | 2.25 | 3.42 | 0.17 | 0.41 | 0.15 | 0.03 | 0.39 |
| HN5 | 0.01 | 0.05 | 0.73 | 0.98 | 2.24 | 2.85 | 0.10 | 0.30 | 0.07 | 0.01 | 0.37 |
| HN6 | 0.01 | 0.05 | 0.92 | 1.11 | 2.15 | 3.50 | 0.11 | 0.40 | 0.12 | 0.01 | 0.30 |
| HN7 | 0.27 | 0.19 | 0.36 | 0.43 | 0.47 | 0.51 | 0.18 | 0.23 | 0.16 | 0.12 | 0.37 |
| HN8 | 0.04 | 0.08 | 0.71 | 0.98 | 2.28 | 2.57 | 0.12 | 0.38 | 0.11 | 0.02 | 0 |
| HN9 | 0.12 | 0.13 | 0.32 | 0.36 | 0.71 | 0.79 | 0.13 | 0.31 | 0.11 | 0.04 | 0.29 |
| HN10 | 0.08 | 0.13 | 0.63 | 0.63 | 1.39 | 2.53 | 0.16 | 0.38 | 0.1 | 0.02 | 0.28 |
| HN11 | 0.06 | 0.16 | 0.63 | 0.74 | 1.62 | 1.68 | 0.18 | 0.44 | 0.16 | 0.03 | 0.47 |
| HN12 | 0.19 | 0.11 | 0.28 | 0.38 | 0.56 | 0.61 | 0.10 | 0.19 | 0.09 | 0.05 | 0.30 |
| HN13 | 0.18 | 0.23 | 0.58 | 0.44 | 0.88 | 1.12 | 0.21 | 0.38 | 0.18 | 0.06 | 0.49 |
| HN14 | 0.00 | 0.04 | 0.30 | 0.49 | 0.59 | 0.83 | 0.06 | 0.28 | 0.05 | 0.01 | 0.34 |
| HN15 | 0.01 | 0.06 | 1.01 | 1.43 | 2.43 | 3.80 | 0.13 | 0.46 | 0.10 | 0.02 | 0.69 |
| HN16 | 0.02 | 0.07 | 0.37 | 1.00 | 0.70 | 0.87 | 0.08 | 0.17 | 0.06 | 0.02 | 0.28 |
| HN17 | 0.01 | 0.04 | 0.85 | 1.01 | 2.38 | 3.25 | 0.08 | 0.29 | 0.10 | 0.01 | 0.32 |
| HN18 | 0.15 | 0.13 | 0.36 | 0.52 | 0.90 | 1.17 | 0.13 | 0.31 | 0.09 | 0.01 | 0.33 |
| HN19 | 0.06 | 0.08 | 0.93 | 1.14 | 2.98 | 3.41 | 0.15 | 0.42 | 0.10 | 0.02 | 0.36 |
| HN20 | 0.36 | 0.22 | 0.34 | 0.50 | 0.88 | 0.96 | 0.21 | 0.48 | 0.14 | 0.05 | 0.31 |
| HN21 | 0.02 | 0.05 | 0.74 | 1.03 | 2.17 | 3.08 | 0.12 | 0.33 | 0.06 | 0.01 | 0.57 |
| HN22 | 0.06 | 0.07 | 0.72 | 0.89 | 1.73 | 2.68 | 0.14 | 0.31 | 0.09 | 0.02 | 0.25 |
| HN23 | 0.04 | 0.08 | 0.61 | 0.28 | 0.74 | 0.71 | 0.09 | 0.30 | 0.10 | 0.01 | 0.24 |
| HN24 | 0.06 | 0.14 | 0.66 | 0.74 | 1.99 | 1.98 | 0.18 | 0.43 | 0.13 | 0.03 | 0.50 |
| HN25 | 0.06 | 0.07 | 0.90 | 1.21 | 2.76 | 3.28 | 0.22 | 0.43 | 0.10 | 0.03 | 0.56 |
| HN26 | 0.17 | 0.10 | 0.64 | 0.90 | 1.84 | 2.38 | 0.12 | 0.35 | 0.12 | 0.02 | 0.56 |

AAV DNA Barcode-Seq analysis was performed on DNA extracted from various peripheral tissues of one *rhesus macaque* (n = 1, the same animal as presented in Table 7) intravenously injected with $2 \times 10^{13}$ vg/kg of a DNA/RNA-barcoded dsAAV-hSynI-GFP-BCLib library. All values are normalized to AAV9 (AAV9 = 1.0).

TABLE 9

Splice donor and splice acceptor sites identified in antisense AAV cap ORF transcripts.

| SEQ ID | AAV serotype | SD or SA | Exon-intron junction sequence (Introns are underlined) |
|---|---|---|---|
| SEQ ID NO: 199 | AAV1 | SD | 1009-CTTACCAGCA-1018 |
| SEQ ID NO: 199 | AAV3 | SD | 1006-CTTACCAGCA-1015 |
| SEQ ID NO: 200 | AAV1 | SD | 1228-TTTACCTTCA-1237 |
| SEQ ID NO: 201 | AAV3 | SD | 1237-TATACCTTCG-1246 |
| SEQ ID NO: 202 | AAV1 | SD | 1331-ATTACCTGAA-1340 |
| SEQ ID NO: 203 | AAV1 | SD | 1434-GCTACCTGGA-1443 |
| SEQ ID NO: 204 | AAV1 | SD | 1502-TTTACCTGGA-1510 |
| SEQ ID NO: 205 | AAV1 | SD | 1803-ATTACCTGGC-1812 |
| SEQ ID NO: 206 | AAV3 | SD | 1803-CTTACCTGGC-1812 |
| SEQ ID NO: 207 | AAV1 | SD | 1835-TGTACCTGCA-1844 |
| SEQ ID NO: 208 | AAV1 | SD | 2189-GTTACCTTAC-2198 |
| SEQ ID NO: 209 | AAV9 | SD | 2189-GATACCTGAC-2198 |
| SEQ ID NO: 210 | AAV1 | SD | 2194-CTTACCCGTC-2203 |
| SEQ ID NO: 211 | AAV3 | SD | 2194-CTCACACGAA-2203 |
| SEQ ID NO: 212 | AAV1 | SA | 305-AGCGTCTGCA-314 |
| SEQ ID NO: 213 | AAV1 | SA | 414-GGCTCCTGGA-423 |
| SEQ ID NO: 213 | AAV3 | SA | 414-GGCTCCTGGA-423 |
| SEQ ID NO: 214 | AAV1 | SA | 495-GCCCGCTAAA-504 |
| SEQ ID NO: 214 | AAV9 | SA | 495-GCCCGCTAAA-504 |
| SEQ ID NO: 215 | AAV3 | SA | 1133-TCACCCTGAA-1142 |
| SEQ ID NO: 216 | AAV1 | SA | 1181-ACTGCCTGGA-1190 |
| SEQ ID NO: 202 | AAV1 | SA | 1331-ATTACCTGAA-1340 |
| SEQ ID NO: 217 | AAV3 | SA | 1328-ACTACCTGAA-1337 |
| SEQ ID NO: 218 | AAV1 | SA | 1464-CGTTTCTAAA-1473 |
| SEQ ID NO: 219 | AAV1 | SA | 1653-AAACACTGCA-1662 |
| SEQ ID NO: 220 | AAV1 | SA | 2054-GGGAGCTGCA-2063 |
| SEQ ID NO: 463 | AAV3 | SA | 2054-GGGAGCTACA-2063 |

Ten nucleotides around exon-intron junctions identified in antisense AAV cap mRNA are presented with the junction at the center. Letters with underlines represent intron sequences. Letters with no underline represent exon sequences. Numbers indicate nucleotide positions of the AAV cap ORF. SD, splice donor; SA, splice acceptor. Please note that SEQ ID NO: 199 of AAV1 and SEQ ID NO: 199 of AAV3 are corresponding to each other in sequence alignment. Likewise, SEQ ID NO: 213 of AAV1 and SEQ ID NO: 213 of AAV3 are corresponding to each other in sequence alignment.

In the course of the experiment, when the AAV9 cap gene ORF was expressed in an antisense orientation in HEK293 cells or Neuro2a cells, the majority of the antisense AAV9 cap gene mRNA-derived RT-PCR products were truncated by approximately 1.7 kb (FIG. 4), although this was not the case with the RNA recovered from the AAV-PHP.B-hSynI-GFP-TRADE-transduced mouse brain tissue (FIG. 3C, FIG. 3D). Sequencing of the truncated RT-PCR products revealed that a 1694 bp-long region was missing within the AAV9 cap ORF (FIG. 5). Without being bound by any particular theory, it appears that the truncation results from a splicing event, based on the observation that we could identify splice donor and acceptor sites in the PCR products that have the common features of exon-intron junctions. Intriguingly, a sequence alignment study revealed that the cryptic splice donor and acceptor sites with the common features of exon-intron junctions can also be identified in many naturally occurring AAV serotypes at the regions corresponding to the splice donor and acceptor sites identified in the AAV9 cap gene and they are highly conserved (FIGS. 6A-6F). This indicates that splicing could potentially take place in the cap ORF-derived antisense mRNA of not only AAV9 but also many other AAV strains. To date, we have found that splicing occurs on the AAV3 cap ORF-derived antisense mRNA when it is expressed under the control of a human liver-specific promoter (LSP) in HepG2 cells. Although full characterization has not yet been completed, a preliminary RT-PCR using an antisense mRNA-specific RT primer yielded truncated RT-PCR products in addition to the full-length, non-spliced product. The sequencing analysis of two truncated RT-PCR products revealed that there were multiple splicing events on the antisense mRNA (FIGS. 7A-7B). A sequencing alignment study has identified additional potential splice donor and acceptor sites (FIGS. 8A-8F and FIGS. 9A-9C). We also found splicing events in the antisense mRNA derived from the AAV1 cap ORF when antisense mRNA was transcribed by the hSynI enhancer-promoter in HEK293 cells or Neuro2a cells (FIG. 10). Many of the identified splice donor sites (GT/CA) and splice acceptor sites (AG/TC) are highly conserved across different serotypes, indicating the possibility that these sites are also utilized as splicing donor and acceptor sites in the AAV serotypes that have yet to be investigated. Indeed, we have found that splicing of antisense mRNA transcripts of the AAV1, AAV3 and AAV9 cap ORFs uses several common splice donor and acceptor sites (FIG. 10). To date, we have not yet observed splicing of antisense mRNA transcripts of the AAV5 cap ORF. For serotypes other than AAV1, 3, 5 and 9, splicing events in antisense mRNA of the AAV cap ORFs have not yet been investigated.

Potential splicing of the cap ORF-derived antisense mRNA is scientifically intriguing, but may hinder the TRADE system when the full-length cap ORF sequence needs to be recovered from antisense mRNA. To overcome this potential issue, we introduced silent mutations that presumably disrupt the conserved sequences at exon-intron junctions and branching points. To demonstrate proof of principle of this approach, we introduced silent mutations into the AAV9 cap ORF contained in the plasmid, pAAV9-N272A-PHP.B-hSyn1-GFP-TRADE, that disrupt the splice acceptor (SA) consensus sequence (pAAV9NS1 construct), the splice donor (SD) consensus sequence (pAAV9NS2 construct), and both the splice acceptor and donor consensus sequences (pAAV9NS3 construct). Please note that NS stands for "non-spliced." The method we use to disrupt these consensus sequences is described below.

We codon-optimize the AAV cap ORF sequence for human cell expression.

To identify potential splice donor and acceptor sites on antisense mRNA derived from the cap ORFs, we develop and use our proprietary database of potential splice donor and acceptor sites on antisense mRNA based on our experimental and bioinformatics observations (i.e., FIGS. 5, 6A-6F, 7A-7B, 8A-8F, 9A-9C and 10).

We destroy the GT (splice donor) and/or AG (splice acceptor) consensus sequence by changing at least one nucleotide using the codon-optimized sequence. If the codon-optimized sequence is not applicable, we use an alternative nucleotide(s) that can destroy the consensus sequence.

We remove a stretch of T's upstream of the splice acceptor sites by introducing silence mutations based on the codon-optimized sequence. If the codon-optimized sequence is not sufficient to destroy a stretch of T

```
REGION                    1..8
                          note = peptide
PEPTIDE                   1..8
source                    1..8
                          mol_type = protein
                          organism = synthetic construct
SEQUENCE: 5
ALGTATQR                                                                        8

SEQ ID NO: 6              moltype = AA   length = 8
FEATURE                   Location/Qualifiers
REGION                    1..8
                          note = peptide
PEPTIDE                   1..8
source                    1..8
                          mol_type = protein
                          organism = synthetic construct
SEQUENCE: 6
ALNTALVE                                                                        8

SEQ ID NO: 7              moltype = AA   length = 8
FEATURE                   Location/Qualifiers
REGION                    1..8
                          note = peptide
PEPTIDE                   1..8
source                    1..8
                          mol_type = protein
                          organism = synthetic construct
SEQUENCE: 7
AMVRLTHN                                                                        8

SEQ ID NO: 8              moltype = AA   length = 8
FEATURE                   Location/Qualifiers
REGION                    1..8
                          note = peptide
PEPTIDE                   1..8
source                    1..8
                          mol_type = protein
                          organism = synthetic construct
SEQUENCE: 8
ASRDPSAT                                                                        8

SEQ ID NO: 9              moltype = AA   length = 8
FEATURE                   Location/Qualifiers
REGION                    1..8
                          note = peptide
PEPTIDE                   1..8
source                    1..8
                          mol_type = protein
                          organism = synthetic construct
SEQUENCE: 9
DANDARQR                                                                        8

SEQ ID NO: 10             moltype = AA   length = 8
FEATURE                   Location/Qualifiers
REGION                    1..8
                          note = peptide
PEPTIDE                   1..8
source                    1..8
                          mol_type = protein
                          organism = synthetic construct
SEQUENCE: 10
DLARMAAA                                                                        8

SEQ ID NO: 11             moltype = AA   length = 8
FEATURE                   Location/Qualifiers
REGION                    1..8
                          note = peptide
PEPTIDE                   1..8
source                    1..8
                          mol_type = protein
                          organism = synthetic construct
SEQUENCE: 11
DQGSITAH                                                                        8

SEQ ID NO: 12             moltype = AA   length = 8
FEATURE                   Location/Qualifiers
REGION                    1..8
                          note = peptide
```

```
PEPTIDE                 1..8
source                  1..8
                        mol_type = protein
                        organism = synthetic construct
SEQUENCE: 12
DRTPGVNV                                                                    8

SEQ ID NO: 13           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 13
DTDTLSPG                                                                    8

SEQ ID NO: 14           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 14
EEDAQLLI                                                                    8

SEQ ID NO: 15           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 15
EKLNDWPT                                                                    8

SEQ ID NO: 16           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 16
ELNSARQV                                                                    8

SEQ ID NO: 17           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 17
ELQSFAGL                                                                    8

SEQ ID NO: 18           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 18
ENKSAPLP                                                                    8

SEQ ID NO: 19           moltype = AA   length = 8
FEATURE                 Location/Qualifiers
REGION                  1..8
                        note = peptide
PEPTIDE                 1..8
source                  1..8
```

```
                        mol_type = protein
                        organism = synthetic construct
SEQUENCE: 19
ERTAVKGN                                                              8

SEQ ID NO: 20           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 20
GGIQTVVT                                                              8

SEQ ID NO: 21           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 21
GGSPLAHP                                                              8

SEQ ID NO: 22           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 22
GGTAAQGV                                                              8

SEQ ID NO: 23           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 23
GKMASGSL                                                              8

SEQ ID NO: 24           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 24
GKQPVQPY                                                              8

SEQ ID NO: 25           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 25
GNPHTGST                                                              8

SEQ ID NO: 26           moltype = AA   length = 8
FEATURE                 Location/Qualifiers
REGION                  1..8
                        note = peptide
PEPTIDE                 1..8
source                  1..8
                        mol_type = protein
                        organism = synthetic construct
```

```
SEQUENCE: 26
GPTLGGSG                                                                        8

SEQ ID NO: 27           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 27
GQRGLPIA                                                                        8

SEQ ID NO: 28           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 28
GREPRRLH                                                                        8

SEQ ID NO: 29           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 29
GTPQTTKE                                                                        8

SEQ ID NO: 30           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 30
GVTERPNR                                                                        8

SEQ ID NO: 31           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 31
HLGDNLAR                                                                        8

SEQ ID NO: 32           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 32
HPGSGAGP                                                                        8

SEQ ID NO: 33           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 33
HQVTSSGA                                                                        8
```

```
SEQ ID NO: 34          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 34
HVGSQMHA                                                                 8

SEQ ID NO: 35          moltype = AA  length = 8
FEATURE                Location/Qualifiers
REGION                 1..8
                       note = peptide
PEPTIDE                1..8
UNSURE                 3
source                 1..8
                       mol_type = protein
                       organism = synthetic construct
SEQUENCE: 35
IGXTVPMQ                                                                 8

SEQ ID NO: 36          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 36
KFTRDGPY                                                                 8

SEQ ID NO: 37          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 37
KGPAEQGH                                                                 8

SEQ ID NO: 38          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 38
LAHSPRLW                                                                 8

SEQ ID NO: 39          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 39
LERNRDSD                                                                 8

SEQ ID NO: 40          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 40
LETHTSLT                                                                 8
```

```
SEQ ID NO: 41            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 41
LHDGKYST                                                                  8

SEQ ID NO: 42            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 42
LKATGRGK                                                                  8

SEQ ID NO: 43            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 43
LLPGSADG                                                                  8

SEQ ID NO: 44            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 44
LLVTARSH                                                                  8

SEQ ID NO: 45            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 45
LPEVEPTN                                                                  8

SEQ ID NO: 46            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 46
LPWENSSQ                                                                  8

SEQ ID NO: 47            moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 47
LQRNSDAN                                                                  8

SEQ ID NO: 48            moltype = AA   length = 8
FEATURE                  Location/Qualifiers
```

```
REGION                  1..8
                        note = peptide
PEPTIDE                 1..8
source                  1..8
                        mol_type = protein
                        organism = synthetic construct
SEQUENCE: 48
LQSAPRAT                                                                  8

SEQ ID NO: 49           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 49
MLGSQVPT                                                                  8

SEQ ID NO: 50           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 50
MSGQGYQA                                                                  8

SEQ ID NO: 51           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 51
NPGRDFRD                                                                  8

SEQ ID NO: 52           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 52
NQPSDYVS                                                                  8

SEQ ID NO: 53           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 53
NSVGSADK                                                                  8

SEQ ID NO: 54           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 54
NVQRTQRG                                                                  8

SEQ ID NO: 55           moltype = AA  length = 8
FEATURE                 Location/Qualifiers
REGION                  1..8
                        note = peptide
```

```
                              -continued

PEPTIDE                  1..8
source                   1..8
                         mol_type = protein
                         organism = synthetic construct
SEQUENCE: 55
PAQLNGPR                                                                    8

SEQ ID NO: 56            moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 56
PERERLPR                                                                    8

SEQ ID NO: 57            moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 57
PGNGSHTM                                                                    8

SEQ ID NO: 58            moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 58
PIPGTPQP                                                                    8

SEQ ID NO: 59            moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 59
PMSVPASN                                                                    8

SEQ ID NO: 60            moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 60
PRPTVVGT                                                                    8

SEQ ID NO: 61            moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 61
PRTNRGPE                                                                    8

SEQ ID NO: 62            moltype = AA  length = 8
FEATURE                  Location/Qualifiers
REGION                   1..8
                         note = peptide
PEPTIDE                  1..8
source                   1..8
```

```
                                                     mol_type = protein
                                                     organism = synthetic construct
SEQUENCE: 62
PVANPTTA                                                                                 8

SEQ ID NO: 63           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 63
PVLGGPPK                                                                                 8

SEQ ID NO: 64           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 64
QGSRQGSS                                                                                 8

SEQ ID NO: 65           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 65
QMAETPIS                                                                                 8

SEQ ID NO: 66           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 66
QMLGIGRS                                                                                 8

SEQ ID NO: 67           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 67
QSGDSALN                                                                                 8

SEQ ID NO: 68           moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 68
RAGLTSSE                                                                                 8

SEQ ID NO: 69           moltype = AA   length = 8
FEATURE                 Location/Qualifiers
REGION                  1..8
                        note = peptide
PEPTIDE                 1..8
source                  1..8
                        mol_type = protein
                        organism = synthetic construct
```

```
SEQUENCE: 69
RLDNTGVG                                                                         8

SEQ ID NO: 70           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 70
RMPGKPYS                                                                         8

SEQ ID NO: 71           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 71
RVAGASQP                                                                         8

SEQ ID NO: 72           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 72
RVESSQLE                                                                         8

SEQ ID NO: 73           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 73
SARTGASE                                                                         8

SEQ ID NO: 74           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 74
SERNRASM                                                                         8

SEQ ID NO: 75           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 75
SIDVRMAA                                                                         8

SEQ ID NO: 76           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 76
SRDGHILR                                                                         8
```

```
SEQ ID NO: 77          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 77
SRQVVLPG                                                                    8

SEQ ID NO: 78          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 78
SSRGYTST                                                                    8

SEQ ID NO: 79          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 79
SSVVSQGP                                                                    8

SEQ ID NO: 80          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 80
SVAESGRE                                                                    8

SEQ ID NO: 81          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 81
TALTANTQ                                                                    8

SEQ ID NO: 82          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 82
TESSVGNL                                                                    8

SEQ ID NO: 83          moltype = AA  length = 8
FEATURE                Location/Qualifiers
REGION                 1..8
                       note = peptide
PEPTIDE                1..8
source                 1..8
                       mol_type = protein
                       organism = synthetic construct
SEQUENCE: 83
TGREGANL                                                                    8

SEQ ID NO: 84          moltype = AA  length = 8
```

```
FEATURE               Location/Qualifiers
REGION                1..8
                      note = peptide
PEPTIDE               1..8
source                1..8
                      mol_type = protein
                      organism = synthetic construct
SEQUENCE: 84
TLSEPPKK                                                                        8

SEQ ID NO: 85         moltype = AA   length = 8
FEATURE               Location/Qualifiers
REGION                1..8
                      note = peptide
PEPTIDE               1..8
source                1..8
                      mol_type = protein
                      organism = synthetic construct
SEQUENCE: 85
TNAVSGKS                                                                        8

SEQ ID NO: 86         moltype = AA   length = 8
FEATURE               Location/Qualifiers
REGION                1..8
                      note = peptide
PEPTIDE               1..8
source                1..8
                      mol_type = protein
                      organism = synthetic construct
SEQUENCE: 86
TRAPTIHL                                                                        8

SEQ ID NO: 87         moltype = AA   length = 8
FEATURE               Location/Qualifiers
REGION                1..8
                      note = peptide
PEPTIDE               1..8
source                1..8
                      mol_type = protein
                      organism = synthetic construct
SEQUENCE: 87
TRESTDRG                                                                        8

SEQ ID NO: 88         moltype = AA   length = 8
FEATURE               Location/Qualifiers
REGION                1..8
                      note = peptide
PEPTIDE               1..8
source                1..8
                      mol_type = protein
                      organism = synthetic construct
SEQUENCE: 88
TVAAAPNL                                                                        8

SEQ ID NO: 89         moltype = AA   length = 8
FEATURE               Location/Qualifiers
REGION                1..8
                      note = peptide
PEPTIDE               1..8
source                1..8
                      mol_type = protein
                      organism = synthetic construct
SEQUENCE: 89
TYHNNTPR                                                                        8

SEQ ID NO: 90         moltype = AA   length = 8
FEATURE               Location/Qualifiers
REGION                1..8
                      note = peptide
PEPTIDE               1..8
source                1..8
                      mol_type = protein
                      organism = synthetic construct
SEQUENCE: 90
VSNSTRTS                                                                        8

SEQ ID NO: 91         moltype = AA   length = 8
FEATURE               Location/Qualifiers
REGION                1..8
```

```
                        note = peptide
PEPTIDE                 1..8
source                  1..8
                        mol_type = protein
                        organism = synthetic construct
SEQUENCE: 91
VTLQIDTK                                                                        8

SEQ ID NO: 92           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 92
WMSRPGPT                                                                        8

SEQ ID NO: 93           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 93
WPYRGLTQ                                                                        8

SEQ ID NO: 94           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 94
WRRQGSRA                                                                        8

SEQ ID NO: 95           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 95
YAQRFAKM                                                                        8

SEQ ID NO: 96           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 96
YNSPRQTV                                                                        8

SEQ ID NO: 97           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 97
APTNFAHP                                                                        8

SEQ ID NO: 98           moltype = AA  length = 8
FEATURE                 Location/Qualifiers
REGION                  1..8
                        note = peptide
PEPTIDE                 1..8
```

```
                            -continued source                  1..8
                        mol_type = protein
                        organism = synthetic construct
SEQUENCE: 98
AQTNLAAG                                                                8

SEQ ID NO: 99           moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 99
ASLPNLGQ                                                                8

SEQ ID NO: 100          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 100
DYMHNTGL                                                                8

SEQ ID NO: 101          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 101
DYMHTTGL                                                                8

SEQ ID NO: 102          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 102
ERNAWHAG                                                                8

SEQ ID NO: 103          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 103
ETQATPMP                                                                8

SEQ ID NO: 104          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 104
EWEDSARS                                                                8

SEQ ID NO: 105          moltype = AA  length = 8
FEATURE                 Location/Qualifiers
REGION                  1..8
                        note = peptide
PEPTIDE                 1..8
source                  1..8
                        mol_type = protein
```

```
                                      organism = synthetic construct
SEQUENCE: 105
FTGDTDTL                                                                            8

SEQ ID NO: 106          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 106
FTNRTSTT                                                                            8

SEQ ID NO: 107          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 107
GDYTVQRP                                                                            8

SEQ ID NO: 108          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 108
GGLRTDYG                                                                            8

SEQ ID NO: 109          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 109
GPQEGSER                                                                            8

SEQ ID NO: 110          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 110
GSNHTQSL                                                                            8

SEQ ID NO: 111          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 111
HDRDTRQA                                                                            8

SEQ ID NO: 112          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 112
```

```
LDQNRRPQ                                                                        8

SEQ ID NO: 113          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 113
LEQQRGAS                                                                        8

SEQ ID NO: 114          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 114
LGGNAQGL                                                                        8

SEQ ID NO: 115          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 115
LLVTTRSH                                                                        8

SEQ ID NO: 116          moltype = AA  length = 7
FEATURE                 Location/Qualifiers
REGION                  1..7
                        note = peptide
PEPTIDE                 1..7
source                  1..7
                        mol_type = protein
                        organism = synthetic construct
SEQUENCE: 116
LVTNTTR                                                                         7

SEQ ID NO: 117          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 117
MESQRANS                                                                        8

SEQ ID NO: 118          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 118
MISQTLMA                                                                        8

SEQ ID NO: 119          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 119
MMSQSLRA                                                                        8
```

-continued

```
SEQ ID NO: 120           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 120
NNVQSALN                                                                 8

SEQ ID NO: 121           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 121
NSARTQLS                                                                 8

SEQ ID NO: 122           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 122
PQWNRTPL                                                                 8

SEQ ID NO: 123           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 123
PRFNNSSL                                                                 8

SEQ ID NO: 124           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 124
PVDGGRHL                                                                 8

SEQ ID NO: 125           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 125
PWFNKSSL                                                                 8

SEQ ID NO: 126           moltype = AA   length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 126
QDMNSQRS                                                                 8

SEQ ID NO: 127           moltype = AA   length = 8
FEATURE                  Location/Qualifiers
```

```
                    REGION           1..8
                                     note = peptide
                    PEPTIDE          1..8
                    source           1..8
                                     mol_type = protein
                                     organism = synthetic construct
SEQUENCE: 127
QGASNSQL                                                                   8

SEQ ID NO: 128      moltype = AA   length = 8
FEATURE             Location/Qualifiers
REGION              1..8
                    note = peptide
PEPTIDE             1..8
source              1..8
                    mol_type = protein
                    organism = synthetic construct
SEQUENCE: 128
QQNGTRPS                                                                   8

SEQ ID NO: 129      moltype = AA   length = 8
FEATURE             Location/Qualifiers
REGION              1..8
                    note = peptide
PEPTIDE             1..8
source              1..8
                    mol_type = protein
                    organism = synthetic construct
SEQUENCE: 129
QRSAYPTS                                                                   8

SEQ ID NO: 130      moltype = AA   length = 8
FEATURE             Location/Qualifiers
REGION              1..8
                    note = peptide
PEPTIDE             1..8
source              1..8
                    mol_type = protein
                    organism = synthetic construct
SEQUENCE: 130
QRTPSITP                                                                   8

SEQ ID NO: 131      moltype = AA   length = 8
FEATURE             Location/Qualifiers
REGION              1..8
                    note = peptide
PEPTIDE             1..8
source              1..8
                    mol_type = protein
                    organism = synthetic construct
SEQUENCE: 131
QWMKEQAG                                                                   8

SEQ ID NO: 132      moltype = AA   length = 8
FEATURE             Location/Qualifiers
REGION              1..8
                    note = peptide
PEPTIDE             1..8
source              1..8
                    mol_type = protein
                    organism = synthetic construct
SEQUENCE: 132
RDGRHPSE                                                                   8

SEQ ID NO: 133      moltype = AA   length = 8
FEATURE             Location/Qualifiers
REGION              1..8
                    note = peptide
PEPTIDE             1..8
source              1..8
                    mol_type = protein
                    organism = synthetic construct
SEQUENCE: 133
RGTVTVEQ                                                                   8

SEQ ID NO: 134      moltype = AA   length = 8
FEATURE             Location/Qualifiers
REGION              1..8
                    note = peptide
```

```
PEPTIDE                     1..8
source                      1..8
                            mol_type = protein
                            organism = synthetic construct
SEQUENCE: 134
RPANHSTA                                                                        8

SEQ ID NO: 135              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 135
RQGDADTL                                                                        8

SEQ ID NO: 136              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 136
SATISLQV                                                                        8

SEQ ID NO: 137              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 137
SHTNLRDT                                                                        8

SEQ ID NO: 138              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 138
SRMGETPQ                                                                        8

SEQ ID NO: 139              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 139
SSGYLTAN                                                                        8

SEQ ID NO: 140              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 140
TGNSPEQA                                                                        8

SEQ ID NO: 141              moltype = AA   length = 8
FEATURE                     Location/Qualifiers
REGION                      1..8
                            note = peptide
PEPTIDE                     1..8
source                      1..8
```

```
                            mol_type = protein
                            organism = synthetic construct
SEQUENCE: 141
THSQGRLA                                                                    8

SEQ ID NO: 142              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 142
TPIVGSNV                                                                    8

SEQ ID NO: 143              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 143
TPPKSPSM                                                                    8

SEQ ID NO: 144              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 144
TRMDERSP                                                                    8

SEQ ID NO: 145              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 145
TTATTSIT                                                                    8

SEQ ID NO: 146              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 146
VVQGEQKR                                                                    8

SEQ ID NO: 147              moltype = AA   length = 8
FEATURE                     Location/Qualifiers
REGION                      1..8
                            note = peptide
PEPTIDE                     1..8
source                      1..8
                            mol_type = protein
                            organism = synthetic construct
SEQUENCE: 147
WNDRSGER                                                                    8

SEQ ID NO: 148              moltype = AA   length = 8
FEATURE                     Location/Qualifiers
REGION                      1..8
                            note = peptide
PEPTIDE                     1..8
source                      1..8
                            mol_type = protein
                            organism = synthetic construct
```

```
SEQUENCE: 148
WSQDAVKG                                                                    8

SEQ ID NO: 149          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 149
WTGGGSGT                                                                    8

SEQ ID NO: 150          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 150
AGAAYTPA                                                                    8

SEQ ID NO: 151          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 151
APSVSREK                                                                    8

SEQ ID NO: 152          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 152
DYMHKTGL                                                                    8

SEQ ID NO: 153          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 153
GGMNETTR                                                                    8

SEQ ID NO: 154          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 154
GGSAFVTG                                                                    8

SEQ ID NO: 155          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 155
GNSHTGSS                                                                    8
```

```
SEQ ID NO: 156          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 156
NSARTQLS                                                                   8

SEQ ID NO: 157          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 157
PLTILNRH                                                                   8

SEQ ID NO: 158          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 158
QGTRTNPP                                                                   8

SEQ ID NO: 159          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 159
QSSAMPRN                                                                   8

SEQ ID NO: 160          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 160
SHNSQPVA                                                                   8

SEQ ID NO: 161          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 161
TAQGAAFR                                                                   8

SEQ ID NO: 162          moltype = AA   length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 162
TPGLNNAR                                                                   8

SEQ ID NO: 163          moltype = AA   length = 8
```

```
FEATURE              Location/Qualifiers
REGION               1..8
                     note = peptide
PEPTIDE              1..8
source               1..8
                     mol_type = protein
                     organism = synthetic construct
SEQUENCE: 163
TSLGTPEA                                                                8

SEQ ID NO: 164       moltype = AA   length = 8
FEATURE              Location/Qualifiers
REGION               1..8
                     note = peptide
PEPTIDE              1..8
source               1..8
                     mol_type = protein
                     organism = synthetic construct
SEQUENCE: 164
TTNLAKNS                                                                8

SEQ ID NO: 165       moltype = AA   length = 8
FEATURE              Location/Qualifiers
REGION               1..8
                     note = peptide
PEPTIDE              1..8
source               1..8
                     mol_type = protein
                     organism = synthetic construct
SEQUENCE: 165
WSPDAVEG                                                                8

SEQ ID NO: 166       moltype = AA   length = 7
FEATURE              Location/Qualifiers
REGION               1..7
                     note = peptide
PEPTIDE              1..7
source               1..7
                     mol_type = protein
                     organism = synthetic construct
SEQUENCE: 166
WTGGRHL                                                                 7

SEQ ID NO: 167       moltype = AA   length = 8
FEATURE              Location/Qualifiers
REGION               1..8
                     note = peptide
PEPTIDE              1..8
source               1..8
                     mol_type = protein
                     organism = synthetic construct
SEQUENCE: 167
AVAGDRLL                                                                8

SEQ ID NO: 168       moltype = AA   length = 8
FEATURE              Location/Qualifiers
REGION               1..8
                     note = peptide
PEPTIDE              1..8
source               1..8
                     mol_type = protein
                     organism = synthetic construct
SEQUENCE: 168
DLLTRSVS                                                                8

SEQ ID NO: 169       moltype = AA   length = 8
FEATURE              Location/Qualifiers
REGION               1..8
                     note = peptide
PEPTIDE              1..8
source               1..8
                     mol_type = protein
                     organism = synthetic construct
SEQUENCE: 169
EWKTQLAL                                                                8

SEQ ID NO: 170       moltype = AA   length = 8
FEATURE              Location/Qualifiers
REGION               1..8
```

```
                        note = peptide
PEPTIDE                 1..8
source                  1..8
                        mol_type = protein
                        organism = synthetic construct
SEQUENCE: 170
GNINVVPH                                                                         8

SEQ ID NO: 171          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 171
GSPAASSW                                                                         8

SEQ ID NO: 172          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 172
KHSLTLES                                                                         8

SEQ ID NO: 173          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 173
KPVSTDTF                                                                         8

SEQ ID NO: 174          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 174
LDRSGSTG                                                                         8

SEQ ID NO: 175          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 175
LGAQNHVV                                                                         8

SEQ ID NO: 176          moltype = AA  length = 8
FEATURE                 Location/Qualifiers
REGION                  1..8
                        note = peptide
PEPTIDE                 1..8
source                  1..8
                        mol_type = protein
                        organism = synthetic construct
SEQUENCE: 176
LMATDYGP                                                                         8

SEQ ID NO: 177          moltype = AA  length = 8
FEATURE                 Location/Qualifiers
REGION                  1..8
                        note = peptide
PEPTIDE                 1..8
```

```
source                   1..8
                         mol_type = protein
                         organism = synthetic construct
SEQUENCE: 177
LRATDYGP                                                                    8

SEQ ID NO: 178           moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 178
MERTEPLG                                                                    8

SEQ ID NO: 179           moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 179
NDGLRLHL                                                                    8

SEQ ID NO: 180           moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 180
NLSAHSHA                                                                    8

SEQ ID NO: 181           moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 181
NLSAHSHD                                                                    8

SEQ ID NO: 182           moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 182
RALDLVTR                                                                    8

SEQ ID NO: 183           moltype = AA  length = 8
FEATURE                  Location/Qualifiers
REGION                   1..8
                         note = peptide
PEPTIDE                  1..8
source                   1..8
                         mol_type = protein
                         organism = synthetic construct
SEQUENCE: 183
SAGMARNS                                                                    8

SEQ ID NO: 184           moltype = AA  length = 8
FEATURE                  Location/Qualifiers
REGION                   1..8
                         note = peptide
PEPTIDE                  1..8
source                   1..8
                         mol_type = protein
```

```
                                  -continued
                       organism = synthetic construct
SEQUENCE: 184
SGQRVGSA                                                              8

SEQ ID NO: 185         moltype = AA   length = 8
FEATURE                Location/Qualifiers
REGION                 1..8
                       note = peptide
PEPTIDE                1..8
source                 1..8
                       mol_type = protein
                       organism = synthetic construct
SEQUENCE: 185
SGQRVGSD                                                              8

SEQ ID NO: 186         moltype = AA   length = 8
FEATURE                Location/Qualifiers
REGION                 1..8
                       note = peptide
PEPTIDE                1..8
source                 1..8
                       mol_type = protein
                       organism = synthetic construct
SEQUENCE: 186
TGRPEQPK                                                              8

SEQ ID NO: 187         moltype = AA   length = 8
FEATURE                Location/Qualifiers
REGION                 1..8
                       note = peptide
PEPTIDE                1..8
source                 1..8
                       mol_type = protein
                       organism = synthetic construct
SEQUENCE: 187
THSPIKLP                                                              8

SEQ ID NO: 188         moltype = AA   length = 8
FEATURE                Location/Qualifiers
REGION                 1..8
                       note = peptide
PEPTIDE                1..8
source                 1..8
                       mol_type = protein
                       organism = synthetic construct
SEQUENCE: 188
TQFSQAQR                                                              8

SEQ ID NO: 189         moltype = AA   length = 8
FEATURE                Location/Qualifiers
REGION                 1..8
                       note = peptide
PEPTIDE                1..8
source                 1..8
                       mol_type = protein
                       organism = synthetic construct
SEQUENCE: 189
VGDSANLR                                                              8

SEQ ID NO: 190         moltype = DNA   length = 10
FEATURE                Location/Qualifiers
source                 1..10
                       mol_type = other DNA
                       organism = adeno-associated virus
SEQUENCE: 190
cgagccaacc                                                           10

SEQ ID NO: 191         moltype = DNA   length = 27
FEATURE                Location/Qualifiers
source                 1..27
                       mol_type = other DNA
                       organism = adeno-associated virus
SEQUENCE: 191
caaaccctgg ccgtgccctt caaggca                                        27

SEQ ID NO: 192         moltype = DNA   length = 2211
FEATURE                Location/Qualifiers
source                 1..2211
                       mol_type = other DNA
```

```
                organism = adeno-associated virus
SEQUENCE: 192
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt ggggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccccctcag tgtgggatct   600
cttacaatgg cttcaggtgg tggcgcacca gtggcagaca taacgaagg tgccgatgga   660
gtgggtagtt cctcggggaaa ttggcattgc gattcccaat ggctgggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtgccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caacttccac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa acagcaagc gctggaaccc ggagatccag  2100
tacacttcca actattacaa gtctaataat gttgaatttc tgttaatac tgaaggtgta  2160
tatagtgaac ccgcccccat tggcaccaga tacctgactc gtaatctgta a            2211

SEQ ID NO: 193     moltype = DNA   length = 2211
FEATURE            Location/Qualifiers
source             1..2211
                   mol_type = other DNA
                   organism = adeno-associated virus
SEQUENCE: 193
atggctgctg acggttatct tccagattgg ctcgaggaca acctttctga aggcattcgt    60
gagtggtggg ctctgaaacc tggagtccct caacccaaag cgaaccaaca acaccaggac   120
aaccgtcggg gtcttgtgct tccgggttac aaataccctcg gacccggtaa cggactcgac   180
aaaggagagc cggtcaacga ggcggacgcg gcagccctcg aacacgacaa agcttacgac   240
cagcagctca aggccggtga caacccgtac ctcaagtaca accacgcgga cgccgagttc   300
caggagcgtc ttcaagaaga tacgtctttt ggggggcaacc ttggcagagc agtcttccag   360
gccaaaaaga ggatccttga gcctcttggt ctggttgagg aagcagctaa acggctcct   420
ggaaagaaga ggcctgtaga tcagtctcct caggaaccgg actcatcatc tggtgttggc   480
aaatcgggca aacagcctgc cagaaaaaga ctaaatttcg gtcagactgg cgactcagag   540
tcagtcccag accctcaacc tctcggagaa ccaccagcag cccccacaag tttgggatct   600
aatacaatgg cttcaggcgg tggcgcacca atggcagaca taacgagggg tgccgatgga   660
gtgggtaatt cctcaggaaa ttggcattgc gattcccaat ggctgggga cagagtcatc   720
accaccagca ccagaacctg ggccctgccc acttacaaca accatctcta caagcaaatc   780
tccagccaat caggagcttc aaacgacaac cactactttg gctacagcac ccttgggggg   840
tattttgact ttaacagatt ccactgccac ttctcaccac gtgactggca gcgactcatt   900
aacaacaact ggggattccg gcccaagaaa ctcagcttca gcttcaa catccaagtt   960
aaagaggtca cgcagaacga tggcacgacg actattgcca ataaccttac cagcacggtt  1020
caagtgttta cggactcgga gtatcagctc ccgtacgtgc tcggtcggc gcaaagcgc  1080
tgtctcccgc cgtttccagc ggacgtcttc atggtccctc agtatggata cctcaccctg  1140
aacaacggaa gtcaagcggt gggacgctca tccttttact gcctggagta cttcccttcg  1200
cagatgctaa ggactggaaa taacttccaa ttcagctata ccttcgagga tgtacctttt  1260
cacagcagct acgctcacag ccagagtttg gatcgcttga tgaatcctct tattgatcag  1320
tatctgtact acctgaacag aacgcaagga acaacctctg gaacaaccaa ccaatcacgg  1380
ctgcttttta gccaggctgg gcctcagtct atgtctttgc aggccagaaa ttggctacct  1440
gggccctgct accggcaaca gagacttca aagactgcta cgacaacaa caacagtaac  1500
tttcttgga cagcggccag caaatatcat ctcaatggcc gcgactcgct ggtgaatcca  1560
ggaccagcta tggccagtca caaggacgat gaagaaaat ttttcccctat gcacggcaat  1620
ctaataattg gcaaagaagg acaacggca agtaacgaa aattagataa tgtaatgatt  1680
acggatgaag aagagattcg taccaccaat cctgtggcaa cagagcagta ggaactgtg  1740
gcaaataact tgcagagctc aaatacagct cccacgacta gaactgtcaa tgatcagggg  1800
gccttacctg gcatggtgtg gcaagatcgt gacgtgtacc ttcaaggacc tatctgggca  1860
aagattcctc acacggatgg acactttcat ccttctcctc tgatgggagg ctttggactg  1920
aaacatccgc ctcctcaaat catgatcaaa aatactccgg taccggcaaa tcctccgacg  1980
```

```
actttcagcc cggccaagtt tgcttcattt atcactcagt actccactgg acaggtcagc    2040
gtggaaattg agtgggagct acagaaagaa aacagcaaac gttggaatcc agagattcag    2100
tacacttcca actacaacaa gtctgttaat gtggacttta ctgtagacac taatggtgtt    2160
tatagtgaac ctcgccctat tggaacccgg tatctcacac gaaacttgta a             2211
```

```
SEQ ID NO: 194          moltype = DNA   length = 41
FEATURE                 Location/Qualifiers
source                  1..41
                        mol_type = other DNA
                        organism = adeno-associated virus
SEQUENCE: 194
gcaagaaagg ccagcagccc gccagaaaga gactcaattt c                         41

SEQ ID NO: 195          moltype = DNA   length = 131
FEATURE                 Location/Qualifiers
source                  1..131
                        mol_type = other DNA
                        organism = adeno-associated virus
SEQUENCE: 195
cgggtattgg caaatcgggt gcacagcccg ctaaaagag actcaatttc ggtcagactg       60
gcgacacaga gtcagtccca gaccctcaac caatcggaga acctcccgca gcccctcag      120
gtgtgggatc t                                                          131

SEQ ID NO: 196          moltype = DNA   length = 63
FEATURE                 Location/Qualifiers
source                  1..63
                        mol_type = other DNA
                        organism = adeno-associated virus
SEQUENCE: 196
actgaaggtg tatatagtga accccgcccc attggcacca gatacctgac tcgtaatctg      60
taa                                                                    63

SEQ ID NO: 197          moltype = DNA   length = 131
FEATURE                 Location/Qualifiers
misc_feature            1..131
                        note = Codon modified AAV9
misc_feature            1..131
source                  1..131
                        mol_type = other DNA
                        organism = synthetic construct
SEQUENCE: 197
cgggtattgg caaatcgggt gcacagcctg ccaagaagcg cctgaacttt ggccagaccg      60
gcgacacaga gagcgttccg gaccctcaac caatcggaga acctcccgca gcccctcag      120
gtgtgggatc t                                                          131

SEQ ID NO: 198          moltype = DNA   length = 63
FEATURE                 Location/Qualifiers
misc_feature            1..63
                        note = Codon modified AAV9
misc_feature            1..63
source                  1..63
                        mol_type = other DNA
                        organism = synthetic construct
SEQUENCE: 198
actgaaggtg tatatagtga accccgccca atcgggacaa gatatctgac aagaaacctg      60
taa                                                                    63

SEQ ID NO: 199          moltype = DNA   length = 10
FEATURE                 Location/Qualifiers
source                  1..10
                        mol_type = other DNA
                        organism = adeno-associated virus
SEQUENCE: 199
cttaccagca                                                             10

SEQ ID NO: 200          moltype = DNA   length = 10
FEATURE                 Location/Qualifiers
source                  1..10
                        mol_type = other DNA
                        organism = adeno-associated virus
SEQUENCE: 200
tttaccttca                                                             10

SEQ ID NO: 201          moltype = DNA   length = 10
FEATURE                 Location/Qualifiers
source                  1..10
                        mol_type = other DNA
                        organism = adeno-associated virus
SEQUENCE: 201
```

```
tataccttcg                                                                                       10

SEQ ID NO: 202           moltype = DNA  length = 10
FEATURE                  Location/Qualifiers
source                   1..10
                         mol_type = other DNA
                         organism = adeno-associated virus
SEQUENCE: 202
attacctgaa                                                                                       10

SEQ ID NO: 203           moltype = DNA  length = 10
FEATURE                  Location/Qualifiers
source                   1..10
                         mol_type = other DNA
                         organism = adeno-associated virus
SEQUENCE: 203
gctacctgga                                                                                       10

SEQ ID NO: 204           moltype = DNA  length = 10
FEATURE                  Location/Qualifiers
source                   1..10
                         mol_type = other DNA
                         organism = adeno-associated virus
SEQUENCE: 204
tttacctgga                                                                                       10

SEQ ID NO: 205           moltype = DNA  length = 10
FEATURE                  Location/Qualifiers
source                   1..10
                         mol_type = other DNA
                         organism = adeno-associated virus
SEQUENCE: 205
attacctggc                                                                                       10

SEQ ID NO: 206           moltype = DNA  length = 10
FEATURE                  Location/Qualifiers
source                   1..10
                         mol_type = other DNA
                         organism = adeno-associated virus
SEQUENCE: 206
cttacctggc                                                                                       10

SEQ ID NO: 207           moltype = DNA  length = 10
FEATURE                  Location/Qualifiers
source                   1..10
                         mol_type = other DNA
                         organism = adeno-associated virus
SEQUENCE: 207
tgtacctgca                                                                                       10

SEQ ID NO: 208           moltype = DNA  length = 10
FEATURE                  Location/Qualifiers
source                   1..10
                         mol_type = other DNA
                         organism = adeno-associated virus
SEQUENCE: 208
gttaccttac                                                                                       10

SEQ ID NO: 209           moltype = DNA  length = 10
FEATURE                  Location/Qualifiers
source                   1..10
                         mol_type = other DNA
                         organism = adeno-associated virus
SEQUENCE: 209
gatacctgac                                                                                       10

SEQ ID NO: 210           moltype = DNA  length = 10
FEATURE                  Location/Qualifiers
source                   1..10
                         mol_type = other DNA
                         organism = adeno-associated virus
SEQUENCE: 210
cttacccgtc                                                                                       10

SEQ ID NO: 211           moltype = DNA  length = 10
FEATURE                  Location/Qualifiers
source                   1..10
                         mol_type = other DNA
                         organism = adeno-associated virus
```

| | | |
|---|---|---|
| SEQUENCE: 211 ctcacacgaa | | 10 |
| SEQ ID NO: 212 FEATURE source | moltype = DNA length = 10 Location/Qualifiers 1..10 mol_type = other DNA organism = adeno-associated virus | |
| SEQUENCE: 212 agcgtctgca | | 10 |
| SEQ ID NO: 213 FEATURE source | moltype = DNA length = 10 Location/Qualifiers 1..10 mol_type = other DNA organism = adeno-associated virus | |
| SEQUENCE: 213 ggctcctgga | | 10 |
| SEQ ID NO: 214 FEATURE source | moltype = DNA length = 10 Location/Qualifiers 1..10 mol_type = other DNA organism = adeno-associated virus | |
| SEQUENCE: 214 gcccgctaaa | | 10 |
| SEQ ID NO: 215 FEATURE source | moltype = DNA length = 10 Location/Qualifiers 1..10 mol_type = other DNA organism = adeno-associated virus | |
| SEQUENCE: 215 tcaccctgaa | | 10 |
| SEQ ID NO: 216 FEATURE source | moltype = DNA length = 10 Location/Qualifiers 1..10 mol_type = other DNA organism = adeno-associated virus | |
| SEQUENCE: 216 actgcctgga | | 10 |
| SEQ ID NO: 217 FEATURE source | moltype = DNA length = 10 Location/Qualifiers 1..10 mol_type = other DNA organism = adeno-associated virus | |
| SEQUENCE: 217 actacctgaa | | 10 |
| SEQ ID NO: 218 FEATURE source | moltype = DNA length = 10 Location/Qualifiers 1..10 mol_type = other DNA organism = adeno-associated virus | |
| SEQUENCE: 218 cgtttctaaa | | 10 |
| SEQ ID NO: 219 FEATURE source | moltype = DNA length = 10 Location/Qualifiers 1..10 mol_type = other DNA organism = adeno-associated virus | |
| SEQUENCE: 219 aaacactgca | | 10 |
| SEQ ID NO: 220 FEATURE source | moltype = DNA length = 10 Location/Qualifiers 1..10 mol_type = other DNA organism = adeno-associated virus | |
| SEQUENCE: 220 gggagctgca | | 10 |
| SEQ ID NO: 221 FEATURE source | moltype = AA length = 736 Location/Qualifiers 1..736 mol_type = protein | |

```
                         organism = adeno-associated virus
SEQUENCE: 221
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 222           moltype = AA  length = 736
FEATURE                  Location/Qualifiers
REGION                   1..736
                         note = synthesized
PEPTIDE                  1..736
source                   1..736
                         mol_type = protein
                         organism = synthetic construct
SEQUENCE: 222
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DAAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 223           moltype = DNA  length = 41
FEATURE                  Location/Qualifiers
source                   1..41
                         mol_type = other DNA
                         organism = adeno-associated virus
SEQUENCE: 223
gcaagaaagg ccagcagccc gccagaaaga gactcaattt c                        41

SEQ ID NO: 224           moltype = DNA  length = 41
FEATURE                  Location/Qualifiers
source                   1..41
                         mol_type = other DNA
                         organism = adeno-associated virus
SEQUENCE: 224
gcaagaaagg ccagcagccc gccggaaaga gactcaattt c                        41

SEQ ID NO: 225           moltype = DNA  length = 41
FEATURE                  Location/Qualifiers
source                   1..41
                         mol_type = other DNA
                         organism = adeno-associated virus
SEQUENCE: 225
gcaagaaagg ccagcagccc gctagaaaga gactgaactt t                        41

SEQ ID NO: 226           moltype = DNA  length = 41
FEATURE                  Location/Qualifiers
source                   1..41
                         mol_type = other DNA
                         organism = adeno-associated virus
SEQUENCE: 226
gcaagaaggg ccagcagccc gccagaaaga gactcaattt c                        41

SEQ ID NO: 227           moltype = DNA  length = 41
FEATURE                  Location/Qualifiers
source                   1..41
                         mol_type = other DNA
                         organism = adeno-associated virus
SEQUENCE: 227
gcaagaaagg ccagcggccc gctaaaaaga gactgaactt t                        41
```

```
SEQ ID NO: 228          moltype = DNA  length = 41
FEATURE                 Location/Qualifiers
source                  1..41
                        mol_type = other DNA
                        organism = adeno-associated virus
SEQUENCE: 228
gcaagaaagg ccagcagccc gctaaaaaga gactgaactt t                    41

SEQ ID NO: 229          moltype = DNA  length = 41
FEATURE                 Location/Qualifiers
source                  1..41
                        mol_type = other DNA
                        organism = adeno-associated virus
SEQUENCE: 229
gcaagaaagg ccagcagccc gctaaaaaga gactgagctt t                    41

SEQ ID NO: 230          moltype = DNA  length = 41
FEATURE                 Location/Qualifiers
source                  1..41
                        mol_type = other DNA
                        organism = adeno-associated virus
SEQUENCE: 230
gcaagaaagg ccaccagccc gcgagaaaga gactgaactt t                    41

SEQ ID NO: 231          moltype = DNA  length = 41
FEATURE                 Location/Qualifiers
source                  1..41
                        mol_type = other DNA
                        organism = adeno-associated virus
SEQUENCE: 231
gcaagacagg ccagcagccc gcgaaaaaga gactcaactt t                    41

SEQ ID NO: 232          moltype = DNA  length = 41
FEATURE                 Location/Qualifiers
source                  1..41
                        mol_type = other DNA
                        organism = adeno-associated virus
SEQUENCE: 232
gcaagaaagg ccagcagccc gctaaaaaga agctcaactt t                    41

SEQ ID NO: 233          moltype = DNA  length = 41
FEATURE                 Location/Qualifiers
source                  1..41
                        mol_type = other DNA
                        organism = adeno-associated virus
SEQUENCE: 233
gcaagaaagg ccagcagccc gctaaaaaga gactcaactt t                    41

SEQ ID NO: 234          moltype = DNA  length = 41
FEATURE                 Location/Qualifiers
source                  1..41
                        mol_type = other DNA
                        organism = adeno-associated virus
SEQUENCE: 234
gcaagaaagg ccagcagccc gcgaaaaaga gactcaactt t                    41

SEQ ID NO: 235          moltype = DNA  length = 40
FEATURE                 Location/Qualifiers
source                  1..40
                        mol_type = other DNA
                        organism = adeno-associated virus
SEQUENCE: 235
gcaagtcagg ccagcagccc gcgaaaaaga gactgaattt                      40

SEQ ID NO: 236          moltype = DNA  length = 41
FEATURE                 Location/Qualifiers
source                  1..41
                        mol_type = other DNA
                        organism = adeno-associated virus
SEQUENCE: 236
gcaagtcagg ccggcagccc gcgaaaaaga gactgaattt t                    41

SEQ ID NO: 237          moltype = DNA  length = 41
FEATURE                 Location/Qualifiers
source                  1..41
                        mol_type = other DNA
                        organism = adeno-associated virus
SEQUENCE: 237
gcaagaaagg ccaacagccc gccagaaaaa gactcaattt t                    41
```

```
SEQ ID NO: 238          moltype = DNA   length = 41
FEATURE                 Location/Qualifiers
source                  1..41
                        mol_type = other DNA
                        organism = adeno-associated virus
SEQUENCE: 238
gcaagacagg ccagcagccc gctaaaaaga gactcaattt t                        41

SEQ ID NO: 239          moltype = DNA   length = 41
FEATURE                 Location/Qualifiers
source                  1..41
                        mol_type = other DNA
                        organism = adeno-associated virus
SEQUENCE: 239
gcaagaacgg ccagccgccc gctaaaaaga agctcaactt t                        41

SEQ ID NO: 240          moltype = DNA   length = 41
FEATURE                 Location/Qualifiers
source                  1..41
                        mol_type = other DNA
                        organism = adeno-associated virus
SEQUENCE: 240
gcaaaaaagg ccagcagccc gctaaaaaga agctcaattt t                        41

SEQ ID NO: 241          moltype = DNA   length = 40
FEATURE                 Location/Qualifiers
source                  1..40
                        mol_type = other DNA
                        organism = adeno-associated virus
SEQUENCE: 241
gaaaggcggg ccagcagcct gcaagaaaaa gatgaatttt                          40

SEQ ID NO: 242          moltype = DNA   length = 40
FEATURE                 Location/Qualifiers
source                  1..40
                        mol_type = other DNA
                        organism = adeno-associated virus
SEQUENCE: 242
gaaaagcggg caaccagcct gcaagaaaaa gatgaatttc                          40

SEQ ID NO: 243          moltype = DNA   length = 41
FEATURE                 Location/Qualifiers
source                  1..41
                        mol_type = other DNA
                        organism = adeno-associated virus
SEQUENCE: 243
gaaaagcggg ccagcagcct gcaagaaaga gattgaattt c                        41

SEQ ID NO: 244          moltype = DNA   length = 41
FEATURE                 Location/Qualifiers
source                  1..41
                        mol_type = other DNA
                        organism = adeno-associated virus
SEQUENCE: 244
gaaaagcggg caaccagcct gcaagaaaga gattgaattt c                        41

SEQ ID NO: 245          moltype = DNA   length = 41
FEATURE                 Location/Qualifiers
source                  1..41
                        mol_type = other DNA
                        organism = adeno-associated virus
SEQUENCE: 245
gaaaagcggg ccagcagcct gcgagaaaga gattgaattt t                        41

SEQ ID NO: 246          moltype = DNA   length = 41
FEATURE                 Location/Qualifiers
source                  1..41
                        mol_type = other DNA
                        organism = adeno-associated virus
SEQUENCE: 246
gaaaagcggg ccagcagcct gcaagaaaaa gattgaattt c                        41

SEQ ID NO: 247          moltype = DNA   length = 41
FEATURE                 Location/Qualifiers
source                  1..41
                        mol_type = other DNA
                        organism = adeno-associated virus
SEQUENCE: 247
```

```
gaaagtcggg caaccagcct gcaagaaaga gattgaattt c                             41

SEQ ID NO: 248          moltype = DNA  length = 41
FEATURE                 Location/Qualifiers
source                  1..41
                        mol_type = other DNA
                        organism = adeno-associated virus
SEQUENCE: 248
gaaaagcggg ccagcagcct gcaagaaaga gattgaattt t                             41

SEQ ID NO: 249          moltype = DNA  length = 41
FEATURE                 Location/Qualifiers
source                  1..41
                        mol_type = other DNA
                        organism = adeno-associated virus
SEQUENCE: 249
gaaaagcggg caaccagcct gcaagaaaaa gattgaattt t                             41

SEQ ID NO: 250          moltype = DNA  length = 41
FEATURE                 Location/Qualifiers
source                  1..41
                        mol_type = other DNA
                        organism = adeno-associated virus
SEQUENCE: 250
gaaaagcggg ccagcagcct gcgagaaaaa gattgaattt t                             41

SEQ ID NO: 251          moltype = DNA  length = 41
FEATURE                 Location/Qualifiers
source                  1..41
                        mol_type = other DNA
                        organism = adeno-associated virus
SEQUENCE: 251
gaaaagcggg ccagcagcct gcaagaaaaa gattgaattt t                             41

SEQ ID NO: 252          moltype = DNA  length = 41
FEATURE                 Location/Qualifiers
source                  1..41
                        mol_type = other DNA
                        organism = adeno-associated virus
SEQUENCE: 252
gaaaagcggg ccagcagcct gcaagaaaaa gattaaattt t                             41

SEQ ID NO: 253          moltype = DNA  length = 41
FEATURE                 Location/Qualifiers
source                  1..41
                        mol_type = other DNA
                        organism = adeno-associated virus
SEQUENCE: 253
gaaaagcggg ccagcggcct gcaagaaaaa gattaaattt t                             41

SEQ ID NO: 254          moltype = DNA  length = 41
FEATURE                 Location/Qualifiers
source                  1..41
                        mol_type = other DNA
                        organism = adeno-associated virus
SEQUENCE: 254
gaaaagcggg ccatcagcct gcgagaaaga gattgaattt t                             41

SEQ ID NO: 255          moltype = DNA  length = 41
FEATURE                 Location/Qualifiers
source                  1..41
                        mol_type = other DNA
                        organism = adeno-associated virus
SEQUENCE: 255
gaaaggcggg ccatcagcct gcgagaaaga gattgaattt t                             41

SEQ ID NO: 256          moltype = DNA  length = 41
FEATURE                 Location/Qualifiers
source                  1..41
                        mol_type = other DNA
                        organism = adeno-associated virus
SEQUENCE: 256
gaaaagcggg ccagcagcct gcaagaaaaa gactgaattt c                             41

SEQ ID NO: 257          moltype = DNA  length = 41
FEATURE                 Location/Qualifiers
source                  1..41
                        mol_type = other DNA
                        organism = adeno-associated virus
```

```
SEQUENCE: 257
gcaaatcggg caaacagcct gccagaaaaa gactaaattt c                  41

SEQ ID NO: 258          moltype = DNA   length = 41
FEATURE                 Location/Qualifiers
source                  1..41
                        mol_type = other DNA
                        organism = adeno-associated virus
SEQUENCE: 258
gcaaatcagg ccagcagccc gctagaaaaa gactgaattt t                  41

SEQ ID NO: 259          moltype = DNA   length = 41
FEATURE                 Location/Qualifiers
source                  1..41
                        mol_type = other DNA
                        organism = adeno-associated virus
SEQUENCE: 259
gcaaatcagg ccagcagccc gctaagaaaa gactcaattt t                  41

SEQ ID NO: 260          moltype = DNA   length = 41
FEATURE                 Location/Qualifiers
source                  1..41
                        mol_type = other DNA
                        organism = adeno-associated virus
SEQUENCE: 260
gcaaatcggg tgcacagccc gctaaaaaga gactcaattt c                  41

SEQ ID NO: 261          moltype = DNA   length = 41
FEATURE                 Location/Qualifiers
source                  1..41
                        mol_type = other DNA
                        organism = adeno-associated virus
SEQUENCE: 261
gcaaatcggg ttcacagccc gctaaaaaga aactcaattt c                  41

SEQ ID NO: 262          moltype = DNA   length = 41
FEATURE                 Location/Qualifiers
source                  1..41
                        mol_type = other DNA
                        organism = adeno-associated virus
SEQUENCE: 262
gcaaaaaagg caaacaacca gccaaaaaga gactcaactt t                  41

SEQ ID NO: 263          moltype = DNA   length = 41
FEATURE                 Location/Qualifiers
source                  1..41
                        mol_type = other DNA
                        organism = adeno-associated virus
SEQUENCE: 263
gcaaaaaagg caaacaacca gccagaaaga ggctcaactt t                  41

SEQ ID NO: 264          moltype = DNA   length = 60
FEATURE                 Location/Qualifiers
source                  1..60
                        mol_type = other DNA
                        organism = adeno-associated virus
SEQUENCE: 264
gccaagaaaa agcaaaaaga cggcgaacca gccgactctg ctagaaggac actcgacttt  60

SEQ ID NO: 265          moltype = DNA   length = 41
FEATURE                 Location/Qualifiers
source                  1..41
                        mol_type = other DNA
                        organism = adeno-associated virus
SEQUENCE: 265
gcaaaaaagg caagcagccg gctaaaaaga agctcgtttt c                  41

SEQ ID NO: 266          moltype = DNA   length = 41
FEATURE                 Location/Qualifiers
source                  1..41
                        mol_type = other DNA
                        organism = adeno-associated virus
SEQUENCE: 266
gcaagaaagg caaacagcct gccagaaaga gactcaactt t                  41

SEQ ID NO: 267          moltype = DNA   length = 38
FEATURE                 Location/Qualifiers
source                  1..38
                        mol_type = other DNA
```

```
                           organism = adeno-associated virus
SEQUENCE: 267
ccaagaaaaa caagaagcct cgcaaggaaa gaccttcc                              38

SEQ ID NO: 268           moltype = DNA  length = 27
FEATURE                  Location/Qualifiers
source                   1..27
                         mol_type = other DNA
                         organism = adeno-associated virus
SEQUENCE: 268
aagaggactc caagccttcc acctcgt                                          27

SEQ ID NO: 269           moltype = DNA  length = 26
FEATURE                  Location/Qualifiers
source                   1..26
                         mol_type = other DNA
                         organism = adeno-associated virus
SEQUENCE: 269
aagaggactc caagccttcc actcgt                                           26

SEQ ID NO: 270           moltype = DNA  length = 35
FEATURE                  Location/Qualifiers
source                   1..35
                         mol_type = other DNA
                         organism = adeno-associated virus
SEQUENCE: 270
ttaagaagcc taaacctacc gaggaagtca gtgcg                                 35

SEQ ID NO: 271           moltype = DNA  length = 55
FEATURE                  Location/Qualifiers
source                   1..55
                         mol_type = other DNA
                         organism = adeno-associated virus
SEQUENCE: 271
tgtttactct gagcctcgcc ccattggcac tcgttacctc acccgtaatc tgtaa           55

SEQ ID NO: 272           moltype = DNA  length = 55
FEATURE                  Location/Qualifiers
source                   1..55
                         mol_type = other DNA
                         organism = adeno-associated virus
SEQUENCE: 272
tgtttactct gagcctcgcc ccattggcac tcgttacccc acccgtaatc tgtaa           55

SEQ ID NO: 273           moltype = DNA  length = 55
FEATURE                  Location/Qualifiers
source                   1..55
                         mol_type = other DNA
                         organism = adeno-associated virus
SEQUENCE: 273
tgtttactct gagcctcgcc ctattggcac tcgttacctc acccgtaatc tgtaa           55

SEQ ID NO: 274           moltype = DNA  length = 54
FEATURE                  Location/Qualifiers
source                   1..54
                         mol_type = other DNA
                         organism = adeno-associated virus
SEQUENCE: 274
tgtttattct gagcctcgcc cattggtact cgttacctca cccgtaatct gtaa            54

SEQ ID NO: 275           moltype = DNA  length = 55
FEATURE                  Location/Qualifiers
source                   1..55
                         mol_type = other DNA
                         organism = adeno-associated virus
SEQUENCE: 275
aacttattct gagcctcgcc ccattggtac tcgctacctc acccgtaatc tgtaa           55

SEQ ID NO: 276           moltype = DNA  length = 55
FEATURE                  Location/Qualifiers
source                   1..55
                         mol_type = other DNA
                         organism = adeno-associated virus
SEQUENCE: 276
aacttattct gagcctcgcc ccattggtac tcgttacctc acccgtaatc tgtaa           55

SEQ ID NO: 277           moltype = DNA  length = 55
FEATURE                  Location/Qualifiers
source                   1..55
```

```
                        mol_type = other DNA
                        organism = adeno-associated virus
SEQUENCE: 277
tacatattca gagcctcgcc ccattggtac tcgttatctg acacgtaatc tgtaa         55

SEQ ID NO: 278          moltype = DNA  length = 55
FEATURE                 Location/Qualifiers
source                  1..55
                        mol_type = other DNA
                        organism = adeno-associated virus
SEQUENCE: 278
aacttattct gagcctcgcc ccattggtac tcgttatctg acacgtaatc tgtaa         55

SEQ ID NO: 279          moltype = DNA  length = 55
FEATURE                 Location/Qualifiers
source                  1..55
                        mol_type = other DNA
                        organism = adeno-associated virus
SEQUENCE: 279
tacttattca gagcctcgcc ccattggcac tcgttatctc accgtaatc tgtaa          55

SEQ ID NO: 280          moltype = DNA  length = 55
FEATURE                 Location/Qualifiers
source                  1..55
                        mol_type = other DNA
                        organism = adeno-associated virus
SEQUENCE: 280
tacttattca ccattggcac ccgttacctc accgtaacc tgtaa                     55

SEQ ID NO: 281          moltype = DNA  length = 54
FEATURE                 Location/Qualifiers
source                  1..54
                        mol_type = other DNA
                        organism = adeno-associated virus
SEQUENCE: 281
tgtgtattca gagcctcgcc cattggcacc agatacctga ctcgtaatct gtaa          54

SEQ ID NO: 282          moltype = DNA  length = 55
FEATURE                 Location/Qualifiers
source                  1..55
                        mol_type = other DNA
                        organism = adeno-associated virus
SEQUENCE: 282
tacttattca gagcctcgcc ccattggcac ccgttacctc accgtagcc tgtaa          55

SEQ ID NO: 283          moltype = DNA  length = 55
FEATURE                 Location/Qualifiers
source                  1..55
                        mol_type = other DNA
                        organism = adeno-associated virus
SEQUENCE: 283
cacttattct gagcctcgcc ccatcggcac ccgttacctc accgtaatc tgtaa          55

SEQ ID NO: 284          moltype = DNA  length = 55
FEATURE                 Location/Qualifiers
source                  1..55
                        mol_type = other DNA
                        organism = adeno-associated virus
SEQUENCE: 284
tgtatatagc gaaccccgcc ccattggcac tcgttacctc accgtaatc tgtaa          55

SEQ ID NO: 285          moltype = DNA  length = 55
FEATURE                 Location/Qualifiers
source                  1..55
                        mol_type = other DNA
                        organism = adeno-associated virus
SEQUENCE: 285
tgtatatagt gaaccccgcc ccattggcac tcgttacctc accgtaatc tgtaa          55

SEQ ID NO: 286          moltype = DNA  length = 55
FEATURE                 Location/Qualifiers
source                  1..55
                        mol_type = other DNA
                        organism = adeno-associated virus
SEQUENCE: 286
cgtgtactct gaaccccgcc ccattggcac ccgttacctc accgtaatc tgtaa          55

SEQ ID NO: 287          moltype = DNA  length = 55
FEATURE                 Location/Qualifiers
```

```
source                  1..55
                        mol_type = other DNA
                        organism = adeno-associated virus
SEQUENCE: 287
tgtttactct gagcctcgcc ccattggtac tcgttacctc acccgtaatt tgtaa          55

SEQ ID NO: 288          moltype = DNA   length = 55
FEATURE                 Location/Qualifiers
source                  1..55
                        mol_type = other DNA
                        organism = adeno-associated virus
SEQUENCE: 288
ggtttatagc gagcctcgcc ccattggcac ccgttacctc acccgcaacc tgtaa          55

SEQ ID NO: 289          moltype = DNA   length = 55
FEATURE                 Location/Qualifiers
source                  1..55
                        mol_type = other DNA
                        organism = adeno-associated virus
SEQUENCE: 289
ggtttatact gagcctcgcc ccattggcac ccgttacctc acccgtaacc tgtaa          55

SEQ ID NO: 290          moltype = DNA   length = 55
FEATURE                 Location/Qualifiers
source                  1..55
                        mol_type = other DNA
                        organism = adeno-associated virus
SEQUENCE: 290
tgtttatact gagcctcgcc ccattggcac tcgttacctc acccgtaatc tgtaa          55

SEQ ID NO: 291          moltype = DNA   length = 55
FEATURE                 Location/Qualifiers
source                  1..55
                        mol_type = other DNA
                        organism = adeno-associated virus
SEQUENCE: 291
tgtttatact gagcctcgcc ccattggcac tcgttacctc ccccgtaatc tgtaa          55

SEQ ID NO: 292          moltype = DNA   length = 55
FEATURE                 Location/Qualifiers
source                  1..55
                        mol_type = other DNA
                        organism = adeno-associated virus
SEQUENCE: 292
actttatact gagcctcgcc ccattggcac ccgttacctt acccgtcccc tgtaa          55

SEQ ID NO: 293          moltype = DNA   length = 55
FEATURE                 Location/Qualifiers
source                  1..55
                        mol_type = other DNA
                        organism = adeno-associated virus
SEQUENCE: 293
actttatact gagcctcgcc ccattggcac ccgttacctc acccgtcccc tgtaa          55

SEQ ID NO: 294          moltype = DNA   length = 55
FEATURE                 Location/Qualifiers
source                  1..55
                        mol_type = other DNA
                        organism = adeno-associated virus
SEQUENCE: 294
cgtgtattca gagcctcgcc ccattggcac cagatacctg actcgtaatc tgtaa          55

SEQ ID NO: 295          moltype = DNA   length = 55
FEATURE                 Location/Qualifiers
source                  1..55
                        mol_type = other DNA
                        organism = adeno-associated virus
SEQUENCE: 295
cgtgtattca gagcctcgcc ccattggcac cagatacctg actcgtaatt tgtaa          55

SEQ ID NO: 296          moltype = DNA   length = 55
FEATURE                 Location/Qualifiers
source                  1..55
                        mol_type = other DNA
                        organism = adeno-associated virus
SEQUENCE: 296
ggtgtattca gagcctcgcc ctattggcac cagatacctg actcgtaatc tgtaa          55

SEQ ID NO: 297          moltype = DNA   length = 55
```

```
FEATURE                 Location/Qualifiers
source                  1..55
                        mol_type = other DNA
                        organism = adeno-associated virus
SEQUENCE: 297
tgtgtattca gagcctcgcc ccattggcac caggtacctg actcgtaatc tgtaa         55

SEQ ID NO: 298          moltype = DNA   length = 55
FEATURE                 Location/Qualifiers
source                  1..55
                        mol_type = other DNA
                        organism = adeno-associated virus
SEQUENCE: 298
tgtgtattca gagcctcgcc ccattggcac cagatacctg actcgtaatc tgtaa         55

SEQ ID NO: 299          moltype = DNA   length = 55
FEATURE                 Location/Qualifiers
source                  1..55
                        mol_type = other DNA
                        organism = adeno-associated virus
SEQUENCE: 299
tgtgtattca gagcctcgcc ccattggcgc cagatacctg actcgtaatc tgtaa         55

SEQ ID NO: 300          moltype = DNA   length = 55
FEATURE                 Location/Qualifiers
source                  1..55
                        mol_type = other DNA
                        organism = adeno-associated virus
SEQUENCE: 300
tgtgtattca gagcctcgcc ccattggcac cagatacccg actcgtaatc tgtaa         55

SEQ ID NO: 301          moltype = DNA   length = 55
FEATURE                 Location/Qualifiers
source                  1..55
                        mol_type = other DNA
                        organism = adeno-associated virus
SEQUENCE: 301
tgtgtattca gagcctcgcc ccattggcac cacatacctg actcgtaatc tgtaa         55

SEQ ID NO: 302          moltype = DNA   length = 55
FEATURE                 Location/Qualifiers
source                  1..55
                        mol_type = other DNA
                        organism = adeno-associated virus
SEQUENCE: 302
cgtgtactca gagcctcgcc ccattggcac cagatacctg actcgtaatc tgtaa         55

SEQ ID NO: 303          moltype = DNA   length = 56
FEATURE                 Location/Qualifiers
source                  1..56
                        mol_type = other DNA
                        organism = adeno-associated virus
SEQUENCE: 303
tgtgtattca gagcctcgcc ccattggcac cagatacctg actcgtaatc tgtaat        56

SEQ ID NO: 304          moltype = DNA   length = 55
FEATURE                 Location/Qualifiers
source                  1..55
                        mol_type = other DNA
                        organism = adeno-associated virus
SEQUENCE: 304
tgtgtattca gagccttgcc ccattggcac cagatacctg actcgtaatc tgtaa         55

SEQ ID NO: 305          moltype = DNA   length = 55
FEATURE                 Location/Qualifiers
source                  1..55
                        mol_type = other DNA
                        organism = adeno-associated virus
SEQUENCE: 305
tgtttatagt gaacctcgcc ctattggaac ccggtatctc acacgaaact tgtga         55

SEQ ID NO: 306          moltype = DNA   length = 55
FEATURE                 Location/Qualifiers
source                  1..55
                        mol_type = other DNA
                        organism = adeno-associated virus
SEQUENCE: 306
tgtttatagt gaacctcgcc ctattggaac ccggtatctc acacgaaact tgtaa         55
```

-continued

```
SEQ ID NO: 307             moltype = DNA   length = 55
FEATURE                    Location/Qualifiers
source                     1..55
                           mol_type = other DNA
                           organism = adeno-associated virus
SEQUENCE: 307
tgtttattct gaacccgcc ctattggcac tcgttacctt acccggaact tgtaa          55

SEQ ID NO: 308             moltype = DNA   length = 55
FEATURE                    Location/Qualifiers
source                     1..55
                           mol_type = other DNA
                           organism = adeno-associated virus
SEQUENCE: 308
tgtatatagt gaacccgcc ccattggcac cagatacctg actcgtaatc tgtaa          55

SEQ ID NO: 309             moltype = DNA   length = 55
FEATURE                    Location/Qualifiers
source                     1..55
                           mol_type = other DNA
                           organism = adeno-associated virus
SEQUENCE: 309
gaagtataca gagccgcggg ttattggctc tcgttatttg actaatcatt tgtaa          55

SEQ ID NO: 310             moltype = DNA   length = 55
FEATURE                    Location/Qualifiers
source                     1..55
                           mol_type = other DNA
                           organism = adeno-associated virus
SEQUENCE: 310
caactaccac gaactccggg ctattgggtc ccgtttcctc acccaccact tgtaa          55

SEQ ID NO: 311             moltype = DNA   length = 55
FEATURE                    Location/Qualifiers
source                     1..55
                           mol_type = other DNA
                           organism = adeno-associated virus
SEQUENCE: 311
gaaatacact gagcctaggg ctatcggtac ccgctacctc acccaccacc tgtaa          55

SEQ ID NO: 312             moltype = DNA   length = 55
FEATURE                    Location/Qualifiers
source                     1..55
                           mol_type = other DNA
                           organism = adeno-associated virus
SEQUENCE: 312
agcctacaaa gagcccaggg ccattggatc ccgatacctc accaaccacc tctag          55

SEQ ID NO: 313             moltype = DNA   length = 55
FEATURE                    Location/Qualifiers
source                     1..55
                           mol_type = other DNA
                           organism = adeno-associated virus
SEQUENCE: 313
atcctattcc gaacctcgtc ccatcggtac ccgttacctt accaaacctc tgtaa          55

SEQ ID NO: 314             moltype = DNA   length = 55
FEATURE                    Location/Qualifiers
source                     1..55
                           mol_type = other DNA
                           organism = adeno-associated virus
SEQUENCE: 314
ggaatacaga accaccagac ctatcggaac ccgatacctt acccgacccc tttaa          55

SEQ ID NO: 315             moltype = DNA   length = 55
FEATURE                    Location/Qualifiers
source                     1..55
                           mol_type = other DNA
                           organism = adeno-associated virus
SEQUENCE: 315
cgaatacaga accaccagag ccatcggaac ccgatacctc acccgacccc tttaa          55

SEQ ID NO: 316             moltype = DNA   length = 55
FEATURE                    Location/Qualifiers
source                     1..55
                           mol_type = other DNA
                           organism = adeno-associated virus
SEQUENCE: 316
tggatatgta gaagatagat tgattggaac cagatatcta actcaaaatc tgtaa          55
```

```
SEQ ID NO: 317           moltype = DNA  length = 106
FEATURE                  Location/Qualifiers
source                   1..106
                         mol_type = other DNA
                         organism = adeno-associated virus
SEQUENCE: 317
ctcgaacctc tcggtctggt tgaggaaggc gctaagacgg ctcctggaaa gaagagaccg    60
gtagagccgt caccacagcg ttcccccgac tcctccacgg gcatcg                 106

SEQ ID NO: 318           moltype = DNA  length = 105
FEATURE                  Location/Qualifiers
source                   1..105
                         mol_type = other DNA
                         organism = adeno-associated virus
SEQUENCE: 318
ctcgaacctc tcggtctggt tgaggaagct gctaagacgg ctcctggaaa gaagagaccg    60
gtagaccgtc acctcagcgt tcccccgact cctcacggg catcg                   105

SEQ ID NO: 319           moltype = DNA  length = 106
FEATURE                  Location/Qualifiers
source                   1..106
                         mol_type = other DNA
                         organism = adeno-associated virus
SEQUENCE: 319
ctcgaacctc tcggtctggt tgaggaaggc gctaagacgg ctcctgcaaa gaagagaccg    60
gtagagccgt cacctcagcg ttcccccgac tcctccacgg gcatcg                 106

SEQ ID NO: 320           moltype = DNA  length = 106
FEATURE                  Location/Qualifiers
source                   1..106
                         mol_type = other DNA
                         organism = adeno-associated virus
SEQUENCE: 320
ctcgaacctc tcggtctggc tgaggaagct gctaagacgg ctcctggaaa gaagagaccg    60
gtagaaccgt cacctcagcg ttcccccgac tcctccacgg gcatcg                 106

SEQ ID NO: 321           moltype = DNA  length = 106
FEATURE                  Location/Qualifiers
source                   1..106
                         mol_type = other DNA
                         organism = adeno-associated virus
SEQUENCE: 321
ctcgaacctc tcggtctggt tgaggaagct gctaagacgg ctcctggaaa gaagagaccg    60
gtagaaccgt cacctcagcg ttcccccgac tcctccacgg gcatcg                 106

SEQ ID NO: 322           moltype = DNA  length = 107
FEATURE                  Location/Qualifiers
source                   1..107
                         mol_type = other DNA
                         organism = adeno-associated virus
SEQUENCE: 322
ctcgaacctc tcggtctggt tgaggaagct gctaagacgg ctcctggaaa gaagagaccg    60
gtagaaccgt cacctcagcg ttcccccgac tcctcccacg ggcatcg                107

SEQ ID NO: 323           moltype = DNA  length = 106
FEATURE                  Location/Qualifiers
source                   1..106
                         mol_type = other DNA
                         organism = adeno-associated virus
SEQUENCE: 323
ctcgaacctc tcggtccggt tgaggaagct gctaagacgg ctcctggaaa gaagagaccg    60
gtagaaccgc cacctcagcg ttcccccgac tcctccacgg gcatcg                 106

SEQ ID NO: 324           moltype = DNA  length = 106
FEATURE                  Location/Qualifiers
source                   1..106
                         mol_type = other DNA
                         organism = adeno-associated virus
SEQUENCE: 324
ctcgaacctc tcggtctggt tgaggaagct gctaagacgg ctcctggaaa gaagagaccg    60
gtagaaccgt cacctcagcg ttcccccgac tcctccgcgg gcatcg                 106

SEQ ID NO: 325           moltype = DNA  length = 106
FEATURE                  Location/Qualifiers
source                   1..106
                         mol_type = other DNA
                         organism = adeno-associated virus
SEQUENCE: 325
```

```
ctcgaacctc tcggtctggt tgaggaagcg gctaagacgg ctcctggaaa gaagagaccg    60
gtagaaccgt cacctcagcg ttcccccgac tcctccacgg gcatcg                  106

SEQ ID NO: 326          moltype = DNA   length = 106
FEATURE                 Location/Qualifiers
source                  1..106
                        mol_type = other DNA
                        organism = adeno-associated virus
SEQUENCE: 326
ctcgaacctc tcggtctggt tgaggaaggc gctaagacgg ctcctggaaa gaagagaccg    60
gtagagccat cacctcagcg ttcccccgac tcctccacgg gcatcg                  106

SEQ ID NO: 327          moltype = DNA   length = 106
FEATURE                 Location/Qualifiers
source                  1..106
                        mol_type = other DNA
                        organism = adeno-associated virus
SEQUENCE: 327
ctcgaacctc tcggtctggt tgaggaaggc gctaagacgg ctcctggaaa gaagagaccg    60
gtagagccat caccccagcg ttctccagac tcctctacgg gcatcg                  106

SEQ ID NO: 328          moltype = DNA   length = 91
FEATURE                 Location/Qualifiers
source                  1..91
                        mol_type = other DNA
                        organism = adeno-associated virus
SEQUENCE: 328
ctcgaacctc tcggtctggt tgaggaaggc gctaagacgg ctcctggaaa gaagagaccc    60
atagaatccc ccgactcctc cacgggcatc g                                   91

SEQ ID NO: 329          moltype = DNA   length = 106
FEATURE                 Location/Qualifiers
source                  1..106
                        mol_type = other DNA
                        organism = adeno-associated virus
SEQUENCE: 329
ctcgaacctc tcggtctggt tgaggaaggc gctaagacgg ctcctggaaa gaagagaccg    60
gtagagccat caccccagcg ttctccagac tccactacgg gcatcg                  106

SEQ ID NO: 330          moltype = DNA   length = 88
FEATURE                 Location/Qualifiers
source                  1..88
                        mol_type = other DNA
                        organism = adeno-associated virus
SEQUENCE: 330
ctcgagcctc tgggtctggt tgaggaaggc gctaagacgg ctcctggaaa gaagcggcca    60
gtagaaccgg actccagctc gggcatcg                                       88

SEQ ID NO: 331          moltype = DNA   length = 103
FEATURE                 Location/Qualifiers
source                  1..103
                        mol_type = other DNA
                        organism = adeno-associated virus
SEQUENCE: 331
ctcgaacctc tcggtctggt tgaggaaggc gctaagacgg ctcctggaaa gaagagacca    60
gtagagcagt caccccaaga accagactcc tcctcgggca tcg                     103

SEQ ID NO: 332          moltype = DNA   length = 103
FEATURE                 Location/Qualifiers
source                  1..103
                        mol_type = other DNA
                        organism = adeno-associated virus
SEQUENCE: 332
ctcgaacctc tcggtctggt tgaggaaggc gctaagacgg ctcctggaaa gaagagaccg    60
gtagagcagt cgccacaaga gccagactcc tcctcgggca tcg                     103

SEQ ID NO: 333          moltype = DNA   length = 91
FEATURE                 Location/Qualifiers
source                  1..91
                        mol_type = other DNA
                        organism = adeno-associated virus
SEQUENCE: 333
ctcgaacctc tcggtctggt tgaggaagtc gctaagacgg ctcctggaaa gaagagaccc    60
atagaatccc ccgactcctc cacgggcatc g                                   91

SEQ ID NO: 334          moltype = DNA   length = 91
FEATURE                 Location/Qualifiers
source                  1..91
                        mol_type = other DNA
```

-continued

```
                         organism = adeno-associated virus
SEQUENCE: 334
ctcgaacctc tcggtctggt tgaggaaggc gctaagacgg cttccggaaa gaagagaccc     60
atagaatccc ccgactcctc cacgggcatc g                                   91

SEQ ID NO: 335           moltype = DNA   length = 91
FEATURE                  Location/Qualifiers
source                   1..91
                         mol_type = other DNA
                         organism = adeno-associated virus
SEQUENCE: 335
ctcgaacctc tcggtctggt tgaggaaggc gctaagacgg ctcctggaaa gaagagaccc     60
ataggctctc cagactcctc cacgggcatc g                                   91

SEQ ID NO: 336           moltype = DNA   length = 91
FEATURE                  Location/Qualifiers
source                   1..91
                         mol_type = other DNA
                         organism = adeno-associated virus
SEQUENCE: 336
ctcgaacctc tcggtctggt tgaggaaggc gctaagacgg ctcctggaaa gaagagaccc     60
atagactctc cagactcctc cacgggcatc g                                   91

SEQ ID NO: 337           moltype = DNA   length = 103
FEATURE                  Location/Qualifiers
source                   1..103
                         mol_type = other DNA
                         organism = adeno-associated virus
SEQUENCE: 337
ctcgaacctc tcggtctggt tgaggaaggc gctaagacgg ctcctggaaa gaaacgtccg     60
gtagagcagt cgccacaaga gccagactcc tcctcgggca tcg                      103

SEQ ID NO: 338           moltype = DNA   length = 103
FEATURE                  Location/Qualifiers
source                   1..103
                         mol_type = other DNA
                         organism = adeno-associated virus
SEQUENCE: 338
ctcgaacctc tcggtctggt tgaggaaggc gctaagacgg ctcctccaaa gaaacgtccg     60
gtagagcagt cgccacaaga gccagactcc ccctcgggca tcg                      103

SEQ ID NO: 339           moltype = DNA   length = 103
FEATURE                  Location/Qualifiers
source                   1..103
                         mol_type = other DNA
                         organism = adeno-associated virus
SEQUENCE: 339
ctcgaacctc tcggtctggt tgaggaaggc gctgagacgg ctcctggaaa gaaacgtccg     60
gtagagcagt cgccacaagg gccagactcc tcctcgggca tcg                      103

SEQ ID NO: 340           moltype = DNA   length = 103
FEATURE                  Location/Qualifiers
source                   1..103
                         mol_type = other DNA
                         organism = adeno-associated virus
SEQUENCE: 340
ctcgaacctt ttggtctggt tgaggaaggt gctaagacgg ctcctggaaa gaaacgtccg     60
gtagagcagt cgccacaaga gccagactcc tcctcgggca ttg                      103

SEQ ID NO: 341           moltype = DNA   length = 103
FEATURE                  Location/Qualifiers
source                   1..103
                         mol_type = other DNA
                         organism = adeno-associated virus
SEQUENCE: 341
cttgaacctc tgggcctggt tgaggaacct gttaagacgg ctccgggaaa aaagaggccg     60
gtagagcact ctcctgtcca gccagactcc tcctcgggaa ccg                      103

SEQ ID NO: 342           moltype = DNA   length = 103
FEATURE                  Location/Qualifiers
source                   1..103
                         mol_type = other DNA
                         organism = adeno-associated virus
SEQUENCE: 342
cttgaacctc tgggcctggt tggggaacct gttaagacgg ctccgggaaa aaagaggccg     60
gtagagcact ctcctgtgga gccagactcc tcctcgggaa ccg                      103

SEQ ID NO: 343           moltype = DNA   length = 102
FEATURE                  Location/Qualifiers
```

```
                         1..102
                         mol_type = other DNA
                         organism = adeno-associated virus
SEQUENCE: 343
cttgaacctc tgggcctggt tggggaacct gtcaagacgg ctccaggaaa aagaggccgg    60
tagagcactc tcctgtggag ccagactcct cctcgggaac cg                      102

SEQ ID NO: 344           moltype = DNA   length = 103
FEATURE                  Location/Qualifiers
source                   1..103
                         mol_type = other DNA
                         organism = adeno-associated virus
SEQUENCE: 344
cttgaacctc tgggcctggt tgaggaacct gttaagacgg ctccgggaaa aagaggccg     60
gtagagcact ctcctgcgga gccagactcc tcctcgggaa ccg                     103

SEQ ID NO: 345           moltype = DNA   length = 103
FEATURE                  Location/Qualifiers
source                   1..103
                         mol_type = other DNA
                         organism = adeno-associated virus
SEQUENCE: 345
cttgaacctc tgggcctggt tgaggaacct gttaagacgg ctccgggaaa aagaggccg     60
gtagagcact ctcttgcgga gccagactcc tcctcgggaa ccg                     103

SEQ ID NO: 346           moltype = DNA   length = 103
FEATURE                  Location/Qualifiers
source                   1..103
                         mol_type = other DNA
                         organism = adeno-associated virus
SEQUENCE: 346
cttgaacctc tgggcctggt tgaggagcct gttaagacgg ctccgggaaa aagaggccg     60
gtagagcact ctcctgtgga gccagactcc tcctcgggaa ccg                     103

SEQ ID NO: 347           moltype = DNA   length = 103
FEATURE                  Location/Qualifiers
source                   1..103
                         mol_type = other DNA
                         organism = adeno-associated virus
SEQUENCE: 347
cttgaacctc tgggcctggt tgaggaacct gttaagacgg ctccgggaaa aagaggccg     60
gtagagcact ctcctgtgga gccagactcc tcctcgggaa cag                     103

SEQ ID NO: 348           moltype = DNA   length = 103
FEATURE                  Location/Qualifiers
source                   1..103
                         mol_type = other DNA
                         organism = adeno-associated virus
SEQUENCE: 348
cttgaacctc tgggcctggt tgaggagcct gttaaaacgg ctccgggaaa aagaggccg     60
gtagagcact ctcctgcgga gccagactcc tcctcgggaa ccg                     103

SEQ ID NO: 349           moltype = DNA   length = 103
FEATURE                  Location/Qualifiers
source                   1..103
                         mol_type = other DNA
                         organism = adeno-associated virus
SEQUENCE: 349
ctggaacctc tgggcctggt tgaggagcct gttaagacgg ctccgggaaa aagaggccg     60
gtagagcact ctcctgcaga gccagattcc tcctccggaa ctg                     103

SEQ ID NO: 350           moltype = DNA   length = 103
FEATURE                  Location/Qualifiers
source                   1..103
                         mol_type = other DNA
                         organism = adeno-associated virus
SEQUENCE: 350
ctggaacctc tgagcctggt tgaggagcct gttaagacgg ctccgggaaa aagaggccg     60
gtagagcact ctcccgcaga gccagattcc tcctccggaa ctg                     103

SEQ ID NO: 351           moltype = DNA   length = 103
FEATURE                  Location/Qualifiers
source                   1..103
                         mol_type = other DNA
                         organism = adeno-associated virus
SEQUENCE: 351
cttgaacctc tgggcctggt tgaggaacct gttaaggcgg ctccgggaga aagaggccg     60
gtagagcact ctcctgcgga gccagactcc tcctcgggaa ccg                     103
```

```
SEQ ID NO: 352           moltype = DNA   length = 103
FEATURE                  Location/Qualifiers
source                   1..103
                         mol_type = other DNA
                         organism = adeno-associated virus
SEQUENCE: 352
cttgaacctc tgggcctggt tgaggaacct gttaagacgg ctccgggaga aaagaggccg    60
gtagagcact ctcctgcgga gccagactcc tcctcgggaa ccg                    103

SEQ ID NO: 353           moltype = DNA   length = 103
FEATURE                  Location/Qualifiers
source                   1..103
                         mol_type = other DNA
                         organism = adeno-associated virus
SEQUENCE: 353
cttgaacctc tgggcttggt tggggagcct gttaaaacgg ctccgggaaa aaagaggccg    60
gtagagcact ctcctgtgga gccagactcc tcctcgggaa ccg                    103

SEQ ID NO: 354           moltype = DNA   length = 102
FEATURE                  Location/Qualifiers
source                   1..102
                         mol_type = other DNA
                         organism = adeno-associated virus
SEQUENCE: 354
cttgaacctc tgggcttggt tgaggagcct gttaaaacgg ctccgggaaa aaagaggccg    60
gtagagcact ctcctgtgga gccagactcc tcctcggaac cg                     102

SEQ ID NO: 355           moltype = DNA   length = 103
FEATURE                  Location/Qualifiers
source                   1..103
                         mol_type = other DNA
                         organism = adeno-associated virus
SEQUENCE: 355
cttgaacctc tgggcctggt tgaggagcct gttaaaacgg ctccgggaaa aaagaggccg    60
gtagagcact ctcctgtgga gccagactcc tcctcgggaa ccg                    103

SEQ ID NO: 356           moltype = DNA   length = 103
FEATURE                  Location/Qualifiers
source                   1..103
                         mol_type = other DNA
                         organism = adeno-associated virus
SEQUENCE: 356
cttgaacctc tgggcctggt tgagggacct gttaagacgg ctccgggaaa aaagaggccg    60
gtagagcact ctcctgcgga gccagactcc tcctcgggaa ccg                    103

SEQ ID NO: 357           moltype = DNA   length = 103
FEATURE                  Location/Qualifiers
source                   1..103
                         mol_type = other DNA
                         organism = adeno-associated virus
SEQUENCE: 357
cttgaacctc tgggcctggt tgaggaacct gttaaaacgg ctccgggaaa aaagaggccg    60
gtagagcact ctcctgtgga gccagactgg tggtgcccaa ccg                    103

SEQ ID NO: 358           moltype = DNA   length = 103
FEATURE                  Location/Qualifiers
source                   1..103
                         mol_type = other DNA
                         organism = adeno-associated virus
SEQUENCE: 358
cttgaacctc tgggcctggt tgaggagcct gttaaaacgg ctccgggaaa aaagagaccg    60
gtagagcact ctcctgcgga gccagactcc tcctcgggaa ccg                    103

SEQ ID NO: 359           moltype = DNA   length = 103
FEATURE                  Location/Qualifiers
source                   1..103
                         mol_type = other DNA
                         organism = adeno-associated virus
SEQUENCE: 359
cttgaacctc tgggcctggt tgaggaacct gttaagacgg ctccgggaaa aaagaggccg    60
gtagagcact ctcctgtgga gccagactcc tcctcgggaa ccg                    103

SEQ ID NO: 360           moltype = DNA   length = 105
FEATURE                  Location/Qualifiers
source                   1..105
                         mol_type = other DNA
                         organism = adeno-associated virus
SEQUENCE: 360
cttgaacctc tgcggcctgg tttgaggaaa cctgttaaga cggctccggg aaaaaagagg    60
```

```
ccggtagagc actctcctgt tagccagact cctcctcggg aaccg            105

SEQ ID NO: 361          moltype = DNA   length = 103
FEATURE                 Location/Qualifiers
source                  1..103
                        mol_type = other DNA
                        organism = adeno-associated virus
SEQUENCE: 361
cttgaacctc tgggcctggt tgaggaacct gttaaaacgg ctccgggaaa aaagaggccg   60
gtagagcacc ctcctgtgga gccagactcc tcctcgggaa ccg                    103

SEQ ID NO: 362          moltype = DNA   length = 103
FEATURE                 Location/Qualifiers
source                  1..103
                        mol_type = other DNA
                        organism = adeno-associated virus
SEQUENCE: 362
cttgagcctc ttggtctggt tgaggaagca gctaaaacgg ctcctggaaa gaaggggct    60
gtagatcagt ctcctcagga accggactca tcatctggtg ttg                    103

SEQ ID NO: 363          moltype = DNA   length = 103
FEATURE                 Location/Qualifiers
source                  1..103
                        mol_type = other DNA
                        organism = adeno-associated virus
SEQUENCE: 363
cttgagcctc ttggtctggt tgaggaagca gctaaaacgg ctcctggaaa gaagaggcct   60
gtagatcagt ctcctcagga accggactca tcatctggtg ttg                    103

SEQ ID NO: 364          moltype = DNA   length = 103
FEATURE                 Location/Qualifiers
source                  1..103
                        mol_type = other DNA
                        organism = adeno-associated virus
SEQUENCE: 364
cttgagcctc tgggtctggt tgaggaagcg gctaagacgg ctcctggaaa aaagagacct   60
gtagagcaat ctccagcaga accggactcc tcttcgggca tcg                    103

SEQ ID NO: 365          moltype = DNA   length = 103
FEATURE                 Location/Qualifiers
source                  1..103
                        mol_type = other DNA
                        organism = adeno-associated virus
SEQUENCE: 365
ctcgagcctc ttggtctggt tgaggaagct gttaagacgg ctcctggaaa aaagagacct   60
atagagcagt ctcctgcaga accggactct tcctcgggca tcg                    103

SEQ ID NO: 366          moltype = DNA   length = 103
FEATURE                 Location/Qualifiers
source                  1..103
                        mol_type = other DNA
                        organism = adeno-associated virus
SEQUENCE: 366
cttgaacctc ttggtctggt tgaggaagcg gctaagacgg ctcctggaaa gaagaggcct   60
gtagagcagt ctcctcagga accggactcc tccgcgggta ttg                    103

SEQ ID NO: 367          moltype = DNA   length = 100
FEATURE                 Location/Qualifiers
source                  1..100
                        mol_type = other DNA
                        organism = adeno-associated virus
SEQUENCE: 367
ctcgaacctc tgggcctggt tgaagaaggt gctaagacgg ctcctggaaa gaagagaccg   60
ttagagtcac cacaagagcc cgactcctcc tcaggaatcg                        100

SEQ ID NO: 368          moltype = DNA   length = 100
FEATURE                 Location/Qualifiers
source                  1..100
                        mol_type = other DNA
                        organism = adeno-associated virus
SEQUENCE: 368
ctcgaaccac tgggcctggt tgaagaaggt gctaagacgg ctcctggaaa gaagagaccg   60
ttagagtcac cacaagagcc cgactcctcc tcaggaatcg                        100

SEQ ID NO: 369          moltype = DNA   length = 100
FEATURE                 Location/Qualifiers
source                  1..100
                        mol_type = other DNA
                        organism = adeno-associated virus
```

```
SEQUENCE: 369
ctcgaacctc tgggcctggt tgaagaaggt gctaaaacgg ctcctggaaa gaagagaccg    60
ttagagtcac cacaagagcc cgactcctcc tcgggcatcg                          100

SEQ ID NO: 370          moltype = DNA   length = 111
FEATURE                 Location/Qualifiers
source                  1..111
                        mol_type = other DNA
                        organism = adeno-associated virus
SEQUENCE: 370
ctcgagcctc tgggtctggt tgaagagggc gttaaaacgg ctcctggaaa gaaacgccca    60
ttagaaaaga ctccaaatcg gccgaccaac ccggactctg ggaaggcccc g             111

SEQ ID NO: 371          moltype = DNA   length = 102
FEATURE                 Location/Qualifiers
source                  1..102
                        mol_type = other DNA
                        organism = adeno-associated virus
SEQUENCE: 371
cttgaacctc ttggtctggt tgagcaagcg ggtgagacgg ctcctggaaa gaagagaccg    60
ttgattgatc cccccagcag cccgactcct ccacgggtat cg                       102

SEQ ID NO: 372          moltype = DNA   length = 106
FEATURE                 Location/Qualifiers
source                  1..106
                        mol_type = other DNA
                        organism = adeno-associated virus
SEQUENCE: 372
ctcgaacctc ttggcctggt tgagacgccg gataaaacgg cgcctgcggc aaaaaagagg    60
cctctagagc agagtcctca agagccagac tcctcgagcg gagttg                   106

SEQ ID NO: 373          moltype = DNA   length = 103
FEATURE                 Location/Qualifiers
source                  1..103
                        mol_type = other DNA
                        organism = adeno-associated virus
SEQUENCE: 373
ctcgaaccct ttggtctggt ggaagactca aagacggctc cgaccggaga caagcggaaa    60
ggcgaagacg aacctcgttt gcccgacact tcttcacaga ctc                      103

SEQ ID NO: 374          moltype = DNA   length = 97
FEATURE                 Location/Qualifiers
source                  1..97
                        mol_type = other DNA
                        organism = adeno-associated virus
SEQUENCE: 374
ctcgaaccTT ttggcctggt tgaagagggt gctaagacgg cccctaccgg aaagcggata    60
gacgaccact ttccaaaaag aaagaaggct cggaccg                             97

SEQ ID NO: 375          moltype = DNA   length = 88
FEATURE                 Location/Qualifiers
source                  1..88
                        mol_type = other DNA
                        organism = adeno-associated virus
SEQUENCE: 375
ttagagccat ttggcctagt agaagatcct gtcaacacgg cacctgcaaa aaaaaataca    60
gggaagctta ctgaccatta cccggtag                                       88

SEQ ID NO: 376          moltype = DNA   length = 57
FEATURE                 Location/Qualifiers
source                  1..57
                        mol_type = other DNA
                        organism = adeno-associated virus
SEQUENCE: 376
cagcgtagat cgtgtgggag ctgcagaagg agaacagcaa gcgcaggaac ccagaat       57

SEQ ID NO: 377          moltype = DNA   length = 60
FEATURE                 Location/Qualifiers
source                  1..60
                        mol_type = other DNA
                        organism = adeno-associated virus
SEQUENCE: 377
cagcgtggag atcgagtggg agctgcagaa ggagaacagc aagcgctgga acccagagat    60

SEQ ID NO: 378          moltype = DNA   length = 60
FEATURE                 Location/Qualifiers
source                  1..60
                        mol_type = other DNA
                        organism = adeno-associated virus
```

```
SEQUENCE: 378
cagcgtggag atcgagtggg agctgcagaa ggagaacagc aagcgctgga gcccagagat   60

SEQ ID NO: 379          moltype = DNA   length = 60
FEATURE                 Location/Qualifiers
source                  1..60
                        mol_type = other DNA
                        organism = adeno-associated virus
SEQUENCE: 379
cagcgtggag atcgagtggg agctgcagaa ggagaacagc aagtgctgga acccagagat   60

SEQ ID NO: 380          moltype = DNA   length = 60
FEATURE                 Location/Qualifiers
source                  1..60
                        mol_type = other DNA
                        organism = adeno-associated virus
SEQUENCE: 380
cagcgtggaa atcgagtggg agctgcagaa ggaaaacagc aagcgctggg acccggagat   60

SEQ ID NO: 381          moltype = DNA   length = 60
FEATURE                 Location/Qualifiers
source                  1..60
                        mol_type = other DNA
                        organism = adeno-associated virus
SEQUENCE: 381
cagcgtggaa atcgagtggg agctgcagaa ggagaacagc aaacgctgga acccagagat   60

SEQ ID NO: 382          moltype = DNA   length = 61
FEATURE                 Location/Qualifiers
source                  1..61
                        mol_type = other DNA
                        organism = adeno-associated virus
SEQUENCE: 382
ccagcgtgga aatcgagtgg gagctgcaga aggagaacag caaacgttgg aacccagaga   60
t                                                                  61

SEQ ID NO: 383          moltype = DNA   length = 60
FEATURE                 Location/Qualifiers
source                  1..60
                        mol_type = other DNA
                        organism = adeno-associated virus
SEQUENCE: 383
cagcgtggag atcgagtggg agctgcagaa ggagaacagc aagcgatgga acccagaaat   60

SEQ ID NO: 384          moltype = DNA   length = 60
FEATURE                 Location/Qualifiers
source                  1..60
                        mol_type = other DNA
                        organism = adeno-associated virus
SEQUENCE: 384
cagcgtggaa atcgaatggg agctgcagaa agaaaacagc aagcgctgga acccagagat   60

SEQ ID NO: 385          moltype = DNA   length = 60
FEATURE                 Location/Qualifiers
source                  1..60
                        mol_type = other DNA
                        organism = adeno-associated virus
SEQUENCE: 385
cagcgtggaa attgaatggg agctgcagaa agagaacagc aagcgctgga acccagagat   60

SEQ ID NO: 386          moltype = DNA   length = 60
FEATURE                 Location/Qualifiers
source                  1..60
                        mol_type = other DNA
                        organism = adeno-associated virus
SEQUENCE: 386
cagcgtggaa attgaatggg agctgcagaa agaaaacagc aaacgctgga acccagagat   60

SEQ ID NO: 387          moltype = DNA   length = 60
FEATURE                 Location/Qualifiers
source                  1..60
                        mol_type = other DNA
                        organism = adeno-associated virus
SEQUENCE: 387
cagcgtggag attgagtggg agctgcagaa ggagaacagc aagcgctgga atcccgagat   60

SEQ ID NO: 388          moltype = DNA   length = 60
FEATURE                 Location/Qualifiers
source                  1..60
```

```
                            mol_type = other DNA
                            organism = adeno-associated virus
SEQUENCE: 388
cagcgtggaa attgaatggg agctgcagaa ggaaaacagc aagcgctgga accccgagat    60

SEQ ID NO: 389              moltype = DNA   length = 60
FEATURE                     Location/Qualifiers
source                      1..60
                            mol_type = other DNA
                            organism = adeno-associated virus
SEQUENCE: 389
cagcgtggaa attgaatggg agctacagaa ggaaaacagc aagcgctgga accccgagat    60

SEQ ID NO: 390              moltype = DNA   length = 60
FEATURE                     Location/Qualifiers
source                      1..60
                            mol_type = other DNA
                            organism = adeno-associated virus
SEQUENCE: 390
cagcgtggaa atcgagtggg agctgcagaa agaaaacagc aagcgctgga atccagagat    60

SEQ ID NO: 391              moltype = DNA   length = 60
FEATURE                     Location/Qualifiers
source                      1..60
                            mol_type = other DNA
                            organism = adeno-associated virus
SEQUENCE: 391
cagcgtggaa atcgagtggg agctgcagaa agaaaacagc aaacgctgga atccagagat    60

SEQ ID NO: 392              moltype = DNA   length = 60
FEATURE                     Location/Qualifiers
source                      1..60
                            mol_type = other DNA
                            organism = adeno-associated virus
SEQUENCE: 392
cagcgtggag atcgagtggg aactgcagaa agaaaacagc aaacactgga atccagagat    60

SEQ ID NO: 393              moltype = DNA   length = 60
FEATURE                     Location/Qualifiers
source                      1..60
                            mol_type = other DNA
                            organism = adeno-associated virus
SEQUENCE: 393
cagcgtggag atcgagtggg aactgcagaa agagaacagc aaacgctgga atccagagat    60

SEQ ID NO: 394              moltype = DNA   length = 60
FEATURE                     Location/Qualifiers
source                      1..60
                            mol_type = other DNA
                            organism = adeno-associated virus
SEQUENCE: 394
cagcgtggag atcgagtggg aactgcagaa agaaaacagc aaacgctgga atccagagat    60

SEQ ID NO: 395              moltype = DNA   length = 60
FEATURE                     Location/Qualifiers
source                      1..60
                            mol_type = other DNA
                            organism = adeno-associated virus
SEQUENCE: 395
cagcgtggaa atcgagtggg agctgcagaa agaaaacagc aagcgctgga acccagaaat    60

SEQ ID NO: 396              moltype = DNA   length = 60
FEATURE                     Location/Qualifiers
source                      1..60
                            mol_type = other DNA
                            organism = adeno-associated virus
SEQUENCE: 396
gagtgtggaa attgaatggg agctgcagaa agaaaacagc aagcgctgga atcccgaagt    60

SEQ ID NO: 397              moltype = DNA   length = 60
FEATURE                     Location/Qualifiers
source                      1..60
                            mol_type = other DNA
                            organism = adeno-associated virus
SEQUENCE: 397
gagcgtggag attgaatggg agctgcagaa agaaaacagc aaacgctgga atcccgaagt    60

SEQ ID NO: 398              moltype = DNA   length = 60
FEATURE                     Location/Qualifiers
```

```
source                  1..60
                        mol_type = other DNA
                        organism = adeno-associated virus
SEQUENCE: 398
cagcgtggag atcgagtggg agctgcagaa ggaaaacagc aaacgctgga atcccgaaat   60

SEQ ID NO: 399          moltype = DNA  length = 60
FEATURE                 Location/Qualifiers
source                  1..60
                        mol_type = other DNA
                        organism = adeno-associated virus
SEQUENCE: 399
cagcgtggag atcgagtggg agctgcagaa ggagaacagc aaacgctgga atcccgaaat   60

SEQ ID NO: 400          moltype = DNA  length = 60
FEATURE                 Location/Qualifiers
source                  1..60
                        mol_type = other DNA
                        organism = adeno-associated virus
SEQUENCE: 400
cagcgtggag atcgagtggg agctgcagaa ggagaacagc aaacgctgga atcccgagat   60

SEQ ID NO: 401          moltype = DNA  length = 60
FEATURE                 Location/Qualifiers
source                  1..60
                        mol_type = other DNA
                        organism = adeno-associated virus
SEQUENCE: 401
cagcgtggag atcgagtggg agctacagaa ggagaacagc aaacgctgga atcccgagat   60

SEQ ID NO: 402          moltype = DNA  length = 60
FEATURE                 Location/Qualifiers
source                  1..60
                        mol_type = other DNA
                        organism = adeno-associated virus
SEQUENCE: 402
cagcgtggag atcgagtggg agctgcagaa ggagaacagc aaacgctgga accccgagat   60

SEQ ID NO: 403          moltype = DNA  length = 60
FEATURE                 Location/Qualifiers
source                  1..60
                        mol_type = other DNA
                        organism = adeno-associated virus
SEQUENCE: 403
cagcgtggag atcgagtggg agctgcagaa ggaggacagc aaacgctgga accccgagat   60

SEQ ID NO: 404          moltype = DNA  length = 59
FEATURE                 Location/Qualifiers
source                  1..59
                        mol_type = other DNA
                        organism = adeno-associated virus
SEQUENCE: 404
cagcgtagag atcgagtggg agctgcagaa ggagaacagc aaacgctgga acccgagat    59

SEQ ID NO: 405          moltype = DNA  length = 60
FEATURE                 Location/Qualifiers
source                  1..60
                        mol_type = other DNA
                        organism = adeno-associated virus
SEQUENCE: 405
cagcgtggag atcgagtggg agctgcagaa agagaacagc aaacgctgga atcccgaaat   60

SEQ ID NO: 406          moltype = DNA  length = 60
FEATURE                 Location/Qualifiers
source                  1..60
                        mol_type = other DNA
                        organism = adeno-associated virus
SEQUENCE: 406
cagcgtggag attgagtggg agctgcagaa ggagaacagc aaacgctgga accccgagat   60

SEQ ID NO: 407          moltype = DNA  length = 60
FEATURE                 Location/Qualifiers
source                  1..60
                        mol_type = other DNA
                        organism = adeno-associated virus
SEQUENCE: 407
cagcgtggag attgagtggg agctgcggaa ggagaacagc aaacgctgga accccgagat   60

SEQ ID NO: 408          moltype = DNA  length = 60
```

```
FEATURE                 Location/Qualifiers
source                  1..60
                        mol_type = other DNA
                        organism = adeno-associated virus
SEQUENCE: 408
cagcgtggaa attgagtggg agctacagaa agaaaacagc aaacgttgga atccagagat   60

SEQ ID NO: 409          moltype = DNA   length = 60
FEATURE                 Location/Qualifiers
source                  1..60
                        mol_type = other DNA
                        organism = adeno-associated virus
SEQUENCE: 409
cagcgtggaa atagagtggg agctgcagaa agaaaacagc aaacgctgga acccagaaat   60

SEQ ID NO: 410          moltype = DNA   length = 60
FEATURE                 Location/Qualifiers
source                  1..60
                        mol_type = other DNA
                        organism = adeno-associated virus
SEQUENCE: 410
cagcgtggag atcgagtggg agctgcagaa ggaaaacagc aagcgctgga acccggagat   60

SEQ ID NO: 411          moltype = DNA   length = 59
FEATURE                 Location/Qualifiers
source                  1..59
                        mol_type = other DNA
                        organism = adeno-associated virus
SEQUENCE: 411
cagcgtggag atcgagtggg agctgcagaa ggaaaacagc aagcgtggaa cccggagat    59

SEQ ID NO: 412          moltype = DNA   length = 60
FEATURE                 Location/Qualifiers
source                  1..60
                        mol_type = other DNA
                        organism = adeno-associated virus
SEQUENCE: 412
cagcgtggag attgagtggg agctgcagaa ggaaaacagc aagcgctgga acccggagat   60

SEQ ID NO: 413          moltype = DNA   length = 60
FEATURE                 Location/Qualifiers
source                  1..60
                        mol_type = other DNA
                        organism = adeno-associated virus
SEQUENCE: 413
cgctgttcag attgaatggg aaatcgaaaa ggaacgctcc aaacgctgga atcctgaagt   60

SEQ ID NO: 414          moltype = DNA   length = 60
FEATURE                 Location/Qualifiers
source                  1..60
                        mol_type = other DNA
                        organism = adeno-associated virus
SEQUENCE: 414
cgctgttcag attgaatggg aaatcgaaaa ggaacgctcc aaacgccgga atcctgaagt   60

SEQ ID NO: 415          moltype = DNA   length = 60
FEATURE                 Location/Qualifiers
source                  1..60
                        mol_type = other DNA
                        organism = adeno-associated virus
SEQUENCE: 415
tgccgttcag atcgactggg aaattcagaa ggagcattcc aaacgctgga atcccgaagt   60

SEQ ID NO: 416          moltype = DNA   length = 60
FEATURE                 Location/Qualifiers
source                  1..60
                        mol_type = other DNA
                        organism = adeno-associated virus
SEQUENCE: 416
gtcggtgcag attgactggg agatccagaa ggagcggtcc aaacgctgga accccgaggt   60

SEQ ID NO: 417          moltype = DNA   length = 60
FEATURE                 Location/Qualifiers
source                  1..60
                        mol_type = other DNA
                        organism = adeno-associated virus
SEQUENCE: 417
ggctgtcaaa atagaatggg aaatccagaa ggagcggtcc aagagatgga acccagaggt   60
```

```
SEQ ID NO: 418          moltype = DNA   length = 60
FEATURE                 Location/Qualifiers
source                  1..60
                        mol_type = other DNA
                        organism = adeno-associated virus
SEQUENCE: 418
caccgtcgaa atcttttggg aactcaagaa ggaaacctcc aagcgctgga accccgaaat    60

SEQ ID NO: 419          moltype = DNA   length = 60
FEATURE                 Location/Qualifiers
source                  1..60
                        mol_type = other DNA
                        organism = adeno-associated virus
SEQUENCE: 419
caccgtggag atggagtggg agctcaagaa ggaaaactcc aagaggtgga acccagagat    60

SEQ ID NO: 420          moltype = DNA   length = 60
FEATURE                 Location/Qualifiers
source                  1..60
                        mol_type = other DNA
                        organism = adeno-associated virus
SEQUENCE: 420
caccgtggag atggaatggg agctcaaaaa ggaaaactcc aagaggtgga acccagagat    60

SEQ ID NO: 421          moltype = DNA   length = 60
FEATURE                 Location/Qualifiers
source                  1..60
                        mol_type = other DNA
                        organism = adeno-associated virus
SEQUENCE: 421
tacagtagag atggtgtggg agctgagaaa agagaattca aagagatgga acccagaaat    60

SEQ ID NO: 422          moltype = DNA   length = 59
FEATURE                 Location/Qualifiers
source                  1..59
                        mol_type = other DNA
                        organism = adeno-associated virus
SEQUENCE: 422
ggagccttac ctggcatggt ctggcagaac cgggacgtgt acctgcaggg tcctatttg     59

SEQ ID NO: 423          moltype = DNA   length = 59
FEATURE                 Location/Qualifiers
source                  1..59
                        mol_type = other DNA
                        organism = adeno-associated virus
SEQUENCE: 423
ggagccttac ctggcatggt ctggcagaac cgggacgtgt acctgcaggg tcccatctg     59

SEQ ID NO: 424          moltype = DNA   length = 59
FEATURE                 Location/Qualifiers
source                  1..59
                        mol_type = other DNA
                        organism = adeno-associated virus
SEQUENCE: 424
ggagccttac ctggtatggt ctggcagaac cgggacgtgt acctgcaggg tcccatctg     59

SEQ ID NO: 425          moltype = DNA   length = 59
FEATURE                 Location/Qualifiers
source                  1..59
                        mol_type = other DNA
                        organism = adeno-associated virus
SEQUENCE: 425
ggagccttac ctggcatggt ctggcagaac cgagacgtgt acctgcaggg tcccatctg     59

SEQ ID NO: 426          moltype = DNA   length = 59
FEATURE                 Location/Qualifiers
source                  1..59
                        mol_type = other DNA
                        organism = adeno-associated virus
SEQUENCE: 426
ggggccttac ctggtatggt ctggcaaaac cgggacgtgt acctgcaggg ccccatctg     59

SEQ ID NO: 427          moltype = DNA   length = 59
FEATURE                 Location/Qualifiers
source                  1..59
                        mol_type = other DNA
                        organism = adeno-associated virus
SEQUENCE: 427
ggagccttac ctggcatggt ctggcagaac cgggacgtgt acctgcaggg tcctatctg     59
```

-continued

```
SEQ ID NO: 428          moltype = DNA   length = 59
FEATURE                 Location/Qualifiers
source                  1..59
                        mol_type = other DNA
                        organism = adeno-associated virus
SEQUENCE: 428
ggggccttac ccggtatggt ctggcagaac cggacgtgt acctgcaggg tcccatctg    59

SEQ ID NO: 429          moltype = DNA   length = 59
FEATURE                 Location/Qualifiers
source                  1..59
                        mol_type = other DNA
                        organism = adeno-associated virus
SEQUENCE: 429
ggagttattc ctggtatggt ctggcagaac cggacgtgt acctgcaggg ccctatttg    59

SEQ ID NO: 430          moltype = DNA   length = 59
FEATURE                 Location/Qualifiers
source                  1..59
                        mol_type = other DNA
                        organism = adeno-associated virus
SEQUENCE: 430
ggggtgattc ccggcatggt gtggcagaat agagacgtgt acctgcaggg tcccatctg    59

SEQ ID NO: 431          moltype = DNA   length = 59
FEATURE                 Location/Qualifiers
source                  1..59
                        mol_type = other DNA
                        organism = adeno-associated virus
SEQUENCE: 431
ggggctctgc ccggcatggt ctggcagaac cggacgtgt acctgcaggg tcccatctg    59

SEQ ID NO: 432          moltype = DNA   length = 59
FEATURE                 Location/Qualifiers
source                  1..59
                        mol_type = other DNA
                        organism = adeno-associated virus
SEQUENCE: 432
ggggctctgc ccggcatggt ctggcagaac cggacgtgt gcctgcaggg tcccatctg    59

SEQ ID NO: 433          moltype = DNA   length = 59
FEATURE                 Location/Qualifiers
source                  1..59
                        mol_type = other DNA
                        organism = adeno-associated virus
SEQUENCE: 433
ggagcactgc ctggcatggt ctggcagaac cgggacgtgt atctgcaggg tcccatctg    59

SEQ ID NO: 434          moltype = DNA   length = 59
FEATURE                 Location/Qualifiers
source                  1..59
                        mol_type = other DNA
                        organism = adeno-associated virus
SEQUENCE: 434
ggagcattac ctggcatggt gtggcaagat agagacgtgt acctgcaggg tcccatttg    59

SEQ ID NO: 435          moltype = DNA   length = 59
FEATURE                 Location/Qualifiers
source                  1..59
                        mol_type = other DNA
                        organism = adeno-associated virus
SEQUENCE: 435
ggagcattac ctggcatggt gtggcaaggt agagacgtgt acctgcaggg tcccatttg    59

SEQ ID NO: 436          moltype = DNA   length = 59
FEATURE                 Location/Qualifiers
source                  1..59
                        mol_type = other DNA
                        organism = adeno-associated virus
SEQUENCE: 436
ggagccttac ctggaatggt gtggcaagac agagacgtat acctgcaggg tcctatttg    59

SEQ ID NO: 437          moltype = DNA   length = 59
FEATURE                 Location/Qualifiers
source                  1..59
                        mol_type = other DNA
                        organism = adeno-associated virus
SEQUENCE: 437
```
ggcgttcttc caggcatggt ctggcaggac agagatgtgt accttcaggg gcccatctg    59

SEQ ID NO: 438           moltype = DNA   length = 59
FEATURE                  Location/Qualifiers
source                   1..59
                         mol_type = other DNA
                         organism = adeno-associated virus
SEQUENCE: 438
ggcgttcttc caggcatggt ctggcaggac agagacgtgt acctgcaggg gcccatctg    59

SEQ ID NO: 439           moltype = DNA   length = 58
FEATURE                  Location/Qualifiers
source                   1..58
                         mol_type = other DNA
                         organism = adeno-associated virus
SEQUENCE: 439
ggcgttcttc caggcatggt gtggcaggac agagacgtgt acctgcaggg gccatctg     58

SEQ ID NO: 440           moltype = DNA   length = 59
FEATURE                  Location/Qualifiers
source                   1..59
                         mol_type = other DNA
                         organism = adeno-associated virus
SEQUENCE: 440
ggcgttcttc caggcatggt ctggcaggac agagacgtgt acctgcaggg gcctatctg    59

SEQ ID NO: 441           moltype = DNA   length = 59
FEATURE                  Location/Qualifiers
source                   1..59
                         mol_type = other DNA
                         organism = adeno-associated virus
SEQUENCE: 441
ggcgttcttc caggcatggt ctggcaggac agagacgtgc acctgcaggg gcctatctg    59

SEQ ID NO: 442           moltype = DNA   length = 59
FEATURE                  Location/Qualifiers
source                   1..59
                         mol_type = other DNA
                         organism = adeno-associated virus
SEQUENCE: 442
ggcgttcttc caggcatggt ctggcaagac agagacgtgt acctgcaggg gcctatttg    59

SEQ ID NO: 443           moltype = DNA   length = 59
FEATURE                  Location/Qualifiers
source                   1..59
                         mol_type = other DNA
                         organism = adeno-associated virus
SEQUENCE: 443
ggcgttcttc caggcatggt cgggcaagac agagacgtgt acctgcaggg gcctacttg    59

SEQ ID NO: 444           moltype = DNA   length = 58
FEATURE                  Location/Qualifiers
source                   1..58
                         mol_type = other DNA
                         organism = adeno-associated virus
SEQUENCE: 444
ggcgttcttc caggcatggt ctggcaggac agagacgtgt acctgcgggg cccatctg     58

SEQ ID NO: 445           moltype = DNA   length = 59
FEATURE                  Location/Qualifiers
source                   1..59
                         mol_type = other DNA
                         organism = adeno-associated virus
SEQUENCE: 445
ggagcgttac ctggtatggt gtggcaggat cgagacgtgt acctgcaggg acccatttg    59

SEQ ID NO: 446           moltype = DNA   length = 59
FEATURE                  Location/Qualifiers
source                   1..59
                         mol_type = other DNA
                         organism = adeno-associated virus
SEQUENCE: 446
ggagcgttac ctggcatggt gtggcaggat cgagacgtgt acctgcaggg acccatttg    59

SEQ ID NO: 447           moltype = DNA   length = 59
FEATURE                  Location/Qualifiers
source                   1..59
                         mol_type = other DNA
                         organism = adeno-associated virus SEQUENCE: 447
ggagcgttac ctggtatggt gtggcaggat cgagatgtgt accttcaggg acccatttg      59

SEQ ID NO: 448          moltype = DNA   length = 59
FEATURE                 Location/Qualifiers
source                  1..59
                        mol_type = other DNA
                        organism = adeno-associated virus
SEQUENCE: 448
ggagcattac ctggtatggt gtggcaggat cgagacgtgt acctgcaggg acccatttg      59

SEQ ID NO: 449          moltype = DNA   length = 59
FEATURE                 Location/Qualifiers
source                  1..59
                        mol_type = other DNA
                        organism = adeno-associated virus
SEQUENCE: 449
ggagcattac ctggtatggt gtggcaggat cgagacgtgt acctgcgggg acccatttg      59

SEQ ID NO: 450          moltype = DNA   length = 59
FEATURE                 Location/Qualifiers
source                  1..59
                        mol_type = other DNA
                        organism = adeno-associated virus
SEQUENCE: 450
ggggccttac ctggcatggt gtggcaagat cgtgacgtgt accttcaagg acctatctg      59

SEQ ID NO: 451          moltype = DNA   length = 58
FEATURE                 Location/Qualifiers
source                  1..58
                        mol_type = other DNA
                        organism = adeno-associated virus
SEQUENCE: 451
ggagcgttac ctggtatggt gtggcaggat cgagacgtgt actgcaggga cccatttg       58

SEQ ID NO: 452          moltype = DNA   length = 59
FEATURE                 Location/Qualifiers
source                  1..59
                        mol_type = other DNA
                        organism = adeno-associated virus
SEQUENCE: 452
ggaatcttac ctggaatggt gtggcaggac cgcgatgtct atcttcaagg tcccatttg      59

SEQ ID NO: 453          moltype = DNA   length = 59
FEATURE                 Location/Qualifiers
source                  1..59
                        mol_type = other DNA
                        organism = adeno-associated virus
SEQUENCE: 453
ggaatacttc cgggtatggt ttggcaggac agagatgtgt acctgcaagg acccatttg      59

SEQ ID NO: 454          moltype = DNA   length = 59
FEATURE                 Location/Qualifiers
source                  1..59
                        mol_type = other DNA
                        organism = adeno-associated virus
SEQUENCE: 454
ggagtgcttc ctggcatggt gtggcaaaac agagacattt actaccaagg gccaatttg      59

SEQ ID NO: 455          moltype = DNA   length = 59
FEATURE                 Location/Qualifiers
source                  1..59
                        mol_type = other DNA
                        organism = adeno-associated virus
SEQUENCE: 455
ggagtgctgc ctggcatggt gtggcaaaac agagacattt actaccaagg gccaatttg      59

SEQ ID NO: 456          moltype = DNA   length = 59
FEATURE                 Location/Qualifiers
source                  1..59
                        mol_type = other DNA
                        organism = adeno-associated virus
SEQUENCE: 456
ggaattgttc ccggaatggt ctggcaaaac agagacatct actaccaggg ccctatttg      59

SEQ ID NO: 457          moltype = DNA   length = 59
FEATURE                 Location/Qualifiers
source                  1..59
                        mol_type = other DNA

```
                        organism = adeno-associated virus
SEQUENCE: 457
ggagccgtgc ctggaatggt gtggcaaaac agagacattt actaccaggg tcccatttg    59

SEQ ID NO: 458          moltype = DNA  length = 59
FEATURE                 Location/Qualifiers
source                  1..59
                        mol_type = other DNA
                        organism = adeno-associated virus
SEQUENCE: 458
ggcgtgtacc cgggaatggt gtggcaggac agagacattt actaccaagg gcccatttg    59

SEQ ID NO: 459          moltype = DNA  length = 60
FEATURE                 Location/Qualifiers
source                  1..60
                        mol_type = other DNA
                        organism = adeno-associated virus
SEQUENCE: 459
ggggcgcttc ccgggatggt gtggcaaaac agagacattt accctacagg gacccatttg   60

SEQ ID NO: 460          moltype = DNA  length = 59
FEATURE                 Location/Qualifiers
source                  1..59
                        mol_type = other DNA
                        organism = adeno-associated virus
SEQUENCE: 460
gaaatcgtgc ccggcagcgt gtggatggag agggacgtgt acctccaagg acccatctg    59

SEQ ID NO: 461          moltype = DNA  length = 58
FEATURE                 Location/Qualifiers
source                  1..58
                        mol_type = other DNA
                        organism = adeno-associated virus
SEQUENCE: 461
gaagtgcttc ctggcagcgt atggatggag agggacgtgt acctccagga cccatctg     58

SEQ ID NO: 462          moltype = DNA  length = 59
FEATURE                 Location/Qualifiers
source                  1..59
                        mol_type = other DNA
                        organism = adeno-associated virus
SEQUENCE: 462
ggagctttac caggaatggt ttggcagaac agggatatat atctgcaggg acctattgg    59

SEQ ID NO: 463          moltype = DNA  length = 10
FEATURE                 Location/Qualifiers
source                  1..10
                        mol_type = other DNA
                        organism = adeno-associated virus
SEQUENCE: 463
gggagctaca                                                          10
```

The invention claimed is:

1. An adeno-associated virus serotype 9 (AAV9) capsid protein comprising an amino acid insertion within loop 8, wherein the amino acid insertion comprises SEQ ID NO: 128, and wherein the AAV9 capsid protein without the amino acid insertion comprises 90% sequence identity to SEQ ID NO: 221.

2. The AAV9 capsid protein of claim 1, wherein the AAV9 capsid protein comprises a N272A mutation.

3. The AAV9 capsid protein of claim 1, wherein the AAV9 capsid protein comprises SEQ ID NO: 221.

4. The AAV9 capsid protein of claim 1, wherein the AAV9 capsid protein comprises SEQ ID NO: 222.

5. The AAV9 capsid protein of claim 1 wherein the amino acid insertion within loop 8 comprises a substitution of position 588 of SEQ ID NO: 221 with the amino acid insertion.

6. The AAV9 capsid protein of claim 1, wherein the amino acid insertion further comprises a linker.

7. A nucleic acid molecule encoding an adeno-associated virus serotype 9 (AAV9) capsid protein comprising an amino acid insertion within loop 8 of the AAV9 capsid protein, wherein the amino acid insertion comprises SEQ ID NO: 128, and wherein the AAV9 capsid protein without the amino acid insertion comprises 90% sequence identity to SEQ ID NO: 221.

8. The nucleic acid molecule of claim 7, wherein the AAV9 capsid protein comprises a N272A mutation.

9. The nucleic acid molecule of claim 7, wherein the AAV9 capsid protein comprises SEQ ID NO: 221.

10. The nucleic acid molecule of claim 7, wherein the AAV9 capsid protein comprises SEQ ID NO: 222.

11. The nucleic acid molecule of claim 7, wherein the amino acid insertion within loop 8 comprises a substitution of position 588 of SEQ ID NO: 221 with the amino acid insertion.

12. The nucleic acid molecule of claim 7, wherein the amino acid insertion further comprises a linker.

* * * * *